United States Patent
Bradley et al.

(10) Patent No.: US 8,901,373 B2
(45) Date of Patent: Dec. 2, 2014

(54) METHODS AND COMPOSITIONS FOR ROOT KNOT NEMATODE CONTROL

(75) Inventors: John D. Bradley, St. Louis, MO (US); Brandi J. Chiapelli, Saint Louis, MO (US); Bingli Gao, Chesterfield, MO (US); James P. McCarter, St. Louis, MO (US); Michelle L. Gasper, St. Charles, MO (US); Deryck Jeremy Williams, University City, MO (US)

(73) Assignee: Monsanto Technology LLC, St. Louis, MO (US)

( * ) Notice: Subject to any disclaimer, the term of this patent is extended or adjusted under 35 U.S.C. 154(b) by 582 days.

(21) Appl. No.: 12/935,266

(22) PCT Filed: Apr. 10, 2009

(86) PCT No.: PCT/US2009/040224
§ 371 (c)(1),
(2), (4) Date: Dec. 20, 2010

(87) PCT Pub. No.: WO2009/126896
PCT Pub. Date: Oct. 15, 2009

(65) Prior Publication Data
US 2012/0030834 A1    Feb. 2, 2012

Related U.S. Application Data

(60) Provisional application No. 61/044,015, filed on Apr. 10, 2008, provisional application No. 61/084,205, filed on Jul. 28, 2008.

(51) Int. Cl.
| | | |
|---|---|---|
| *C12N 15/113* | (2010.01) | |
| *C12N 15/82* | (2006.01) | |
| *A01H 5/00* | (2006.01) | |
| *A01H 5/10* | (2006.01) | |
| *C12N 15/87* | (2006.01) | |
| *C07K 14/435* | (2006.01) | |

(52) U.S. Cl.
CPC ........ *C07K 14/4354* (2013.01); *C12N 15/8218* (2013.01); *C12N 15/8285* (2013.01)
USPC ....... 800/279; 536/24.5; 435/320.1; 800/301; 800/295; 800/285; 426/615

(58) Field of Classification Search
None
See application file for complete search history.

(56) References Cited

U.S. PATENT DOCUMENTS

| | | | |
|---|---|---|---|
| 6,506,559 B1 | 1/2003 | Fire et al. | |
| 7,576,261 B2 | 8/2009 | Hussey et al. | |
| 7,622,301 B2 | 11/2009 | Ren et al. | |
| 7,659,444 B2 | 2/2010 | Ren et al. | |
| 7,803,984 B2 | 9/2010 | Trick et al. | |
| 8,088,976 B2 * | 1/2012 | Boukharov et al. | 800/285 |
| 2003/0061626 A1 | 3/2003 | Plaetinck et al. | |
| 2003/0150017 A1 | 8/2003 | Mesa et al. | |
| 2004/0098761 A1 | 5/2004 | Trick et al. | |
| 2004/0133943 A1 | 7/2004 | Plaetinck et al. | |
| 2005/0188438 A1 | 8/2005 | Ren et al. | |
| 2006/0037101 A1 | 2/2006 | Ren et al. | |
| 2006/0080749 A1 | 4/2006 | Hussey et al. | |
| 2006/0147961 A1 | 7/2006 | Dong et al. | |

FOREIGN PATENT DOCUMENTS

| | | |
|---|---|---|
| WO | WO 01/37654 A2 | 5/2001 |
| WO | WO 03/52110 A2 | 6/2003 |
| WO | WO 2004/061087 A2 | 7/2004 |
| WO | WO 2005/019408 A2 | 3/2005 |
| WO | WO 2006/047495 A2 | 5/2006 |
| WO | WO 2007/087153 A2 | 8/2007 |
| WO | WO 2007/095469 A2 | 8/2007 |
| WO | WO 2007/104570 A2 | 9/2007 |

OTHER PUBLICATIONS

Thomas et al, 2001, Plant J., 25:417-425.*
Kikuchi et al, 2003, Science, 301:376-379.*
Rai et al, 2001, Current Science, 80:1121-1128.*
Aboobaker et al., "Medical significance of *Caenorhabditis elegans*," *Ann. Med.*, 32:23-30, 2000.
Fairbairn et al., "Host-delivered RNAi: an effective strategy to silence genes in plant parasitic nematodes," *Planta*, 226:1525-1533, 2007.
Fairbairn et al., "Plant delivered RNAi (PD-RNAi): a novel strategy to control plant parasitic nematodes by inactivating nematode genes in planta," American Society of Plant Biologists, Annual Meeting, Abstract 372, Seattle, WA, Jul. 16-Jul. 20, 2005.
Fire et al., "Potent and specific genetic interference by double-stranded RNA in *Caenorhabditis elegans*," *Nature*, 391:806-811, 1998.
GenBank Accession No. HP560922, dated Oct. 19, 2010. Huang et al., "Engineering broad root-knot resistance in transgenic plants by RNAi silencing of a conserved and essential root-knot nematode parasitism gene," *PNAS*, 103(39):14302-14306, 2006.
Hussein et al., "Suppression of secreted acetylcholinesterase expression in *Nippostrongylus brasiliensis* by RNA interference," *Mol. Biochem. Parasitol.*, 122:91-94, 2002.
Lee et al., "Regulation of gene expression, cellular localization, and in vivo function of *Caenorhabditis elegans* DNA topoisomerase I," *Genes to Cells*, 6:303-312, 2001.

(Continued)

*Primary Examiner* — Ashwin Mehta
*Assistant Examiner* — Jason Deveau Rosen
(74) *Attorney, Agent, or Firm* — Dentons US LLP; T.K. Ball, Esq.

(57) ABSTRACT

The present invention discloses gene targets, constructs and methods for the genetic control of plant disease caused by nematodes of the genus *Meloidogyne* (root knot nematodes). The present invention relates to achieving a plant protective effect through the identification of target coding sequences and the use of recombinant DNA technologies for post-transcriptionally repressing or inhibiting expression of the target coding sequences in the cells of plant-parasitic nematodes. The disclosed gene targets show significant conservation at the nucleotide level between orthologs from different *Meloidogyne* species, facilitating genus-wide targeting by RNA interference.

42 Claims, 2 Drawing Sheets

(56) References Cited

OTHER PUBLICATIONS

NCBI Accession No. XM_002642568, dated Nov. 17, 2009.

NCBI Accession No. XM_003138053, dated Nov. 15, 2010.

Steeves et al., "Transgenic soybeans expressing siRNAs specific to major sperm protein gene suppress heterodera glycines reproduction," *Functional Plant Biology*, 33:991-999, 2006.

Urwin et al., "Ingestion of double-stranded RNA by preparasitic juvenile cyst nematodes leads to RNA interference," *Mol. Plant-Microbe Interact.*, 15:747-752, 2002.

Yadav et al., "Host-generated double stranded RNA induces RNAi in plant-parasitic nematodes and protects the host from infection," *Molecular & Biochemical Parasitology*, 148:219-222, 2006.

Kamath et al., "Systematic functional analysis of the *Caenorhabditis elegans* genome using RNAi," Nature, 421; Jan. 2003, pp. 231-237.

Ford et al., "Functional Analysis of the Cathepsin-Like Cysteine Protease Genes in Adult *Brugia malayi* using RNA interference," *PLoS Neglected Tropical Diseases*; 3(2):e377.doi:10:1371; 2009.

Wu et al., Improved siRNA/shRNA Functionality by Mismatched Duplex; *PLoS ONE* 6(12):e28580, doi:10.1371; Dec. 2011.

Eki et al., "A Genome-wide Survey and Systematic RNAi-based Characterization of Helicase-like Genes in *Caenorhabditis elegans*," *DNA Research*, 14:183-199, 2007.

\* cited by examiner

US 8,901,373 B2

METHODS AND COMPOSITIONS FOR ROOT KNOT NEMATODE CONTROL

CROSS REFERENCE TO RELATED APPLICATIONS

This application claims priority to U.S. Provisional Application Ser. No. 61/044,015, filed Apr. 10, 2008, and to U.S. Provisional Application Ser. No. 61/084,205, filed Jul. 28, 2008, the entire disclosures of which are incorporated herein by reference.

INCORPORATION-BY-REFERENCE OF SEQUENCE LISTING IN COMPUTER READABLE FORM

The Sequence Listing, which is a part of the present disclosure, includes a computer readable form 113 KB file entitled "MNDI004WO_ST25.txt" created Apr. 10, 2009, comprising nucleotide sequences of the present invention. The subject matter of the Sequence Listing is incorporated herein by reference in its entirety.

BACKGROUND OF THE INVENTION

1. Field of the Invention

The present invention relates generally to genetic control of plant disease caused by plant-parasitic nematodes. More specifically, the present invention relates to identification of target coding sequences, and to use of recombinant DNA technologies for post-transcriptionally repressing or inhibiting expression of target coding sequences in the cells of a plant-parasitic nematode to provide a plant protective effect.

2. Description of Related Art

Plants are subject to multiple potential disease causing agents, including plant-parasitic nematodes, which are active, flexible, elongate organisms that live on moist surfaces or in liquid environments, including films of water within soil and moist tissues within other organisms. There are numerous plant-parasitic nematode species, including various root knot nematodes (e.g. *Meloidogyne* sp.), lesion nematodes (e.g. *Pratylenchus* sp.), cyst nematodes (e.g. *Heterodera* sp.), dagger nematodes (e.g. *Xiphinema* sp.) and stem and bulb nematodes (e.g. *Ditylenchus* sp.), among others. Tylenchid nematodes (members of the order Tylenchida), including the families Heteroderidae, Meloidogynidae, and Pratylenchidae, are the largest and most economically important group of plant-parasitic nematodes. Nematode species grow through a series of lifecycle stages and molts. Typically, there are five stages and four molts: egg stage; J1 (i.e. first juvenile stage); M1 (i.e. first molt); J2 (second juvenile stage; sometimes hatch from egg); M2; J3; M3; J4; M4; A (adult). Juvenile ("J") stages are also sometimes referred to as larval ("L") stages. Gene expression may be specific to one or more lifecycle stages.

Both plant-specific and animal-specific species of nematodes have evolved as very successful parasites and are responsible for significant economic losses in agriculture and livestock and for morbidity and mortality in humans. Nematode parasites of plants can inhabit all parts of plants, including roots, developing flower buds, leaves, and stems. Plant parasites are classified on the basis of their feeding habits into the broad categories migratory ectoparasites, migratory endoparasites, and sedentary endoparasites. Sedentary endoparasites, which include the root knot nematodes (*Meloidogyne* spp.) and cyst nematodes (*Globodera* and *Heterodera*) induce feeding sites ("giant cells" in the case of root knot nematodes and "syncytia" for cyst nematodes) and establish long-term infections within roots that are often very damaging to crops. It is estimated that parasitic nematodes cost the horticulture and agriculture industries in excess of $78 billion worldwide a year, based on an estimated average 12% annual loss spread across all major crops. For example, it is estimated that nematodes annually cause soybean losses of approximately $3.2 billion worldwide (Barker et al., 1994).

Compositions, methods, and agents for controlling infestations by nematodes have been provided in several forms. Biological and cultural control methods, including plant quarantines, have been attempted in numerous instances. In some crops, plant resistance genes have been identified that allow nematode resistance or tolerance. Chemical compositions such as nematocides have typically been applied to soil in which plant parasitic nematodes are present. However, there is an urgent need for safe and effective nematode controls. Factors relating to the disadvantages of current control strategies include heightened concern for the sustainability of agriculture, and new government regulations that may prevent or severely restrict the use of many available agricultural chemical antihelminthic agents.

Chemical agents are often not selective, and exert their effects on non-target organisms, effectively disrupting populations of beneficial microorganisms, for a period of time following application of the agent. Chemical agents may persist in the environment and only be slowly metabolized. Nematocidal soil fumigants such as chloropicrin and methyl bromide and related compounds are highly toxic. Methyl bromide has been identified as an ozone-depleting compound, and its registration for use in the United States is being removed. These agents may also accumulate in the water table or the food chain, and in higher trophic level species. These agents may also act as mutagens and/or carcinogens to cause irreversible and deleterious genetic modifications. Thus, alternative methods for nematode control, such as genetic methods, are increasingly being studied.

RNA interference ("RNAi") is a process utilizing endogenous cellular pathways whereby a double stranded RNA (dsRNA) specific target gene results in the degradation of the mRNA of interest. RNAi works through an endogenous pathway including the Dicer protein complex that generates ~21-nucleotide small interfering RNAs (siRNAs) from the original dsRNA and the RNA-induced silencing complex (RISC) that uses siRNA guides to recognize and degrade or block the translation from the corresponding mRNAs. Only transcripts complementary to the siRNA are affected, and thus the knock-down of mRNA expression is usually sequence specific. The gene silencing effect of RNAi persists for days and, under experimental conditions, can lead to a decline in abundance of the targeted transcript of 90% or more, with consequent decline in levels of the corresponding protein.

The GOI can be driven by strong constitutive promoters derived from the cauliflower mosaic virus 35S promoter (35S) or figwort mosaic virus (FMV) or a variety of plant promoters such as the ubiquitin 3 promoter and terminators such as the E6, E9 or octopine synthase (OCS) terminator can be used. The red fluorescent protein DsRed can be driven by strong constitutive viral promoters or other promoters such as the actin 7 plant promoter with the use of terminators such as E6, E9 or OCS.

Figure 2:
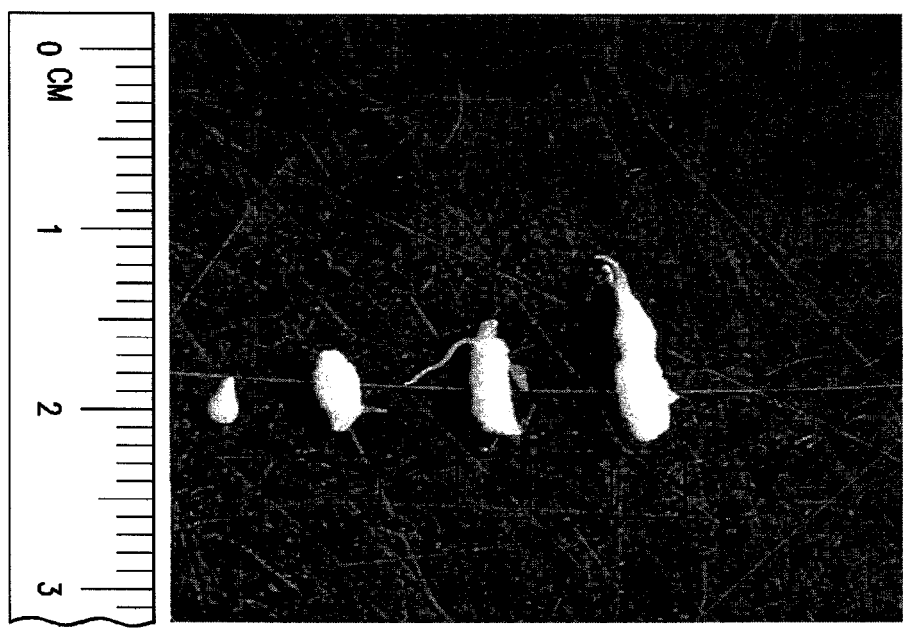

FIG. 2: shows an example of the nematode rating scale (1-4) used in Example 2.

SUMMARY OF THE INVENTION

In one aspect, the present invention comprises an polynucleotide selected from the group consisting of: (a) a fragment of at least 21 contiguous nucleotides of a nucleic acid sequence of any of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:28, SEQ ID NO:29, SEQ ID NO:30, SEQ ID NO:32, SEQ ID NO:40, SEQ ID NO:42, SEQ ID NO:44, SEQ ID NO:46, or SEQ ID NO:47, wherein uptake by a plant-parasitic nematode of a double stranded ribonucleotide sequence comprising at least one strand that is complementary to said fragment inhibits the growth of the nematode; and (b) a complement of the sequence of (a). In certain embodiments, the polynucleotide is defined as operably linked to a heterologous promoter. By "heterologous" is meant any sequence, e.g. promoter, which is not naturally found joined to the polynucleotide, including, for example, a combination of nucleic acid sequences from the same plant which are not naturally found joined together. In certain embodiments the polynucleotide is comprised on a plant transformation vector. In further embodiments of the invention, a polynucleotide sequence provided herein may be defined as an isolated polynucleotide sequence.

Another aspect of the invention is a double stranded ribonucleotide sequence produced from the expression of such a polynucleotide, wherein the taking up of the ribonucleotide sequence by a plant-parasitic nematode inhibits the growth of the nematode. In certain embodiments the double stranded ribonucleotide sequence is further defined as produced by preparing a recombinant polynucleotide sequence comprising a first, a second and a third polynucleotide sequence, wherein the first polynucleotide sequence comprises an polynucleotide selected from the group consisting of: (a) a fragment of at least 21 contiguous nucleotides of a nucleic acid sequence of any of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:28, SEQ ID NO:29, SEQ ID NO:30, SEQ ID NO:32, SEQ ID NO:40, SEQ ID NO:42, SEQ ID NO:44, SEQ ID NO:46, or SEQ ID NO:47, wherein uptake by a plant-parasitic nematode of a double stranded ribonucleotide sequence comprising at least one strand that is complementary to said fragment inhibits the growth of the nematode; and (b) a complement of the sequence of (a); and wherein the third polynucleotide sequence is linked to the first polynucleotide sequence by the second polynucleotide sequence, and wherein the third polynucleotide sequence is substantially the reverse complement of the first polynucleotide sequence such that the first and the third polynucleotide sequences hybridize when transcribed into a ribonucleic acid to form the double stranded ribonucleotide molecule stabilized by the linked second ribonucleotide sequence. In particular embodiments, the double stranded ribonucleotide sequence inhibits the expression of a nucleotide sequence substantially complementary to the polynucleotide sequence, when the polynucleotide sequence is taken up by the plant-parasitic nematode.

Another aspect of the invention is a plant transformation vector comprising a nucleotide sequence selected from the group consisting of: (a) a fragment of at least 21 contiguous nucleotides of a nucleic acid sequence of any of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:28, SEQ ID NO:29, SEQ ID NO:30, SEQ ID NO:32, SEQ ID NO:40, SEQ ID NO:42, SEQ ID NO:44, SEQ ID NO:46, or SEQ ID NO:47, wherein uptake by a plant-parasitic nematode of a double stranded ribonucleotide sequence comprising at least one strand that is complementary to said fragment inhibits the growth of the nematode; and (b) a complement of the sequence of (a); wherein the DNA sequence is operably linked to a heterologous promoter functional in a plant cell. A further embodiment of the invention is a cell transformed with such a polynucleotide. In certain embodiments, the cell is defined as prokaryotic cell, or a eukaryotic cell. In a particular embodiment, the cell is defined as a plant cell.

Another embodiment of the invention relates to a plant transformed with the polynucleotide selected from the group consisting of: (a) a fragment of at least 21 contiguous nucleotides of a nucleic acid sequence of any of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:28, SEQ ID NO:29, SEQ ID NO:30, SEQ ID NO:32, SEQ ID NO:40, SEQ ID NO:42, SEQ ID NO:44, SEQ ID NO:46, or SEQ ID NO:47, wherein uptake by a plant-parasitic nematode of a double stranded ribonucleotide molecule comprising at least one strand that is complementary to said fragment inhibits the growth of the nematode; and (b) a complement of the sequence of (a). The plant, in certain embodiments, is further defined as selected from a crop selected from the group consisting of: corn, wheat, barley, rye, rice, potato, tomato, cucumber, pepper, clover, legume, soybean, pea, alfalfa, sugar cane, sugar beet, tobacco, carrot, cotton, rapeseed (canola), sunflower, safflower, sorghum, strawberry, banana, turf, and an ornamental plant. A seed of such a plant, wherein the seed comprises the polynucleotide, is another embodiment of the invention. In some embodiments, the polynucleotide is expressed in the plant or plant cell, such as a root cell, as a double stranded ribonucleotide sequence. In other embodiments, the plant-parasitic nematode is a *Meloidogyne* spp. In particular embodiments the plant-parasitic nematode is *Meloidogyne incognita*. In yet other embodiments, the taking up of the plant-parasitic nematode inhibitory amount of the double stranded ribonucleotide sequence inhibits growth or reproduction of the nematode.

Another aspect of the invention is a commodity product produced from a plant comprising a polynucleotide selected from the group consisting of: (a) a fragment of at least 21 contiguous nucleotides of a nucleic acid sequence of any of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:28, SEQ ID NO:29, SEQ ID NO:30, SEQ ID NO:32, SEQ ID NO:40, SEQ ID NO:42, SEQ ID NO:44, SEQ ID NO:46, or SEQ ID NO:47, wherein uptake by a plant-parasitic nematode of a double stranded ribonucleotide sequence comprising at least one strand that is complementary to said fragment inhibits the growth of the nematode; and (b) a complement of the sequence of (a), wherein the commodity product comprises a detectable amount of the polynucleotide or a ribonucleotide expressed therefrom.

Another aspect of the invention is a method for controlling a plant-parasitic nematode population comprising providing an agent comprising a double stranded ribonucleotide sequence that functions upon being taken up by the nematode to inhibit a biological function within the nematode, wherein the agent comprises a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:28, SEQ ID NO:29, SEQ ID NO:30, SEQ ID NO:32, SEQ ID NO:40, SEQ ID NO:42, SEQ ID NO:44, SEQ ID NO:46, and SEQ ID NO:47, and complements thereof.

Yet another aspect of the invention is a method for controlling a plant-parasitic nematode population comprising providing an agent comprising a first polynucleotide sequence that functions upon being taken up by a plant-parasitic nematode to inhibit a biological function within the nematode, wherein the polynucleotide sequence exhibits from about 95 to about 100% nucleotide sequence identity along at least from about 19 to about 25 contiguous nucleotides to a coding sequence derived from the nematode and is hybridized to a second polynucleotide sequence that is complementary to the first polynucleotide sequence, and wherein the coding sequence derived from the nematode is selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:28, SEQ ID NO:29, SEQ ID NO:30, SEQ ID NO:32, SEQ ID NO:40, SEQ ID NO:42, SEQ ID NO:44, SEQ ID NO:46, and SEQ ID NO:47, and the complements thereof. In certain embodiments, the nematode is *Meloidogyne* spp. In particular embodiments the nematode is *Meloidogyne incognita*.

Another embodiment of the invention is a method for controlling a plant-parasitic nematode population comprising providing in the host plant of a plant-parasitic nematode a transformed plant cell expressing a polynucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:28, SEQ ID NO:29, SEQ ID NO:30, SEQ ID NO:32, SEQ ID NO:40, SEQ ID NO:42, SEQ ID NO:44, SEQ ID NO:46, and SEQ ID NO:47, a fragment of at least 21 contiguous nucleotides of any of these polynucleotide sequences, and complements thereof, wherein the polynucleotide is expressed to produce a double stranded ribonucleic acid that functions upon being taken up by the plant-parasitic nematode to inhibit the expression of a target sequence within the nematode and results in decreased growth or reproduction of the nematode or nematode population, relative to growth or reproduction on a host lacking the transformed plant cell. In certain embodiments the nematode exhibits decreased growth following infection of the host plant. Particular embodiments of the method, wherein the target sequence encodes a protein, the predicted function of which is selected from the group consisting of: DNA replication, cell cycle control, transcription, RNA processing, translation, ribosome function, tRNA synthesis, tRNA function, protein trafficking, secretion, protein modification, protein stability, protein degradation, energy production, mitochondrial function, intermediary metabolism, cell structure, signal transduction, endocytosis, ion regulation, egg production, reproduction, and transport, are also a part of the invention. In particular embodiments the nematode is selected from the group consisting of *Meloidogyne* spp. In more particular embodiments the nematode is *Meloidogyne incognita*. In some embodiments the polynucleotide functions upon being taken up by the plant-parasitic nematode to suppress a gene that performs a function essential for nematode survival, reproduction, or growth, said function being selected from the group consisting of DNA replication, cell cycle control, transcription, RNA processing, translation, ribosome function, tRNA synthesis, tRNA function, protein trafficking, secretion, protein modification, protein stability, protein degradation, energy production, mitochondrial function, intermediary metabolism, cell structure, signal transduction, endocytosis, ion regulation, egg production, and transport.

Another aspect of the invention is a method for reducing the number of root knot nematode (RKN) feeding sites established in the root tissue of a host plant, comprising providing in the host plant of a *Meloidogyne* sp. a transformed plant cell expressing a polynucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:28, SEQ ID NO:29, SEQ ID NO:30, SEQ ID NO:32, SEQ ID NO:40, SEQ ID NO:42, SEQ ID NO:44, SEQ ID NO:46, and SEQ ID NO:47, a fragment of at least 21 contiguous nucleotides of any of these polynucleotide sequences, and the complements thereof, wherein the polynucleotide is expressed to produce a double stranded ribonucleic acid that functions upon being taken up by the *Meloidogyne* sp. to inhibit the expression of a target sequence within said nematode and results in a decrease in the number of feeding sites established, relative to the number of feeding sites established on a host lacking the transformed plant cell.

Another embodiment of the invention is a method of controlling plant nematode pest infestation in a plant comprising providing in the diet of a plant nematode pest a dsRNA comprising: a) a sense nucleotide sequence; and b) an antisense nucleotide sequence complementary to the sense nucleotide sequence, wherein the sense nucleotide sequence comprises or is complementary to a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:28, SEQ ID NO:29, SEQ ID NO:30, SEQ ID NO:32, SEQ ID NO:40, SEQ ID NO:42, SEQ ID NO:44, SEQ ID NO:46, and SEQ ID NO:47, and the complements thereof. In one embodiment, the diet comprises a plant cell transformed to express the sense and the antisense nucleotide sequence.

The invention also relates to a method for improving the yield of a crop produced from a crop plant subjected to plant-parasitic nematode infection, said method comprising the steps of: a) introducing a polynucleotide as described herein into said crop plant; and b) cultivating the crop plant to allow the expression of said polynucleotide; wherein expression of the polynucleotide inhibits plant-parasitic nematode infection, growth, reproduction, or loss of yield due to plant-parasitic nematode infection. In certain embodiments the crop plant is selected from the group consisting of: corn, wheat, barley, rye, rice, potato, tomato, cucumber, pepper, clover, legume, soybean, pea, alfalfa, sugar cane, sugar beet, tobacco, carrot, cotton, rapeseed (canola), sunflower, safflower, sorghum, strawberry, banana, turf, and ornamental plants. In some embodiments, the expression of the polynucleotide produces an RNA molecule that suppresses at least a first target gene in a plant-parasitic nematode that has contacted a portion of said crop plant, wherein the target gene performs at least one essential function selected from the group consisting of DNA replication, cell cycle control, transcription, RNA processing, translation, ribosome function, tRNA synthesis, tRNA function, protein trafficking, secretion, protein modification, protein stability, protein degradation, energy production, mitochondrial function, intermediary metabolism, cell structure, signal transduction, endocytosis, ion regulation, egg production, reproduction, and transport. In certain embodiments the plant-parasitic nematode is a Tylenchid nematode. In particular embodiments the plant-parasitic nematode is a *Meloidogyne* sp. In even more particular embodiments the plant-parasitic nematode is *Meloidogyne incognita*.

Another aspect of the invention is a method for improving the osmotic stress tolerance of a crop plant subjected to plant-parasitic nematode infection, said method comprising the steps of, a) introducing a polynucleotide according to claim 1 into said crop plant; b) cultivating the crop plant to allow the expression of said polynucleotide; wherein expression of the polynucleotide improves the osmotic stress tolerance of the crop plant. In some embodiments the osmotic stress tolerance is defined as drought tolerance.

Yet another aspect of the invention is a method of producing a commodity product comprising obtaining a plant comprising at least 21 contiguous nucleotides of a nucleic acid sequence of any of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:28, SEQ ID NO:29, SEQ ID NO:30, SEQ ID NO:32, SEQ ID NO:40, SEQ ID NO:42, SEQ ID NO:44, SEQ ID NO:46, or SEQ ID NO:47, wherein uptake by a plant-parasitic nematode of a double stranded ribonucleotide sequence comprising at least one strand that is complementary to said fragment inhibits the growth of the nematode; and (b) a complement of the sequence of (a); or a part thereof, and preparing a commodity product from the plant or part thereof. The invention also relates to a method of producing food or feed, comprising obtaining such a plant, or a part thereof, and preparing food or feed from said plant or part thereof. In certain embodiments the food or feed is defined as oil, meal, protein, starch, flour or silage.

Yet another aspect of the invention is a method for modulating the expression of a target gene in a plant-parasitic nematode cell, the method comprising: (a) transforming a plant cell with a vector comprising a nucleic acid sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:28, SEQ ID NO:29, SEQ ID NO:30, SEQ ID NO:32, SEQ ID NO:40, SEQ ID NO:42, SEQ ID NO:44, SEQ ID NO:46, SEQ ID NO:47, and a fragment of at least 21 contiguous nucleotides of any of these sequences, wherein the nucleic acid sequence encodes a dsRNA and is operatively linked to a promoter and a transcription termination sequence; (b) culturing the transformed plant cell under conditions sufficient to allow for development of a plant cell culture comprising a plurality of transformed plant cells; (c) selecting for transformed plant cells that have integrated the nucleic acid sequence into their genomes; (d) screening the transformed plant cells for expression of the dsRNA encoded by the nucleic acid sequence; and (e) selecting a plant cell that expresses the dsRNA. A method further comprising regenerating a plant from the plant cell that expresses the dsRNA; whereby expression of the gene in the plant is sufficient to modulate the expression of a target gene in a plant-parasitic nematode cell that contacts the transformed plant or plant cell is another embodiment of the invention.

DETAILED DESCRIPTION OF THE INVENTION

The following is a detailed description of the invention provided to aid those skilled in the art in practicing the present invention. Those of ordinary skill in the art may make modifications and variations in the embodiments described herein without departing from the spirit or scope of the present invention.

The present invention provides methods and compositions for genetic control of plant-parasitic nematode infestations, particularly for genetic control of *Meloidogyne* (root knot) nematode infestations of plants. Identification of genes essential in the lifecycle of a *Meloidogyne* plant-parasitic nematode and methods for their use as a target for dsRNA-mediated control of a nematode population are also provided. DNA plasmid vectors encoding dsRNA molecules are designed to suppress nematode genes essential for growth, development, feeding, or reproduction. For example, the present invention provides methods and recombinant DNA technologies for post-transcriptionally repressing or inhibiting expression of a target coding sequence in a plant-parasitic nematode to provide a protective effect by allowing the plant-parasitic nematode to ingest one or more double stranded or small interfering ribonucleic acid (RNA) molecules transcribed from all or a portion of a target coding sequence, thereby controlling the infection.

The present invention discloses nucleotide and amino acid sequences of the root knot plant nematode pests, *Meloidogyne* spp., from gene targets that are conserved and essential to the viability of the plant parasitic nematodes. This invention further describes the use of these sequences to modify the expression of one or more target polynucleotide or protein molecules in at least the cells of a *Meloidogyne* species by providing in its diet a dsRNA that comprises a part of, or all, or substantially all, of one or more polynucleotide molecules of the present invention. The high nucleotide conservation of these target root knot sequences facilitates the simultaneous targeting of multiple root knot nematode species with small numbers of dsRNA constructs while providing selectivity over similar or homologous human and plant sequences, and also provides selectivity over similar or homologous sequences present in other non-target organisms like beneficial insects (e.g., bees or butterflies).

An environmentally benign but effective alternative for controlling root knot nematodes is the use of RNA interference against essential nematode genes to control nematode infestation of plants. This is achieved through the transgenic expression of double stranded RNA (dsRNA) complementary to target nematode genes in plants. The complementarity of the dsRNA to a target gene may be perfect, i.e. 100%, in the sequence being targeted, or the sequence of the dsRNA may be substantially complementary, e.g. about 90% or 95% greater, along the sequence being targeted.

Therefore, the present invention relates to sequence-specific inhibition of expression of coding sequences using double-stranded RNA (dsRNA), including small interfering RNA (siRNA), to achieve the intended levels of root knot nematode control.

A method for inhibiting target gene function within the root knot nematodes, *Meloidogyne* spp, is also provided by the present invention, and can be accomplished by RNA interference, resulting in disruption of the pathogen's lifecycle. Optimal target genes for disruption include life-cycle essential genes where disruption results in high penetrance death of the parasite populations or "genetic death" by blocking of reproduction with minimal feeding damage to the plant, reduction in number of established feeding sites, minimizing the number of eggs produced, minimizing the viablility of the eggs, and minimizing the number of viable escaping worms reaching the next generation. In particular embodiments, efficacy (i.e. inhibition of a target gene function) may be assayed by comparing the number of eggs produced by *Meloidogyne* nematodes subjected to the methods and compositions of the present invention, versus the number of eggs produced by *Meloidogyne* nematodes grown under similar conditions but not subjected to such methods and/or compositions. Another aspect of the present invention provides nucleic acids of target genes predicted to be essential to *Meloidogyne* spp. growth, and/or development, such as feeding or production of eggs. Features used to predict such targets include orthology to known *C. elegans* genes with strong and reproducible RNA interference phenotypes, orthology to RNAi validated genes in *H. glycines* (soybean cyst nematode) and expression pattern in *Meloidogyne* spp.

In yet another aspect of the present invention, a set of isolated and purified nucleotide sequences as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 through SEQ ID NO:30, SEQ ID NO:32, SEQ ID NO:40, SEQ ID NO:42, SEQ ID NO:44, SEQ ID NO:46, or SEQ ID NO:47, or a complement thereof, is provided. The present invention also provides a stabilized dsRNA molecule for the expression of one or more RNAs for inhibition of expression of a target gene in a plant-parasitic nematode, expressed from these sequences and fragments thereof. A stabilized dsRNA, including a dsRNA or siRNA molecule can comprise at least two transcribed sequences, e.g. coding sequences that are arranged in a sense and an antisense orientation relative to at least one promoter, wherein the nucleotide sequence that comprises a sense strand and an antisense strand are linked or connected by a spacer sequence of at least from about one to about one thousand nucleotides, wherein the sense strand and the antisense strand may be a different length, and wherein each of the two transcribed sequences shares at least 80% sequence identity, at least 90%, at least 95%, at least 98%, at least 99%, or 100% sequence identity, to any one or more nucleotide sequence(s) set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 through SEQ ID NO:30, SEQ ID NO:32, SEQ ID NO:40, SEQ ID NO:42, SEQ ID NO:44, SEQ ID NO:46, or SEQ ID NO:47, or a complement thereof.

In yet another aspect, the invention provides recombinant DNA constructs comprising a nucleic acid molecule encoding a dsRNA molecule described herein. The dsRNA may be formed by transcription of one strand of the dsRNA molecule from a nucleotide sequence which is at least from about 80% to about 100% identical to a nucleotide sequence selected from the group consisting of: a fragment of at least 21 contiguous nucleotides, up to the full length, of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 through SEQ ID NO:30, SEQ ID NO:32, SEQ ID NO:40, SEQ ID NO:42, SEQ ID NO:44, SEQ ID NO:46, and SEQ ID NO:47, and a complement thereof. Such recombinant DNA constructs may be defined as producing dsRNA molecules capable of inhibiting the expression of endogenous target gene(s) in a plant-parasitic nematode cell upon ingestion. The construct may comprise a nucleotide sequence of the invention operably linked to a promoter sequence that functions in the host cell such as a plant cell. Such a promoter may be tissue-specific and may, for example, be specific to a tissue type which is the subject of plant-parasitic nematode attack. In the case of a root or foliar pathogen, respectively for example, it may be desired to use a promoter providing root or leaf-preferred expression, respectively.

Nucleic acid constructs in accordance with the invention may comprise at least one non-naturally occurring nucleotide sequence that can be transcribed into a single stranded RNA capable of forming a dsRNA molecule in vivo through intermolecular or intramolecular hybridization. Such dsRNA sequences self assemble and can be provided in the nutrition source of a plant-parasitic nematode to achieve the desired inhibition.

A recombinant DNA construct may comprise one or more different non-naturally occurring sequences which, when expressed in vivo as dsRNA sequences and provided in the tissues of the host plant of a plant-parasitic nematode, inhibit the expression of at least two different target genes in the plant-parasitic nematode. In certain embodiments, at least 2, 3, 4, 5, 6, 8 or 10 or more different dsRNAs are produced in a cell, or plant comprising the cell, that have a nematode-inhibitory effect. The dsRNAs may be expressed from multiple constructs introduced in different transformation events or could be introduced on a single nucleic acid molecule. The dsRNAs may be expressed using a single promoter or multiple promoters. In one embodiment of the invention, single dsRNAs are produced that comprise nucleic acids homologous to multiple loci within a plant-parasitic nematode.

In still yet another aspect, the invention provides a recombinant host cell having in its genome at least one recombinant DNA sequence that is transcribed to produce at least one dsRNA molecule that functions when ingested by a plant-parasitic nematode to inhibit the expression of a target gene in the nematode. The dsRNA molecule may be encoded by any of the nucleic acids described herein and as set forth in the sequence listing. The present invention also provides a transformed plant cell having in its genome at least one recombinant DNA sequence described herein. Transgenic plants comprising such a transformed plant cell are also provided, including progeny plants of any generation, seeds, and plant products, each comprising the recombinant DNA. The dsRNA molecules of the present invention may be found in the transgenic plant cell, for instance in the cytoplasm. They may also be found in an apoplastic space.

Further provided by the invention is a fragment of a nucleic acid sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 through SEQ ID NO:30, SEQ ID NO:32, SEQ ID NO:40, SEQ ID NO:42, SEQ ID NO:44, SEQ ID NO:46, and SEQ ID NO:47, and complements thereof. The fragment may be defined as causing the death, growth inhibition, reduced reproduction, or cessation of infestation or feeding by a *Meloidogyne* nematode, when expressed as a dsRNA and taken up by the nematode. The fragment may, for example, comprise at least about 19, 21, 23, 25, 40, 60, 80, 100, 125, 200, 250, 300, 400 or more contiguous nucleotides of, including the full length of, any one or more of the sequences in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 through SEQ ID NO:30, SEQ ID NO:32, SEQ ID NO:40, SEQ ID NO:42, SEQ ID NO:44, SEQ ID NO:46, or SEQ ID NO:47, or a complement thereof. One example of a beneficial DNA segment for use in the present invention is at least from about 19 to about 23, or about 23 to about 100 nucleotides, but less than about 2000 nucleotides, in length. Particularly useful will be dsRNA sequences including about 23 to about 300 nucleotides homologous to a nematode target sequence, including 19, 21, 23, 25, 40, 60, 80, 100, 125, 200, 250, 300, 400 or more contiguous nucleotides. The invention also provides a ribonucleic acid expressed from any of such sequences including a dsRNA. A sequence selected for use in expression of a gene suppression agent can be constructed from a single sequence derived from one or more target plant-parasitic nematode species and intended for use in expression of an RNA that functions in the suppression of a single gene or gene family in the one or more target pathogens, or that the DNA sequence can be constructed as a chimera from a plurality of DNA sequences.

In another embodiment, the invention provides a method for modulating expression of a target gene in a nematode cell, such as a cell of a *Meloidogyne* spp., the method comprising: (a) transforming a plant cell with a vector comprising a nucleic acid sequence operatively linked to a promoter and a transcription termination sequence, wherein the nucleic acid sequence encodes a dsRNA; (b) culturing the transformed plant cell under conditions sufficient to allow for development of a plant cell culture comprising a plurality of transformed plant cells; (c) selecting for transformed plant cells that have integrated the vector into their genomes; (d) screening the transformed plant cells for expression of the dsRNA encoded by the vector; (e) selecting a plant cell that expresses the dsRNA; (f) optionally regenerating a plant from the plant cell that expresses the dsRNA; whereby expression of the nucleic acid sequence in the plant is sufficient to modulate the expression of a target gene in a cell of a plant parasitic nematode that contacts the transformed plant or plant cell. Modulation of gene expression may include partial or complete suppression of such expression.

In yet another aspect, the invention provides a method for suppression of gene expression in a plant-parasitic nematode, comprising the provision in the tissue of the host of the nematode a gene-suppressive amount of at least one dsRNA molecule transcribed from a nucleotide sequence as described herein, at least one segment of which is complementary to an mRNA sequence within the cells of the plant-parasitic nematode. The method may further comprise observing the death, growth inhibition, or reduced reproduction of the plant-parasitic nematode, and the degree of host symptomatology. A dsRNA molecule, including its modified form such as an siRNA molecule, ingested by a pathogenic microorganism in accordance with the invention may, in one embodiment, be at least from about 80, 81, 82, 83, 84, 85, 86, 87, 88 89, 90, 91, 92, 93, 94, 95, 96, 97, 98, 99, or about 100% identical to a RNA molecule transcribed from all or a portion of a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 through SEQ ID NO:30, SEQ ID NO:32, SEQ ID NO:40, SEQ ID NO:42, SEQ ID NO:44, SEQ ID NO:46, and SEQ ID NO:47.

Isolated and substantially purified nucleic acid molecules including, but not limited to, non-naturally occurring nucleotide sequences and recombinant DNA constructs for transcribing dsRNA molecules of the present invention are therefore provided, which suppress or inhibit the expression of an endogenous coding sequence or a target coding sequence in the plant-parasitic nematode when introduced thereto. Transgenic plants that (a) contain nucleotide sequences encoding the isolated and substantially purified nucleic acid molecules and the non-naturally occurring recombinant DNA constructs for transcribing the dsRNA molecules for controlling plant-parasitic nematode infections, and (b) display resistance and/or enhanced tolerance to the infections, are also contemplated. Compositions containing the dsRNA nucleotide sequences of the present invention for use in topical applications onto plants or onto animals or into the environment of an animal to achieve the elimination or reduction of plant-parasitic nematode infection are also included.

cDNA sequences encoding proteins or parts of proteins essential for survival, such as amino acid sequences involved in various metabolic or catabolic biochemical pathways, cell division, reproduction, energy metabolism, digestion, and the like may be selected for use in preparing double stranded RNA molecules to be provided in the host plant of a plant-parasitic nematode. As described herein, ingestion of compositions by a target organism containing one or more dsRNAs, at least one segment of which corresponds to at least a substantially identical segment of RNA produced in the cells of the target pathogen, can result in the death or other inhibition of the target organism. These results indicate that a nucleotide sequence, either DNA or RNA, derived from a plant-parasitic nematode can be used to construct plant cells resistant to infestation by the nematode. The host plant of the nematode, for example, can be transformed to contain one or more of the nucleotide sequences derived from the nematode as provided herein. The nucleotide sequence transformed into the host may encode one or more RNAs that form into a dsRNA sequence in the cells or biological fluids within the transformed host, thus making the dsRNA available if/when the plant-parasitic nematode forms a nutritional relationship with the transgenic host. This may result in the suppression of expression of one or more genes in the cells of the plant-parasitic *Meloidogyne* spp. nematode and ultimately death or inhibition of its growth, development, or reproduction.

The present invention relates generally to genetic control of plant-parasitic nematodes in host organisms. More particularly, the present invention includes methods for delivery of nematode control agents to plant-parasitic nematodes. Such control agents cause, directly or indirectly, an impairment in the ability of the plant-parasitic nematode to feed, grow or otherwise cause disease in a target host. The present invention provides in one embodiment a method comprising delivery of stabilized dsRNA molecules to plant-parasitic nematodes as a means for suppression of targeted genes in the plant-parasitic nematode, thus achieving desired control of plant disease in the nematode host.

In accomplishing the foregoing, the present invention provides a method of inhibiting expression of a target gene in a plant-parasitic nematode, resulting in the impairment of growth, development, reproduction, and/or feeding, and eventually may result in the death of the plant-parasitic nematode. The method comprises in one embodiment introducing partial or fully stabilized double-stranded RNA (dsRNA) nucleotide molecules, including its modified forms such as small interfering RNA (siRNA) sequences, into a nutritional composition for the plant-parasitic nematode, and making the nutritional composition or food source available to the plant-parasitic nematode. Ingestion of the nutritional composition containing the double stranded or siRNA molecules results in the uptake of the molecules by the cells of the nematode, resulting in the inhibition of expression of at least one target gene in the cells of the nematode Inhibition of the target gene exerts a deleterious effect upon the nematode. The methods and associated compositions may be used for limiting or eliminating infection or parasitization of a plant or plant cell by a nematode, in or on any host tissue or environment in which a the nematode is present by providing one or more compositions comprising the dsRNA molecules described herein in the host of the nematode.

In certain embodiments, dsRNA molecules provided by the invention comprise nucleotide sequences complementary to a sequence as set forth in any of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 through SEQ ID NO:30, SEQ ID NO:32, SEQ ID NO:40, SEQ ID NO:42, SEQ ID NO:44, SEQ ID NO:46, or SEQ ID NO:47, the inhibition of which in a plant-parasitic nematode results in the reduction or removal of a protein or nucleotide sequence agent that is essential for the nematode's growth and development, reproduction, or other biological function. The nucleotide sequence selected may exhibit from about 80% to about 100% sequence identity to one of the nucleotide sequences as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:40, SEQ ID NO:42, SEQ ID NO:44, SEQ ID NO:46, or SEQ ID NO:47, or a fragment of at least 21 contiguous nucleotides thereof, up to the full length of the sequence, including the complement thereof. In certain other embodiments, DNA sequences capable of coding for efficacious dsRNA molecules are selected from the group consisting of SEQ ID NO:27 through SEQ ID NO:30, SEQ ID NO:32, SEQ ID NO:46, and SEQ ID NO:47, or complement thereof. Such inhibition can be described as specific in that a nucleotide sequence from a portion of the target gene is chosen from which the inhibitory dsRNA or siRNA is transcribed. The method is effective in inhibiting the expression of at least one target gene and can be used to inhibit many different types of target genes in the plant-parasitic nematode.

The sequences identified as having a nematode-protective effect may be readily expressed as dsRNA molecules through the creation of appropriate expression constructs. For example, such sequences can be expressed as a hairpin and stem and loop structure by taking a first segment corresponding to a sequence selected from SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 through SEQ ID NO:30, SEQ ID NO:32, SEQ ID NO:40, SEQ ID NO:42, SEQ ID NO:44, SEQ ID NO:46, or SEQ ID NO:47, or a fragment thereof; linking this sequence to a second segment spacer region that is not homologous or complementary to the first segment; and linking this to a third segment that transcribes an RNA, wherein at least a portion of the third segment is substantially complementary to the first segment. Such a construct forms a stem and loop structure by hybridization of the first segment with the third segment and a loop structure forms comprising the second segment (WO94/01550, WO98/05770, US 2002/0048814A1, and US 2003/0018993A1). DsRNA may be generated for instance in the form of a double stranded structure such as a stem loop structure (e.g. hairpin), whereby production of siRNA targeted for a nematode sequence is enhanced by co-expression of a fragment of the targeted gene, for instance on an additional plant expressible cassette, that leads to enhanced siRNA production, or reduces methylation to prevent transcriptional gene silencing of the dsRNA hairpin promoter (e.g. WO05/019408).

Exemplary species of the *Meloidogyne* genus which are contemplated in this invention include *M. arenaria, M. chitwoodi, M. artiellia, M. fallax, M. hapla, M. javanica, M. incognita, M. microtyla, M. partityla, M. panyuensis,* and *M. paranaensis*. Other plant parasitic nematodes which can be found together with root knot nematode include *Globodera, Pratylenchus, Paratrichodorus, Radopholus, Hoplolaimus, Ditylenchus, Dolichodorus, Helicotylenchus, Hirschmanniella, Xiphinema, Rotylenchulus, Trichodorus, Tylenchorhynchus, Belonolaimus* and *Longidorus* among others.

The methods and compositions of the present invention may be applied to any monocot or dicot plant, depending on the pathogen (e.g. nematode) control desired. Exemplary plants protected by the present invention with root knot and other plant-parasitic nematodes species associated them include, but are not limited to, alfalfa: *Meloidogyne hapla, Meloidogyne incognita, Meloidogyne javanica, Ditylenchus dipsaci, Pratylenchus* spp., *Paratylenchus* spp., *Xiphinema* spp.; banana: *M. incognita, M. arenaria, M. javanica, Radopholus similis, Helicotylenchus multicinctus, Pratylenchus coffeae, Rotylenchulus reniformis*; beans and peas: *Meloidogyne* spp., *Heterodera* spp., *Belonolaimus* spp., *Helicotylenchus* spp., *Rotylenchulus reniformis, Paratrichodorus anemones, Trichodorus* spp.; cassava: *Meloidogyne* spp., *Rotylenchulus reniformis*; cereals: *Meloidogyne naasi* (barley, wheat, rye); chickpea: *Meloidogyne* spp., *Heterodera cajani, Rotylenchulus reniformis, Hoplolaimus seinhorsti, Pratylenchus* spp.; citrus: *Meloidogyne* spp., *Tylenchulus semipenetrans, Radopholus similis, Radopholus citrophilus, Hemicycliophora arenaria, Pratylenchus* spp., *Bolonolaimus longicaudatus, Trichodorus* spp., *Paratrichodorus* spp., *Xiphinema* spp.; clover: *Meloidogyne* spp., *Heterodera trifolii*; corn: *Meloidogyne incognita, Pratylenchus* spp., *Paratrichodorus minor, Longidorus* spp., *Hoplolaimus columbus*; cotton: *Meloidogyne incognita, Belonolaimus longicaudatus, Rotylenchulus reniformis, Hoplolaimus galeatus, Pratylenchus* spp., *Tylenchorhynchus* spp., *Paratrichodorus minor*; grapes: *Meloidogyne* spp., *Xiphinema* spp., *Pratylenchus vulnus, Tylenchulus semipenetrans, Rotylenchulus reniformis*; grasses: *Pratylenchus* spp., *Longidorus* spp., *Paratrichodorus christiei, Xiphinema* spp., *Ditylenchus* spp.; peanut: *Meloidogyne* hapla., *Meloidogyne arenaria, Pratylenchus* spp., *Criconemella* spp., *Belonolaimus longicaudatus*; pigeon pea: *Meloidogyne* spp., *Heterodera cajani, Rotylenchulus reniformis, Hoplolaimus seinhorsti, Pratylenchus* spp.; potato: *Meloidogyne* spp., *Globodera rostochiensis, Globodera pallida, Pratylenchus* spp., *Trichodorus primitives, Ditylenchus* spp., *Paratrichodorus* spp., *Nacobbus aberrans*; rice: *Meloidogyne* spp., *Aphelenchiodes besseyi, Ditylenchus angustus, Hirchmanniella* spp., *Heterodera oryzae*; small fruits: *Meloidogyne* spp.; *Pratylenchus* spp., *Xiphinema* spp., *Longidorus* spp., *Paratrichodorus christiei, Aphelenchoides* spp.; soybean: *Meloidogyne incognita, Meloidogyne javanica, Heterodera glycines, Belonolaimus* spp., *Hoplolaimus columbus*; sugar beet: *Meloidogyne* spp., *Heterodera schachtii, Ditylenchus dipsaci, Nacobbus*

*aberrans, Trichodorus* spp., *Longidorus* spp., *Paratrichodorus* spp.; sugar cane: *Meloidogyne* spp., *Pratylenchus* spp., *Radopholus* spp., *Heterodera* spp., *Hoplolaimus* spp., *Helicotylenchus* spp., *Scutellonema* spp., *Belonolaimus* spp., *Tylenchorhynchus* spp., *Xiphinema* spp., *Longidorus* spp., *Paratrichodorus* spp.; tobacco: *Meloidogyne* spp., *Pratylenchus* spp., *Tylenchorhynchus claytoni, Globodera tabacum, Trichodorus* spp., *Xiphinema americanum, Ditylenchus dipsaci, Paratrichodorus* spp.; and tomato: *Meloidogyne* spp., *Pratylenchus* spp.

The various aspects of this invention are especially useful for transgenic plants having nematode resistance activity that include, without limitation, corn, cereals, including wheat, barley, rye, and rice, potato, tomato, cucumber, pepper, clovers, legumes, including soybeans (*Glycine* sp.), peas and alfalfa, sugar cane, sugar beets, tobacco, carrot, cotton (*Gossypium* sp.), rapeseed (canola), sunflower, safflower, sorghum, strawberry, banana, turf, and ornamentals among others.

The invention also provides combinations of methods and compositions for controlling infection by plant-parasitic nematodes. One means provides a dsRNA method as described herein for protecting plants from plant-parasitic nematodes along with one or more chemical agents that exhibit features different from those exhibited by the dsRNA methods and compositions, and can interfere with nematode growth, development, or reproduction.

A. Nucleic Acid Compositions and Constructs

The invention provides recombinant DNA constructs for use in achieving stable transformation of particular host targets. Transformed host targets may express effective levels of preferred dsRNA or siRNA molecules from the recombinant DNA constructs. Pairs of isolated and purified nucleotide sequences may be provided from cDNA library and/or genomic library information. The pairs of nucleotide sequences may be derived from any nematode for use as thermal amplification primers to generate the dsRNA and siRNA molecules of the present invention.

As used herein, the term "nucleic acid" refers to a single or double-stranded polymer of deoxyribonucleotide or ribonucleotide bases read from the 5' to the 3' end. The "nucleic acid" may also optionally contain non-naturally occurring or altered nucleotide bases that permit correct read through by a polymerase and do not reduce expression of a polypeptide encoded by that nucleic acid. The term "nucleotide sequence" or "nucleic acid sequence" refers to both the sense and antisense strands of a nucleic acid as either individual single strands or in the duplex. The term "ribonucleic acid" (RNA) is inclusive of RNAi (inhibitory RNA), dsRNA (double stranded RNA), siRNA (small interfering RNA), shRNA (small hairpin RNA), mRNA (messenger RNA), miRNA (micro-RNA), tRNA (transfer RNA, whether charged or discharged with a corresponding acylated amino acid), and cRNA (complementary RNA) and the term "deoxyribonucleic acid" (DNA) is inclusive of cDNA and genomic DNA and DNA-RNA hybrids. The words "nucleic acid segment", "nucleotide sequence segment", or more generally "segment" will be understood by those in the art as a functional term that includes both genomic sequences, ribosomal RNA sequences, transfer RNA sequences, messenger RNA sequences, operon sequences and smaller engineered nucleotide sequences that express or may be adapted to express, proteins, polypeptides or peptides.

Provided according to the invention are nucleotide sequences, the expression of which results in an RNA sequence which is substantially homologous to all or part of an RNA molecule of a targeted gene in a plant-parasitic nematode that comprises an RNA sequence encoded by a nucleotide sequence within the genome of the nematode. Thus, after ingestion of the stabilized RNA sequence down-regulation of the nucleotide sequence of the target gene in the cells of the plant-parasitic nematode may be obtained resulting in a deleterious effect on the growth, viability, proliferation, or reproduction of the nematode.

As used herein, the term "substantially homologous" or "substantial homology", with reference to a nucleic acid sequence, includes a nucleotide sequence that hybridizes under stringent conditions to the coding sequence of any of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 through SEQ ID NO:30, SEQ ID NO:32, SEQ ID NO:40, SEQ ID NO:42, SEQ ID NO:44, SEQ ID NO:46, or SEQ ID NO:47, as set forth in the sequence listing, or the complements thereof. Sequences that hybridize under stringent conditions to any of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 through SEQ ID NO:30, SEQ ID NO:32, SEQ ID NO:40, SEQ ID NO:42, SEQ ID NO:44, SEQ ID NO:46, or SEQ ID NO:47, or a complement thereof, are those that allow an antiparallel alignment to take place between the two sequences, and the two sequences are then able, under stringent conditions, to form hydrogen bonds with corresponding bases on the opposite strand to form a duplex molecule that is sufficiently stable under conditions of appropriate stringency, including high stringency, to be detectable using methods well known in the art. Substantially homologous sequences have generally from about 70% to about 80% sequence identity, or more particularly from about 80% to about 85% sequence identity, or still more particularly from about 90% to about 95% sequence identity, to about 99% sequence identity, to the referent nucleotide sequences as set forth in any of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 through SEQ ID NO:30, SEQ ID NO:32, SEQ ID NO:40, SEQ ID NO:42, SEQ ID NO:44, SEQ ID NO:46, or SEQ ID NO:47, in the sequence listing, or the complements thereof.

As used herein, the term "ortholog" refers to a gene in two or more species that has evolved from a common ancestral nucleotide sequence, and may retain the same function in the two or more species.

As used herein, the term "sequence identity", "sequence similarity" or "homology" is used to describe sequence relationships between two or more nucleotide sequences. The percentage of "sequence identity" between two sequences is determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. A first nucleotide sequence when observed in the 5' to 3' direction is said to be a "complement" of, or complementary to, a second or reference nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

As used herein, a "comparison window" refers to a conceptual segment of at least 6 contiguous positions, usually about 50 to about 100, more usually about 100 to about 150, in which a sequence is compared to a reference sequence of the same number of contiguous positions after the two sequences are optimally aligned. The comparison window may comprise additions or deletions (i.e. gaps) of about 20% or less as compared to the reference sequence (which does not comprise additions or deletions) for optimal alignment of the two sequences Those skilled in the art should refer to the detailed methods used for sequence alignment in the Wisconsin Genetics Software Package Release 7.0, Genetics Computer Group, 575 Science Drive Madison, Wis., USA) or refer to Ausubel et al. (1998) for a detailed discussion of sequence analysis.

The present invention provides DNA sequences capable of being expressed as an RNA transcript in a cell or microorganism to inhibit target gene expression in a cell, tissue or organ of a plant-parasitic nematode. The sequences comprise a DNA molecule coding for one or more different nucleotide sequences, wherein each of the different nucleotide sequences comprises a sense nucleotide sequence and an antisense nucleotide sequence. The sequences may be connected by a spacer sequence coding for a portion of a dsRNA molecule of the present invention. The spacer sequence can constitute part of the sense nucleotide sequence or the antisense nucleotide sequence or an unrelated nucleotide sequence and forms within the dsRNA molecule between the sense and antisense sequences. The sense nucleotide sequence or the antisense nucleotide sequence is substantially identical to the nucleotide sequence of the target gene or a derivative thereof or a complementary sequence thereto. The dsDNA molecule may be placed operably under the control of a promoter sequence that functions in the cell, tissue or organ of the host expressing the dsDNA to produce dsRNA molecules. In certain embodiments, the DNA sequence may be derived from a nucleotide sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO: 27 through SEQ ID NO:30, SEQ ID NO:32, SEQ ID NO:40, SEQ ID NO:42, SEQ ID NO:44, SEQ ID NO:46, or SEQ ID NO:47, or a complement thereof, in the sequence listing.

The invention also provides a DNA sequence for expression in a cell of a plant that, upon expression of the DNA to RNA and ingestion by a plant-parasitic nematode achieves suppression of a target gene in a cell, tissue or organ of a plant-parasitic nematode. The dsRNA may comprise one or multiple structural gene sequences, wherein each of the structural gene sequences comprises a sense nucleotide sequence and an antisense nucleotide sequence that may be connected by a spacer sequence that forms a loop within the complementary and antisense sequences. The sense nucleotide sequence or the antisense nucleotide sequence is substantially identical to the nucleotide sequence of the target gene, derivative thereof, or sequence complementary thereto. The one or more structural gene sequences may be placed operably under the control of one or more promoter sequences, at least one of which is operable in the cell, tissue or organ of a prokaryotic or eukaryotic organism, particularly a plant cell. Methods to express a gene suppression molecule in plants are known (e.g. US Publication 2006/0200878 A1), and may be used to express a nucleotide sequence of the present invention.

A gene sequence or fragment for plant-parasitic nematode control according to the invention may be cloned between two tissue specific promoters, such as two root specific promoters which are operable in a transgenic plant cell and therein expressed to produce mRNA in the transgenic plant cell that form dsRNA molecules thereto. Examples of root specific promoters are known in the art (e.g. the nematode-induced RB7 promoter; U.S. Pat. No. 5,459,252; Opperman et al. 1994). The dsRNA molecules contained in plant tissues are ingested by a plant-parasitic nematode so that the intended suppression of the target gene expression is achieved.

The cauliflower mosaic virus 35S promoter, an archetypal strong promoter common in transgenic plant applications, or a related promoter such as the E35S or the FMV promoter, may be employed for driving nematode resistance genes, particularly for root knot nematodes (see Example 8). Promoters have also been identified that direct gene expression at nematode-induced feeding structures within a plant (e.g. Gheysen and Fenoll, 2002). Thus, a promoter identified from among genes that are reproducibly expressed in feeding sites may be utilized. Examples of genes up-regulated in feeding sites formed by nematodes include At10.1 expressed in root and shoot apical meristems (Mazarei et al. 2003), Hs1pro-1 (Thurau et al. 2003), AtSUC2 normally expressed in companion cells (Juergensen et al. 2003), At17.1 expressed in vascular tissues and root tips (Mazarei et al. 2004), FGAM synthase (phosphoribosylformyl-glycinamidine synthase) (Vaghchhipawala et al. 2004), and ABI3 (De Meutter et al. 2005), among others. Root knot giant cells have cell wall ingrowth morphology characteristic of transfer cells Therefore, gene expression in the phloem may also be suited for delivery of effector molecules into feeding sites.

A nucleotide sequence provided by the present invention may comprise an inverted repeat separated by a "spacer sequence." The spacer sequence may be a region comprising any sequence of nucleotides that facilitates secondary structure formation between each repeat, where this is required. In one embodiment of the present invention, the spacer sequence is part of the sense or antisense coding sequence for mRNA. The spacer sequence may alternatively comprise any combination of nucleotides or homologues thereof that are capable of being linked covalently to a nucleic acid molecule. The spacer sequence may comprise, for example, a sequence of nucleotides of at least about 10-100 nucleotides in length, or alternatively at least about 100-200 nucleotides in length, at least 200-400 about nucleotides in length, or at least about 400-500 nucleotides in length.

The nucleic acid molecules or fragments of the nucleic acid molecules or other nucleic acid molecules in the sequence listing are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the complement of another nucleic acid molecule if they exhibit complete complementarity. Two molecules are said to be "minimally complementary" if they can hybridize to one another with sufficient stability to permit them to remain annealed to one another under at least conventional "low-stringency" conditions. Similarly, the molecules are said to be complementary if they can hybridize to one another with sufficient stability to permit them to remain annealed to one another under conventional "high-stringency" conditions. Conventional stringency conditions are described by Sambrook, et al. (1989), and by Haymes et al. (1985).

Departures from complete complementarity are therefore permissible, as long as such departures do not completely preclude the capacity of the molecules to form a double-stranded structure. Thus, in order for a nucleic acid molecule or a fragment of the nucleic acid molecule to serve as a primer or probe it needs only be sufficiently complementary in sequence to be able to form a stable double-stranded structure under the particular solvent and salt concentrations employed.

Appropriate stringency conditions which promote DNA hybridization are, for example, for applications requiring high selectivity, with relatively low salt and/or high temperature conditions, such as provided by about 0.02 M to about 0.15 M NaCl at temperatures of about 50° C. to about 70° C. A high stringency condition, for example, is to wash the hybridization filter at least twice with high-stringency wash buffer (0.2×SSC or 1×SSC, 0.1% SDS, 65° C.). Other conditions, such as 6.0× sodium chloride/sodium citrate (SSC) at about 45° C., followed by a wash of 2.0×SSC at 50° C., are also known to those skilled in the art or can be found in Current Protocols in Molecular Biology (1989). For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. A nucleic acid for use in the present invention may specifically hybridize to one or more of nucleic acid molecules from a nematode or complements thereof under such conditions. In specific embodiments, a nucleic acid for use in the present invention will exhibit at least from about 80%, or at least from about 90%, or at least from about 95%, or at least from about 98%, or at least from about 99%, or even about 100% sequence identity with one or more nucleic acid molecules as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 through SEQ ID NO:30, SEQ ID NO:32, SEQ ID NO:40, SEQ ID NO:42, SEQ ID NO:44, SEQ ID NO:46, or SEQ ID NO:47, or a complement thereof, in the sequence listing.

Nucleic acids of the present invention may also be synthesized, either completely or in part, especially where it is desirable to provide plant-preferred sequences, by methods known in the art. Thus, all or a portion of the nucleic acids of the present invention may be synthesized using codons preferred by a selected host. Species-preferred codons may be determined, for example, from the codons used most frequently in the proteins expressed in a particular host species. Other modifications of the nucleotide sequences may result in mutants having slightly altered activity.

DsRNA or siRNA nucleotide sequences comprise double strands of polymerized ribonucleotide and may include modifications to either the phosphate-sugar backbone or the nucleoside. Modifications in RNA structure may be tailored to allow specific genetic inhibition. In one embodiment, the dsRNA molecules may be modified through an enzymatic process so that siRNA molecules may be generated. The siRNA can efficiently mediate the down-regulation effect for some target genes in some pathogens. This enzymatic process may be accomplished by utilizing an RNAse III enzyme or a DICER enzyme, present in the cells of an insect, a vertebrate animal, a fungus or a plant in the eukaryotic RNAi pathway (Elbashir et al., 2001; Hamilton and Baulcombe, 1999). This process may also utilize a recombinant DICER or RNAse III introduced into the cells of a target insect through recombinant DNA techniques that are readily known to the skilled in the art. Both the DICER enzyme and RNAse III, being naturally occurring in a pathogen or being made through recombinant DNA techniques, cleave larger dsRNA strands into smaller oligonucleotides. The DICER enzymes specifically cut the dsRNA molecules into siRNA pieces each of which is about 19-25 nucleotides in length while the RNAse III enzymes normally cleave the dsRNA molecules into 12-15 base-pair siRNA. The siRNA molecules produced by the either of the enzymes have 2 to 3 nucleotide 3' overhangs, and 5' phosphate and 3' hydroxyl termini. The siRNA molecules generated by RNAse III enzyme are the same as those produced by Dicer enzymes in the eukaryotic RNAi pathway and are hence then targeted and degraded by an inherent cellular RNA-degrading mechanism after they are subsequently unwound, separated into single-stranded RNA and hybridize with the RNA sequences transcribed by the target gene. This process results in the effective degradation or removal of the RNA sequence encoded by the nucleotide sequence of the target gene in the pathogen. The outcome is the silencing of a particularly targeted nucleotide sequence within the pathogen. Detailed descriptions of enzymatic processes can be found in Hannon (2002).

A nucleotide sequence of the present invention can be recorded on computer readable media. As used herein, "computer readable media" refers to any tangible medium of expression that can be read and accessed directly by a computer. Such media include, but are not limited to: magnetic storage media, such as floppy discs, hard disc, storage medium, and magnetic tape: optical storage media such as CD-ROM; electrical storage media such as RAM and ROM; optical character recognition formatted computer files, and hybrids of these categories such as magnetic/optical storage media. A skilled artisan can readily appreciate that any of the presently known computer readable mediums can be used to create a manufacture comprising computer readable medium having recorded thereon a nucleotide sequence of the present invention.

As used herein, "recorded" refers to a process for storing information on computer readable medium. A skilled artisan can readily adopt any of the presently known methods for recording information on computer readable medium to generate media comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII text file, stored in a database application, such as DB2, Sybase, Oracle, or the like. The skilled artisan can readily adapt any number of data processor structuring formats (e.g. text file or database) in order to obtain computer readable medium having recorded thereon the nucleotide sequence information of the present invention.

Computer software is publicly available which allows a skilled artisan to access sequence information provided in a computer readable medium. Software that implements the BLAST (Altschul et al., 1990) and BLAZE (Brutlag, et al., 1993) search algorithms on a Sybase system can be used to identify open reading frames (ORFs) within sequences such as the Unigenes and EST's that are provided herein and that contain homology to ORFs or proteins from other organisms. Such ORFs are protein-encoding fragments within the sequences of the present invention and are useful in producing commercially important proteins such as enzymes used in amino acid biosynthesis, metabolism, transcription, translation, RNA processing, nucleic acid and a protein degradation, protein modification, and DNA replication, restriction, modification, recombination, and repair.

The present invention further provides systems, particularly computer-based systems, which contain the sequence information described herein. Such systems are designed to identify commercially important fragments of the nucleic acid molecule of the present invention. As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based system are suitable for use in the present invention.

As used herein, "a target structural motif," or "target motif," refers to any rationally selected sequence or combination of sequences in which the sequences or sequence(s) are chosen based on a three-dimensional configuration that is formed upon the folding of the target motif. There are a variety of target motifs known in the art. Protein target motifs include, but are not limited to, enzymatic active sites and signal sequences. Nucleic acid target motifs include, but are not limited to, promoter sequences, cis elements, hairpin structures and inducible expression elements (protein binding sequences).

B. Recombinant Vectors and Host Cell Transformation

A recombinant DNA vector may, for example, be a linear or a closed circular plasmid. The vector system may be a single vector or plasmid or two or more vectors or plasmids that together contain the total DNA to be introduced into the genome of the bacterial host. In addition, a bacterial vector may be an expression vector. Nucleic acid molecules as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 through SEQ ID NO:30, SEQ ID NO:32, SEQ ID NO:40, SEQ ID NO:42, SEQ ID NO:44, SEQ ID NO:46, or SEQ ID NO:47, or complements or fragments thereof, can, for example, be suitably inserted into a vector under the control of a suitable promoter that functions in one or more microbial hosts to drive expression of a linked coding sequence or other DNA sequence. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more selectable marker genes, and an inducible promoter allowing the expression of exogenous DNA.

Expression and cloning vectors generally contain a selection gene, also referred to as a selectable marker. This gene encodes a protein necessary for the survival or growth of transformed host cells grown in a selective culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. Those cells that are successfully transformed with a heterologous protein or fragment thereof produce a protein conferring drug resistance and thus survive the selection regimen.

An expression vector for producing a mRNA can also contain an inducible promoter that is recognized by a host bacterial organism and is operably linked to the nucleic acid. Inducible promoters suitable for use with bacterial hosts include β-lactamase promoter, $E.$ $coli$ λ phage PL and PR promoters, and $E.$ $coli$ galactose promoter, arabinose promoter, alkaline phosphatase promoter, tryptophan (trp) promoter, and the lactose operon promoter and variations thereof and hybrid promoters such as the tac promoter. However, other known bacterial inducible promoters are suitable.

The term "operably linked", as used in reference to a regulatory sequence and a structural nucleotide sequence, means that the regulatory sequence causes regulated expression of the linked structural nucleotide sequence. "Regulatory sequences" or "control elements" refer to nucleotide sequences located upstream (5' noncoding sequences), within, or downstream (3' non-translated sequences) of a structural nucleotide sequence, and which influence the timing and level or amount of transcription, RNA processing or stability, or translation of the associated structural nucleotide sequence. Regulatory sequences may include promoters, translation leader sequences, introns, enhancers, stem-loop structures, repressor binding sequences, and polyadenylation recognition sequences and the like.

Construction of suitable vectors containing one or more of the above-listed components employs standard recombinant DNA techniques. Isolated plasmids or DNA fragments are cleaved, tailored, and re-ligated in the form desired to generate the plasmids required. Examples of available bacterial expression vectors include, but are not limited to, the multifunctional $E.$ $coli$ cloning and expression vectors such as Bluescript™ (Stratagene, La Jolla, Calif.), in which, for example, a nucleic acid, or fragment thereof may be ligated into the vector in frame with sequences for the amino-terminal Met and the subsequent 7 residues of β-galactosidase so that a hybrid protein is produced; pIN vectors (Van Heeke and Schuster, 1989); and the like.

The present invention also contemplates transformation of a nucleotide sequence of the present invention into a plant to achieve nematode-inhibitory levels of expression of one or more dsRNA molecules. A transformation vector can be readily prepared using methods available in the art. The transformation vector comprises one or more nucleotide sequences that is/are capable of being transcribed to an RNA molecule and that is/are substantially homologous and/or complementary to one or more nucleotide sequences encoded by the genome of the target nematode, such that upon uptake of the RNA transcribed from the one or more nucleotide sequences by the target plant-parasitic nematode, there is down-regulation of expression of at least one of the respective nucleotide sequences of the genome of the nematode.

The transformation vector may be termed a dsDNA construct and may also be defined as a recombinant molecule, a disease control agent, a genetic molecule or a chimeric genetic construct. A chimeric genetic construct of the present invention may comprise, for example, nucleotide sequences encoding one or more antisense transcripts, one or more sense transcripts, one or more of each of the aforementioned, wherein all or part of a transcript there from is homologous to all or part of an RNA molecule comprising an RNA sequence encoded by a nucleotide sequence within the genome of a pathogen.

In one embodiment a plant transformation vector comprises an isolated and purified DNA molecule comprising a heterologous promoter operatively linked to one or more nucleotide sequences of the present invention. The nucleotide sequence is selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 through SEQ ID NO:30, SEQ ID NO:32, SEQ ID NO:40, SEQ ID NO:42, SEQ ID NO:44, SEQ ID NO:46, and SEQ ID NO:47, and complements thereof, as set forth in the sequence listing. The nucleotide sequence includes a segment coding all or part of an RNA present within a targeted nematode RNA transcript and may comprise inverted repeats of all or a part of a targeted nematode RNA. The DNA molecule comprising the expression vector may also contain a functional intron sequence positioned either upstream of the coding sequence or even within the coding sequence, and may also contain a five prime (5') untranslated leader sequence (i.e., a UTR or 5'-UTR) positioned between the promoter and the point of translation initiation.

A plant transformation vector may contain sequences from more than one gene, thus allowing production of more than one dsRNA for inhibiting expression of two or more genes in cells of a target nematode. One skilled in the art will readily appreciate that segments of DNA whose sequence corresponds to that present in different genes can be combined into a single composite DNA segment for expression in a transgenic plant. Alternatively, a plasmid of the present invention already containing at least one DNA segment can be modified by the sequential insertion of additional DNA segments between the enhancer and promoter and terminator sequences. In the disease control agent of the present invention designed for the inhibition of multiple genes, the genes to be inhibited can be obtained from the same plant-parasitic nematode species in order to enhance the effectiveness of the control agent. In certain embodiments, the genes can be derived from different plant-parasitic nematodes in order to broaden the range of nematodes against which the agent(s) is/are effective. When multiple genes are targeted for suppression or a combination of expression and suppression, a polycistronic DNA element can be fabricated as illustrated and disclosed in US Publication No. US 2004-0029283.

Promoters that function in different plant species are also well known in the art. Promoters useful for expression of polypeptides in plants include those that are inducible, viral, synthetic, or constitutive as described in Odell et al. (1985), and/or promoters that are temporally regulated, spatially regulated, and spatio-temporally regulated. Promoters that may find use with the invention include the enhanced CaMV35S promoters, and the FMV35S promoter. A fragment of the CaMV35S promoter exhibiting root-specificity may also be beneficially used. For the purpose of the present invention, it may be desired to achieve the highest levels of expression of these genes within the root tissues of plants. A number of root-specific promoters have been identified and are known in the art (e.g. U.S. Pat. Nos. 5,110,732; 5,837,848; 5,459,252; Hirel et al. 1992).

A recombinant DNA vector or construct of the present invention may comprise a selectable marker that confers a selectable phenotype on plant cells. Selectable markers may also be used to select for plants or plant cells that contain the exogenous nucleic acids encoding polypeptides or proteins of the present invention. The marker may encode biocide resistance, antibiotic resistance (e.g., kanamycin, G418 bleomycin, hygromycin, etc.), or herbicide resistance (e.g., glyphosate, etc.). Examples of selectable markers include, but are not limited to, a neo gene which codes for kanamycin resistance and can be selected for using kanamycin, G418, etc., a bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulfonylurea resistance; and a methotrexate resistant DHFR gene. Multiple selectable markers are available that confer resistance to ampicillin, bleomycin, chloramphenicol, gentamycin, hygromycin, kanamycin, lincomycin, methotrexate, phosphinothricin, puromycin, spectinomycin, rifampicin, and tetracycline, and the like. Examples of such selectable markers are illustrated in U.S. Pat. Nos. 5,550,318; 5,633,435; 5,780,708 and 6,118,047.

A recombinant vector or construct of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson et al., 1987); one or more of the various fluorescent proteins (FP) genes such as green fluorescent protein (GFP), red fluorescent protein (RFP) or any one of a large family of proteins which typically fluoresce at a characteristic wavelength; an R-locus gene, which encodes a product that regulates the production of anthocyanin pigments (red color) in plant tissues (Dellaporta et al., 1988); a β-lactamase gene (Sutcliffe et al., 1978), a gene which encodes an enzyme for which various chromogenic substrates are known (e.g., PADAC, a chromogenic cephalosporin); a luciferase gene (Ow et al., 1986) a xylE gene (Zukowski et al., 1983) which encodes a catechol dioxygenase that can convert chromogenic catechols; an α-amylase gene (Ikatu et al., 1990); a tyrosinase gene (Katz et al., 1983) which encodes an enzyme capable of oxidizing tyrosine to DOPA and dopaquinone which in turn condenses to melanin; an α-galactosidase, which catalyzes a chromogenic α-galactose substrate.

Examples of plant transformation vectors include those derived from a Ti plasmid of *Agrobacterium tumefaciens* (e.g. U.S. Pat. Nos. 4,536,475, 4,693,977, 4,886,937, 5,501,967 and EP 0 122 791). *Agrobacterium rhizogenes* plasmids (or "Ri") are also useful and known in the art. Other plant transformation vectors include those disclosed, e.g., by Herrera-Estrella (1983); Bevan (1983), Klee (1985) and EP 0 120 516.

In general it may be desired to introduce a functional recombinant DNA at a non-specific location in a plant genome. In special cases it may be useful to insert a recombinant DNA construct by site-specific integration. Several site-specific recombination systems exist which are known to function in plants include cre-lox as disclosed in U.S. Pat. No. 4,959,317 and FLP-FRT as disclosed in U.S. Pat. No. 5,527, 695.

Suitable methods for transformation of host cells for use with the current invention are believed to include virtually any method by which DNA can be introduced into a cell (see, for example, Mild et al., 1993), such as by transformation of protoplasts (U.S. Pat. No. 5,508,184; Omirulleh et al., 1993), by desiccation/inhibition-mediated DNA uptake (Potrykus et al., 1985), by electroporation (U.S. Pat. No. 5,384,253), by agitation with silicon carbide fibers (Kaeppler et al., 1990; U.S. Pat. No. 5,302,523; and U.S. Pat. No. 5,464,765), by Agrobacterium-mediated transformation (U.S. Pat. Nos. 5,563,055; 5,591,616; 5,693,512; 5,824,877; 5,981,840; 6,384,301) and by acceleration of DNA coated particles (U.S. Pat. Nos. 5,015,580; 5,550,318; 5,538,880; 6,160,208; 6,399, 861; 6,403,865; Padgette et al. 1995), etc. Through the application of techniques such as these, the cells of virtually any species may be stably transformed. In the case of multicellular species, the transgenic cells may be regenerated into transgenic organisms.

The most widely utilized method for introducing an expression vector into plants is based on the natural transformation system of Agrobacterium (for example, Horsch et al., 1985). A. tumefaciens and A. rhizogenes are plant pathogenic soil bacteria which genetically transform plant cells. The Ti and Ri plasmids of A. tumefaciens and A. rhizogenes, respectively, carry genes responsible for genetic transformation of the plant. Descriptions of Agrobacterium vector systems and methods for Agrobacterium-mediated gene transfer are provided by numerous references, including Gruber et al. 1993; Mild et al., 1993, Moloney et al., 1989, and U.S. Pat. Nos. 4,940,838 and 5,464,763. Other bacteria such as Sinorhizobium, Rhizobium, and Mesorhizobium that interact with plants naturally can be modified to mediate gene transfer to a number of diverse plants. These plant-associated symbiotic bacteria can be made competent for gene transfer by acquisition of both a disarmed Ti plasmid and a suitable binary vector (Broothaerts et al., 2005).

Methods for the creation of transgenic plants and expression of heterologous nucleic acids in plants in particular are known and may be used with the nucleic acids provided herein to prepare transgenic plants that exhibit reduced susceptibility to feeding by a target nematode. Plant transformation vectors can be prepared, for example, by inserting the dsRNA producing nucleic acids disclosed herein into plant transformation vectors and introducing these into plants. One known vector system has been derived by modifying the natural gene transfer system of Agrobacterium tumefaciens. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In the modified binary vectors the tumor-inducing genes have been deleted and the functions of the vir region are utilized to transfer foreign DNA bordered by the T-DNA border sequences. The T-region may also contain a selectable marker for efficient recovery of transgenic plants and cells, and a multiple cloning site for inserting sequences for transfer such as a dsRNA encoding nucleic acid.

A transgenic plant formed using Agrobacterium transformation methods typically may contain a single simple recombinant DNA sequence inserted into one chromosome, referred to as a transgenic event. Such transgenic plants can be referred to as being heterozygous for the inserted exogenous sequence. A transgenic plant homozygous with respect to a transgene can be obtained by sexually mating (selfing) an independent segregant transgenic plant that contains a single exogenous gene sequence to itself, for example an $F_0$ plant, to produce $F_1$ seed. One fourth of the $F_1$ seed produced will be homozygous with respect to the transgene. Germinating $F_1$ seed results in plants that can be tested for heterozygosity, typically using a SNP assay or a thermal amplification assay that allows for the distinction between heterozygotes and homozygotes (i.e., a zygosity assay). Crossing a heterozygous plant with itself or another heterozygous plant results in heterozygous progeny, as well as homozygous transgenic and homozygous null progeny.

C. Nucleic Acid Expression and Target Gene Suppression

The present invention provides, as an example, a transformed host plant of a pathogenic target organism, transformed plant cells and transformed plants and their progeny. The transformed plant cells and transformed plants may be engineered to express one or more of the dsRNA or siRNA sequences, under the control of a heterologous promoter, described herein to provide a pathogen-protective effect. These sequences may be used for gene suppression in a pathogen, thereby reducing the level or incidence of disease caused by the pathogen on a protected transformed host organism. As used herein the words "gene suppression" are intended to refer to any of the well-known methods for reducing the levels of protein produced as a result of gene transcription to mRNA and subsequent translation of the mRNA.

Gene suppression is also intended to mean the reduction of protein expression from a gene or a coding sequence including posttranscriptional gene suppression and transcriptional suppression. Posttranscriptional gene suppression is mediated by the homology between of all or a part of a mRNA transcribed from a gene or coding sequence targeted for suppression and the corresponding double stranded RNA used for suppression, and refers to the substantial and measurable reduction of the amount of available mRNA available in the cell for binding by ribosomes or the prevention of translation by the ribosomes. The transcribed RNA can be in the sense orientation to effect what is called co-suppression, in the anti-sense orientation to effect what is called anti-sense suppression, or in both orientations producing a dsRNA to effect what is called RNA interference (RNAi).

Transcriptional suppression is mediated by the presence in the cell of a dsRNA gene suppression agent exhibiting substantial sequence identity to a promoter DNA sequence or the complement thereof to effect what is referred to as promoter trans suppression. Gene suppression may be effective against a native plant gene associated with a trait, e.g., to result in plants with reduced levels of a protein encoded by the native gene or with enhanced or reduced levels of an affected metabolite. Gene suppression can also be effective against target genes in a plant-parasitic nematode that may ingest or contact plant material containing gene suppression agents, specifically designed to inhibit or suppress the expression of one or more homologous or complementary sequences in the cells of the nematode. Post-transcriptional gene suppression by anti-sense or sense oriented RNA to regulate gene expression in plant cells is disclosed in U.S. Pat. Nos. 5,107,065, 5,759,829, 5,283,184, and 5,231,020. The use of dsRNA to suppress genes in plants is disclosed in WO 99/53050, WO 99/49029, U.S. Publication No. 2003/017596, U.S. Patent Application Publication 2004/0029283.

A beneficial method of post transcriptional gene suppression versus a plant-parasitic nematode employs both sense-oriented and anti-sense-oriented, transcribed RNA which is stabilized, e.g., as a hairpin or stem and loop structure. An example of a DNA construct for effecting post transcriptional gene suppression is one in which a first segment encodes an RNA exhibiting an anti-sense orientation exhibiting substantial identity to a segment of a gene targeted for suppression, which is linked to a second segment encoding an RNA exhibiting substantial complementarity to the first segment. Such a construct forms a stem and loop structure by hybridization of the first segment with the second segment and a loop structure from the nucleotide sequences linking the two segments (see WO94/01550, WO98/05770, US 2002/0048814, and US 2003/0018993). Co-expression with an additional target gene segment may also be employed, as noted above (e.g. WO05/019408).

According to one embodiment of the present invention, there is provided a nucleotide sequence, for which in vitro expression results in transcription of a stabilized RNA sequence that is substantially homologous to an RNA molecule of a targeted gene in a plant-parasitic nematode that comprises an RNA sequence encoded by a nucleotide sequence within the genome of the nematode. Thus, after the plant-parasitic nematode ingests the stabilized RNA sequence, a down-regulation of the nucleotide sequence corresponding to the target gene in the cells of a target nematode is effected.

In certain embodiments of the invention, expression of a fragment of at least 21 contiguous nucleotides of a nucleic acid sequence of any of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO: 27 through SEQ ID NO:30, SEQ ID NO:32, SEQ ID NO:40, SEQ ID NO:42, SEQ ID NO:44, SEQ ID NO:46, or SEQ ID NO:47, or complements thereof, may be utilized, including expression of a fragment of up to 21, 36, 60, 100, 550, or 1000 contiguous nucleotides, or sequences displaying 90-100% identity with such sequences, or their complements. In specific embodiments, a nucleotide provided by the invention may comprise a sequence selected from the group described in Table 4, including a location on such sequence spanning nucleotides as described in Table 4. In yet other embodiments, a nucleotide provided by the invention may be described as comprising one or more of nucleotides 1-21, 22-50, 51-100, 101-150, 151-200, 201-250, 251-300, 301-350, 351-400, 401-450, 451-500, 501-550, 551-600, 601-650, 651-700, 701-750, 751-800, 801-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, 2001-2050, 2051-2100, 23-75, 76-125, 126-175, 176-225, 226-275, 276-325, 326-375, 376-425, 426-475, 476-525, 526-575, 576-625, 626-675, 676-725, 726-775, 776-825, 826-875, 876-925, 926-975, 976-1025, 1026-1075, 1076-1125, 1126-1175, 1176-1225, 1226-1275, 1276-1325, 1326-1375, 1376-1425, 1426-1475, 1476-1525, 1526-1575, 1576-1625, 1626-1675, 1676-1725, 1726-1775, 1776-1825, 1826-1875, 1876-1925, 1926-1975, 1976-2025, 2026-2075, 2076-2125, 1-550, 200-750, 300-850, 400-950, 500-1050, 600-1150, 700-1250, 800-1350, 900-1450, 1000-1550, 1100-1650, 1200-1750, 1300-1850, 1400-1950, 1500-2050, up to the full length of the sequence, of one or more of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 through SEQ ID NO:30, SEQ ID NO:32, SEQ ID NO:40, SEQ ID NO:42, SEQ ID NO:44, SEQ ID NO:46, or SEQ ID NO:47. Methods for selecting specific sub-sequences as targets for siRNA-mediated gene suppression are known in the art (e.g. Reynolds et al., 2004).

Inhibition of a target gene using the stabilized dsRNA technology of the present invention is sequence-specific in that nucleotide sequences corresponding to the duplex region of the RNA are targeted for genetic inhibition. RNA containing a nucleotide sequences identical to a portion of the target gene transcript may in certain embodiments be beneficial for inhibition. RNA sequences with insertions, deletions, and single point mutations relative to the target sequence have also been found to be effective for inhibition. In performance of specific embodiments of the present invention, the inhibitory dsRNA and the portion of the target gene may share at least from about 80% sequence identity, or from about 90% sequence identity, or from about 95% sequence identity, or from about 99% sequence identity, or even about 100% sequence identity. Alternatively, the duplex region of the RNA may be defined functionally as a nucleotide sequence that is capable of hybridizing with a portion of the target gene transcript. A less than full length sequence exhibiting a greater homology compensates for a longer less homologous sequence. The length of the identical nucleotide sequences may be at least about 25, 50, 100, 200, 300, 400, 500 or at least about 1000 bases. Normally, a sequence of greater than 20-100 nucleotides may be desired, though a sequence of greater than about 200-300 nucleotides, and a sequence of greater than about 500-1000 nucleotides may particularly provide benefit depending on the size of the target gene. In one embodiment the invention has the advantage of being able to tolerate sequence variations that might be expected due to genetic mutation, strain polymorphism, or evolutionary divergence. The introduced nucleic acid molecule may not need to be absolutely homologous to the target sequence, and it may not need to be full length relative to either the primary transcription product or fully processed mRNA of the target gene. Therefore, those skilled in the art need to realize that, as disclosed herein, 100% sequence identity between the RNA and the target gene is not required to practice the present invention.

Inhibition of target gene expression may be quantified by measuring either the endogenous target RNA or the protein produced by translation of the target RNA and the consequences of inhibition can be confirmed by examination of the outward properties of the cell or organism. Techniques for quantifying RNA and proteins are well known to one of ordinary skill in the art.

In certain embodiments gene expression is inhibited by at least 10%, at least 33%, at least 50%, or least 80%. In further embodiments of the invention, gene expression is inhibited by at least 80%, at least 90%, at least 95%, or by at least 99% within cells in the pathogen so a significant inhibition takes place. Significant inhibition is intended to refer to sufficient inhibition that results in a detectable phenotype (e.g., cessation of growth, feeding, development, reduced reproduction, mortality, etc.) or a detectable decrease in RNA and/or protein corresponding to the target gene being inhibited. Although in certain embodiments of the invention inhibition occurs in substantially all cells of the plant-parasitic nematode, in other embodiments inhibition occurs in only a subset of cells expressing the gene.

DsRNA molecules may be synthesized either in vivo or in vitro. The dsRNA may be formed by a single self-complementary RNA strand or from two complementary RNA strands. Endogenous RNA polymerase of the cell may mediate transcription in vivo, or cloned RNA polymerase can be used for transcription in vivo or in vitro Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus.

A RNA, dsRNA, siRNA, or miRNA of the present invention may be produced chemically or enzymatically by one skilled in the art through manual or automated reactions or in vivo in another organism. RNA may also be produced by partial or total organic synthesis; any modified ribonucleotide can be introduced by in vitro enzymatic or organic synthesis. The RNA may be synthesized by a cellular RNA polymerase or a bacteriophage RNA polymerase (e.g., T3, T7, SP6). The use and production of an expression construct are known in the art (see, for example, WO 97/32016; U.S. Pat. Nos. 5,593,874, 5,698,425, 5,712,135, 5,789,214, and 5,804,693). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

For transcription from a transgene in vivo or an expression construct, a regulatory region (e.g., promoter, enhancer, silencer, and polyadenylation) may be used to transcribe the RNA strand (or strands). Therefore, in one embodiment, the nucleotide sequences for use in producing RNA molecules may be operably linked to one or more promoter sequences functional in a microorganism, a fungus or a plant host cell. Ideally, the nucleotide sequences are placed under the control of an endogenous promoter, normally resident in the host genome. The nucleotide sequence of the present invention, under the control of an operably linked promoter sequence, may further be flanked by additional sequences that advantageously affect its transcription and/or the stability of a resulting transcript. Such sequences are generally located upstream of the operably linked promoter and/or downstream of the 3' end of the expression construct and may occur both upstream of the promoter and downstream of the 3' end of the expression construct, although such an upstream sequence only is also contemplated.

As used herein, the term "disease control agent", or "gene suppression agent" refers to a particular RNA molecule consisting of a first RNA segment and a second RNA segment linked by a third RNA segment. The first and the second RNA segments lie within the length of the RNA molecule and are substantially inverted repeats of each other and are linked together by the third RNA segment. The complementarity between the first and the second RNA segments results in the ability of the two segments to hybridize in vivo and in vitro to form a double stranded molecule, i.e., a stem, linked together at one end of each of the first and second segments by the third segment which forms a loop, so that the entire structure forms into a stem and loop structure, or even more tightly hybridizing structures may form into a stem-loop knotted structure. The first and the second segments correspond invariably, but not necessarily respectively, to a sense and an antisense sequence homologous with respect to the target RNA transcribed from the target gene in the target pathogen that is intended to be suppressed by the ingestion of the dsRNA molecule. The control agent can also be a substantially purified (or isolated) nucleic acid molecule and more specifically nucleic acid molecules or nucleic acid fragment molecules thereof from a genomic DNA (gDNA) or cDNA library. Alternatively, the fragments may comprise smaller oligonucleotides having from about 15 to about 250 nucleotide residues, and including about 15 to about 30 nucleotide residues.

As used herein, the term "genome" as it applies to cells of a plant-parasitic nematode or a host encompasses not only chromosomal DNA found within the nucleus, but organelle DNA found within subcellular components of the cell. The DNA's of the present invention introduced into plant cells can therefore be either chromosomally integrated or organelle-localized. The term "genome" as it applies to bacteria encompasses both the chromosome and plasmids within a bacterial host cell. The DNA's of the present invention introduced into bacterial host cells can therefore be either chromosomally integrated or plasmid-localized.

As used herein, the term "plant-parasitic nematode" refers to those nematodes that may infect, colonize, parasitize, or cause disease on host plant material transformed to express or coated with a double stranded gene suppression agent. As used herein, a "nematode resistance" trait is a characteristic of a transgenic plant, transgenic animal, or other transgenic host that causes the host to be resistant to attack from a nematode that typically is capable of inflicting damage or loss to the host. Such resistance can arise from a natural mutation or more typically from incorporation of recombinant DNA that confers plant-parasitic nematode resistance. To impart nematode resistance to a transgenic plant a recombinant DNA can, for example, be transcribed into a RNA molecule that forms a dsRNA molecule within the tissues or fluids of the recombinant plant. The dsRNA molecule is comprised in part of a segment of RNA that is identical to a corresponding RNA segment encoded from a DNA sequence within a plant-parasitic nematode that can cause disease on the host plant. Expression of the gene within the target plant-parasitic nematode is suppressed by the dsRNA, and the suppression of expression of the gene in the target plant-parasitic nematode results in the plant being resistant to the nematode.

The modulatory effect of dsRNA is applicable to a variety of genes expressed in the plant-parasitic nematode including, for example, endogenous genes responsible for cellular metabolism or cellular transformation, including housekeeping genes, transcription factors, molting-related genes, and other genes which encode polypeptides involved in cellular metabolism or normal growth and development.

As used herein, the phrase "inhibition of gene expression" or "inhibiting expression of a target gene in the cell of a plant-parasitic nematode" refers to the absence (or observable decrease in the level) of protein and/or mRNA product from the target gene. Specificity refers to the ability to inhibit the target gene without direct effects on other genes of the cell and without any direct effects on any gene within the cell that is producing the dsRNA molecule. The inhibition of gene expression of the target gene in the plant-parasitic nematode may result in novel phenotypic traits in the nematode.

The present invention provides in part a delivery system for the delivery of the nematode control agents by ingestion of host cells or the contents of the cells. In accordance with another embodiment, the present invention involves generating a transgenic plant cell or a plant that contains a recombinant DNA construct transcribing the stabilized dsRNA molecules of the present invention. As used herein, "taking up" refers to the process of an agent coming in contact with cells of a target organism, such as a nematode. This may occur, for instance, by nematode feeding, by soaking, or by injection. As used herein, the phrase "generating a transgenic plant cell or a plant" refers to the methods of employing the recombinant DNA technologies readily available in the art (e.g., by Sambrook, et al., 1989) to construct a plant transformation vector transcribing the stabilized dsRNA molecules of the present invention, to transform the plant cell or the plant and to generate the transgenic plant cell or the transgenic plant that contain the transcribed, stabilized dsRNA molecules.

It is envisioned that the compositions of the present invention can be incorporated within the seeds of a plant species either as a product of expression from a recombinant gene incorporated into a genome of the plant cells, or incorporated into a coating or seed treatment that is applied to the seed before planting. The plant cell containing a recombinant gene is considered herein to be a transgenic event.

The present invention provides in part a delivery system for the delivery of disease control agents to plant-parasitic nematodes. The stabilized dsRNA or siRNA molecules of the present invention may be directly introduced into the cells of a plant-parasitic nematode. Methods for introduction may include direct mixing of RNA with host tissue for the plant-parasitic nematode, as well as engineered approaches in which a species that is a host is engineered to express the dsRNA or siRNA. In one embodiment, the RNA may be sprayed onto a plant surface. In still another embodiment, the dsRNA or siRNA may be expressed by microorganisms and the microorganisms may be applied onto a plant surface or introduced into a root, stem by a physical means such as an injection. In still another embodiment, a plant may be genetically engineered to express the dsRNA or siRNA in an amount sufficient to kill the plant-parasitic nematodes known to infest the plant.

It is also anticipated that dsRNAs produced by chemical or enzymatic synthesis may be formulated in a manner consistent with common agricultural practices and used as spray-on products for controlling plant disease. The formulations may include the appropriate stickers and wetters required for efficient foliar coverage as well as UV protectants to protect dsRNAs from UV damage. Such additives are commonly used in the bioinsecticide industry and are well known to those skilled in the art. Such applications could be combined with other spray-on insecticide applications, biologically based or not, to enhance plant protection from plant-parasitic nematodes The present invention also relates to recombinant DNA constructs for expression in a microorganism. Exogenous nucleic acids from which an RNA of interest is transcribed can be introduced into a microbial host cell, such as a bacterial cell or a fungal cell, using methods known in the art.

The nucleotide sequences of the present invention may be introduced into a wide variety of prokaryotic and eukaryotic microorganism hosts to produce the stabilized dsRNA or siRNA molecules. The term "microorganism" includes prokaryotic and eukaryotic species such as bacteria and fungi, as well as nematodes. Fungi include yeasts and filamentous fungi, among others. Illustrative prokaryotes, both Gram-negative and Gram-positive, include Enterobacteriaceae, such as *Escherichia, Erwinia*, and *Serratia*; Bacillaceae; Rhizobiaceae, such as *Rhizobium*; Spirillaceae, such as *photobacterium, Zymomonas*; Lactobacillaceae; Pseudomonadaceae, such as *Pseudomonas* and *Acetobacter*; Azotobacteraceae, Actinomycetales, and Nitrobacteraceae. Among eukaryotes are fungi, such as Phycomycetes and Ascomycetes, including *Saccharomyces* and *Schizosaccharomyces*; and Basidiomycetes, such as *Rhodotorula, Aureobasidium*, and the like.

D. Transgenic Plants and Cells

Hairy roots are characterized by fast growth, frequent branching, plagiotropism. Hairy roots serve as a strong model for whole roots, as they retain the ability to synthesize compounds similarly to the roots of the intact plant (David et al. 1984). Methods for transfer and integration of the genes located on the root-inducing plasmid Ri of *Agrobacterium rhizogenes* into the plant genome and their expression therein are well established (White and Nester, 1980). These types of roots continue to grow in vitro on hormone-free medium and also exhibit a high degree of genetic stability (Aird et al. 1988). The natural ability of the soil bacterium *A. rhizogenes* to transform genes into a host plant genome results in roots being formed at the site of infection, and is used to produce hairy root cultures. Infection of the plant with *A. rhizogenes* strain R-1000, leads to the integration and expression of T-DNA in the plant genome, which causes development of a hairy roots. Hairy root cultures grow rapidly, show plagiotropic root growth and are highly branched on hormone-free medium. Transgenic hairy roots induced by *Agrobacterium rhizogenes* support the complete life cycle of root knot nematodes ("RKN"; *Meloidogyne* spp.) in vitro, and allow the rapid growth of tissue on a large scale which can be used for the identification and isolation of genes of interest. Hairy roots were initiated from soybean or tomato plants as described below, and in accordance with knowledge in the art.

The present invention provides seeds and plants having one or more transgenic events. Combinations of events are referred to as "stacked" transgenic events. These stacked transgenic events can be events that are directed at the same target organism, or they can be directed at different target pathogens or pests. In one embodiment, a seed having the ability to express a nucleic acid provided herein also has the ability to express at least one other agent, including, but not limited to, an RNA molecule the sequence of which is derived from the sequence of an RNA expressed in a target pathogen such as a nematode and that forms a double stranded RNA structure upon expressing in the seed or cells of a plant grown from the seed, wherein the ingestion of one or more cells of the plant by the target results in the suppression of expression of the RNA in the cells of the target.

In certain embodiments, a seed having the ability to express a dsRNA the sequence of which is derived from a target plant-parasitic nematode also has a "stacked" transgenic event that provides herbicide tolerance. One beneficial example of a herbicide tolerance gene provides resistance to glyphosate, N-(phosphonomethyl) glycine, including the isopropylamine salt form of such herbicide.

Benefits provided by the present invention may include, but are not limited to: the ease of introducing dsRNA into the plant-parasitic nematode cells, the low concentration of dsRNA which can be used, the stability of dsRNA, and the effectiveness of the inhibition. The ability to use a low concentration of a stabilized dsRNA avoids several disadvantages of anti-sense interference. The present invention is not limited to in vitro use or to specific sequence compositions, to a particular set of target genes, a particular portion of the target gene's nucleotide sequence, or a particular transgene or to a particular delivery method, as opposed to the some of the available techniques known in the art, such as antisense and co-suppression. Furthermore, genetic manipulation becomes possible in organisms that are not classical genetic models.

In order to achieve selective inhibition of a target gene within a plant-parasitic nematode species that it is desired to control, the target gene should generally exhibit a low degree of sequence identity with corresponding genes in a plant or a vertebrate animal. In specific embodiments the degree of the sequence identity is less than approximately 80%, including less than approximately 70%, and less than approximately 60%.

In addition to direct transformation of a plant with a recombinant DNA construct, transgenic plants can be prepared by crossing a first plant having a recombinant DNA construct with a second plant lacking the construct. For example, recombinant DNA for gene suppression can be introduced into first plant line that is amenable to transformation to produce a transgenic plant that can be crossed with a second plant line to introgress the recombinant DNA for gene suppression into the second plant line.

The present invention can be, in practice, combined with other disease control traits in a plant to achieve desired traits for enhanced control of plant disease. Combining disease control traits that employ distinct modes-of-action can provide protected transgenic plants with superior durability over plants harboring a single control trait because of the reduced probability that resistance will develop in the field.

The invention also relates to commodity products containing one or more of the sequences of the present invention, and produced from a recombinant plant or seed containing one or more of the nucleotide sequences of the present invention are specifically contemplated as embodiments of the present invention. A commodity product containing one or more of the sequences of the present invention is intended to include, but not be limited to, meals, oils, crushed or whole grains or seeds of a plant, or any food product comprising any meal, oil, or crushed or whole grain of a recombinant plant or seed containing one or more of the sequences of the present invention. The detection of one or more of the sequences of the present invention in one or more commodity or commodity products contemplated herein is defacto evidence that the commodity or commodity product is composed of a transgenic plant designed to express one or more of the nucleotides sequences of the present invention for the purpose of controlling plant disease using dsRNA mediated gene suppression methods.

E. Obtaining Nucleic Acids

The present invention provides methods for obtaining a nucleic acid comprising a nucleotide sequence for producing a dsRNA or siRNA. In one embodiment, such a method comprises: (a) analyzing one or more target gene(s) for their expression, function, and phenotype upon dsRNA-mediated gene suppression in a nematode; (b) probing a cDNA or gDNA library with a hybridization probe comprising all or a portion of a nucleotide sequence or a homolog thereof from a targeted nematode that displays an altered, e.g. reduced, nematode growth, development, or reproduction phenotype in a dsRNA-mediated suppression analysis; (c) identifying a DNA clone that hybridizes with the hybridization probe; (d) isolating the DNA clone identified in step (b); and (e) sequencing the cDNA or gDNA fragment that comprises the clone isolated in step (d) wherein the sequenced nucleic acid molecule transcribes all or a substantial portion of the RNA nucleotide acid sequence or a homolog thereof.

In another embodiment, a method of the present invention for obtaining a nucleic acid fragment comprising a nucleotide sequence for producing a substantial portion of a dsRNA or siRNA comprises: (a) synthesizing a first and a second oligonucleotide primers corresponding to a portion of one of the nucleotide sequences from a targeted pathogen; and (b) amplifying a cDNA or gDNA insert present in a cloning vector using the first and second oligonucleotide primers of step (a) wherein the amplified nucleic acid molecule transcribes a substantial portion of the a substantial portion of a dsRNA or siRNA of the present invention.

In practicing the present invention, a target gene may be derived from *M. incognita* or another nematode. It is contemplated that several criteria may be employed in the selection of target genes. The *Meloidogyne* spp. gene may be one which has a *C. elegans* ortholog with a high likelihood for a strong phenotype upon RNAi knockdown of expression, including a PO phenotype. Such targets are often those with protein products involved in core cellular processes such as DNA replication, cell cycle, transcription, RNA processing, translation, protein trafficking, secretion, protein modification, protein stability and degradation, energy production, intermediary metabolism, cell structure, signal transduction, channels and transporters, and endocytosis. In certain embodiments it is advantageous to select a gene for which a small drop in expression level results in deleterious effects for the pathogen. Of particular interest are *Meloidogyne* genes with RNAi validated orthologs in other tylenchid nematodes (e.g., soybean cyst nematode).

As used herein, the term "derived from" refers to a specified nucleotide sequence that may be obtained from a particular specified source or species, albeit not necessarily directly from that specified source or species.

In one embodiment, a gene is selected that is essentially involved in the growth, development, or reproduction of a plant-parasitic nematode. Other target genes for use in the present invention may include, for example, those that play important roles in nematode viability, growth, development, infectivity, and establishment of feeding sites. These target genes may be one of the house keeping genes, transcription factors and the like. Additionally, the nucleotide sequences for use in the present invention may also be derived from homologs, including orthologs, of plant, viral, bacterial or insect genes whose functions have been established from literature and the nucleotide sequences of which share substantial similarity with the target genes in the genome of a target nematode. According to one aspect of the present invention for nematode control, the target sequences may essentially be derived from the targeted plant-parasitic nematode. Some of the exemplary target sequences cloned from a nematode that encode proteins or fragments thereof which are homologues or orthologs of known proteins may be found in the Sequence Listing, for instance in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, and SEQ ID NO:25, SEQ ID NO:27, SEQ ID NO:28, SEQ ID NO:29, SEQ ID NO:30, SEQ ID NO:32, SEQ ID NO:40, SEQ ID NO:42, SEQ ID NO:44, SEQ ID NO:46, and SEQ ID NO:47.

For the purpose of the present invention, the dsRNA or siRNA molecules may be obtained by polymerase chain (PCR) amplification of a target gene sequences derived from a gDNA or cDNA library or portions thereof. The DNA library may be prepared using methods known to the ordinary skilled in the art and DNA/RNA may be extracted. Genomic DNA or cDNA libraries generated from a target organism may be used for PCR amplification for production of the dsRNA or siRNA.

The target gene sequences may be then be PCR amplified and sequenced using the methods readily available in the art. One skilled in the art may be able to modify the PCR conditions to ensure optimal PCR product formation. The confirmed PCR product may be used as a template for in vitro transcription to generate sense and antisense RNA with the included minimal promoters. In one embodiment, the present invention comprises isolated and purified nucleotide sequences that may be used as plant-parasitic nematode control agents. The isolated and purified nucleotide sequences may comprise those as set forth in the sequence listing.

As used herein, the phrase "coding sequence", "structural nucleotide sequence" or "structural nucleic acid molecule" refers to a nucleotide sequence that is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, genomic DNA, cDNA, EST and recombinant nucleotide sequences.

The term "recombinant DNA" or "recombinant nucleotide sequence" refers to DNA that contains a genetically engineered modification through manipulation via mutagenesis, restriction enzymes, and the like.

For many of the plant-parasitic nematodes that are potential targets for control by the present invention, there may be limited information regarding the sequences of most genes or the phenotype resulting from mutation of particular genes. Therefore, it is contemplated that selection of appropriate genes for use in the present invention may be accomplished through use of information available from study of the corresponding genes in a model organism such in *C. elegans*, in which the genes have been characterized, according to the analysis described in Examples 1-8. In some cases it will be possible to obtain the sequence of a corresponding gene from a target nematode by searching databases such as GenBank using either the name of the gene or the sequence from, for example, a nematode from which the gene has been cloned. Once the sequence is obtained, PCR may be used to amplify an appropriately selected segment of the gene in the target nematode for use in the present invention. PCR primers may be designed based on the sequence as found in another organism from which the gene has been cloned. The primers are designed to amplify a DNA segment of sufficient length for use in the present invention. DNA (either genomic DNA or cDNA) is prepared from the target plant-parasitic nematode, and the PCR primers are used to amplify the DNA segment. Amplification conditions are selected so that amplification will occur even if the primers do not exactly match the target sequence. Alternately, the gene (or a portion thereof) may be cloned from a gDNA or cDNA library prepared from a plant-parasitic nematode species, using the known gene as a probe. Techniques for performing PCR and cloning from libraries are known. Further details of the process by which DNA segments from target plant-parasitic nematodes species may be isolated based on the sequence of genes previously cloned from other species are provided in the Examples. One of ordinary skill in the art will recognize that a variety of techniques may be used to isolate gene segments from plant-parasitic nematodes that correspond to genes previously isolated from other species.

EXAMPLES

The inventors herein have identified a means for controlling plant-parasitic nematodes by providing double stranded ribonucleic acid molecules to plant-parasitic nematodes, and a means to select sequences that encode these double stranded ribonucleic acid molecules. Double stranded ribonucleic acid molecules that function upon ingestion to inhibit a biological function in a nematode may result, for example, in one or more of the following attributes: reduction in growth of a nematode, inhibition of development of a nematode, or reduction of viability or egg production. Any one or any combination of these attributes can result in an effective inhibition of plant infection or colonization, and in the case of a plant pathogenic nematode, inhibition of plant disease, and/or reduction in severity of disease symptoms.

Example 1

Hairy Root Generation Protocols

For soybean A3244 (susceptible) or P188788 (resistant) hairy roots, *A. rhizogenes* strain K599 (NCPPB 2659; NCPPB, Sand Hutton, York, UK) was grown and maintained on LB (Luria Bertani), or yeast extract and peptone (YEP) media. Yeast extract is the water-soluble portion of autolyzed yeast. The autolysis is carefully controlled to preserve naturally occurring B-complex vitamins. Yeast extract is typically prepared by growing baker's yeast, *Saccharomyces* spp., in a carbohydrate-rich plant medium. The yeast is harvested, washed, and resuspended in water, where it undergoes autolysis, i.e., self-digestion using the yeast's enzymes. Yeast extract is the total soluble portion of this autolytic action. The autolytic activity is stopped by a heating step. The resulting yeast extract is filtered clear and dried into a powder by spray drying. Methods for generation of transgenic tomato Mountain Spring (susceptible) or Fresh Mountain Plus (resistant) hairy root cultures using *A. rhizogenes* strain D1 are similar, except that MgL media containing yeast extract, NaCl, tryptone, L-glutamic acid, potassium phosphate, magnesium sulfate and biotin is used. Soybean seeds were surface-sterilized by contacting with chlorine gas under controlled conditions for 12-16 hours, followed by aeration in a clean air hood for at least 30 minutes. Seeds were germinated in Petri dishes containing ¼ MS (Murashige & Skoog, 1962). The hypocotyl or cotyledons of 6-day-old seedlings were wounded using a scalpel, and wounded cotyledons were then immersed in a culture of freshly grown *A. rhizogenes* containing a DNA construct of interest, and vacuum infiltrated. Cotyledons were cultured under similar conditions used for seed germination with the exception that the antibiotic cefotaxime is added to the ¼ MS agar plates to prevent subsequent overgrowth by *A. rhizogenes*. Adventitious roots were excised from hypocotyls or cotyledons inoculated with *A. rhizogenes*. The putative transformed roots were cultured on Gamborg's B-5 agar (Gamborg et al., 1976) containing 3% sucrose plus 3 g/l Gelrite®, BASTA, and cefotaxime). Roots surviving selection were transferred to fresh media and maintained on Gamborg's B-5 agar in an incubator, without light, at about 24-30° C. A piece of root tip was typically excised and transferred to fresh medium every 2-4 weeks.

Example 2

Nematode Bioassays on Hairy Root Material

Following hairy root line selection, roots for plant nematode bioassays were transferred to fresh plates containing Gamborg's B-5 medium and allowed to grow for approximately two weeks to provide sufficient tissue for nematode infection before inoculation with second-stage juveniles of root knot nematode (RKN). Individual hairy root tips were placed on infection plates. Typically, about 20 plates were used for pathogenicity testing of transformed roots for reaction to SCN or RKN. Each plate contained a transformed root from a separate integration. An additional 20 plates containing a transformed (empty vector) SCN-susceptible or RKN-susceptible control and an additional 20 plates containing a transformed SCN-resistant or RKN-resistant control were included in the tests. The protocol utilized was essentially that of Narayanan et al., 1999, with minor modifications. Plates were inoculated with approximately 450 sterile M. incognita J2s and incubated at 26-28° C. Approximately two weeks after inoculation with M. incognita, infected soybean hairy roots were removed from the agar plates and the number of galls was counted. Gall scores were weighted estimates based on size, in view of a rating scale as follows: the smallest galls were given a score of 1 and as the galled areas become larger the gall score increases. An example of the gall rating scale is shown in FIG. 2. The 1-4 scale was then used to rate each gall on each plate in the experiment.

Egg numbers were also scored at 42 days for RKN infections in tomato hairy roots (e.g. see Table 4). At 42 days post infection plates were microwaved and sieved to collect the roots. The roots were then blended in a 10% bleach solution and poured over a series of sieves to remove the root debris and collect the eggs. Eggs were removed from each plate and counted, and the roots were weighed.

Sterile SCN and RKN larvae were prepared for use with the hairy root culture system. Sterile SCN J2s were produced as follows: clean soybean cyst nematode eggs (i.e., eggs with soil and other debris removed) were collected and placed in a 50 ml centrifuge vial containing 30 ml of a 10% bleach solution. The bleach solution was mildly agitated and then left to settle for 2-3 minutes. The vial was mildly agitated again to re-suspend the eggs and then centrifuged for 1 minute at 1000 rpm. Under a sterile hood, the bleach solution was removed into a receptacle and 25 ml of sterile water is added into the vial of eggs. The vial was recapped under the sterile hood, mildly agitated to re-suspend the eggs and centrifuged for 1 minute at 1000 rpm. Under the sterile hood, this liquid was poured off and 25 ml of sterile water was again placed in the vial. The vial was recapped under the sterile hood and the process of agitation and centrifugation repeated. This process of washing the eggs with sterile water was repeated approximately 4 times to thoroughly rinse the bleach from the eggs. Following the last rinse under the sterile hood the liquid was removed leaving about 1-2 ml of egg concentrate. Sterilized eggs were hatched by incubating them on the surface of moist filter paper resting in a solution of 5 mM zinc sulfate just deep enough to cover the surface of the filter paper. After 2-3 days J2 larvae were collected in the solution underneath the filter paper. J2s are centrifuged and further sterilized using chlorhexidine (Atkinson et al., 1996).

Sterile RKN larvae were prepared by collecting eggs by placing chopped RKN infected roots into a blender with a sufficient quantity of 10% bleach solution. The blender was pulsed on/off for 5 second intervals. This process was repeated 5-6 times. The root slurry was then passed through a series of sieves where the eggs and small debris were collected in a 500 micron sieve. Any remaining bleach solution was thoroughly rinsed from this egg/debris. Twenty milliliters of the egg/debris was added to a 50 ml conical tube and 20 ml of a 40% sucrose solution was added into the bottom of the tube, bringing the total volume to 40 milliliters. This solution was then centrifuged at 3750 rpm for 5 minutes to separate the eggs from the debris. After centrifugation, the eggs were removed and thoroughly rinsed to remove any remaining sucrose solution. Eggs were then placed into a hatch bowl containing filter paper moistened with just enough aerated tap water to cover the eggs. After 1-2 days J2 larvae were collected in the solution underneath the filter paper. J2 larvae were centrifuged and further sterilized using chlorhexidine (Atkinson et al., 1996).

Example 3

Root Knot Nematode Target Genes Suitable for Broad Spectrum Control of Meloidogyne Species through RNA Interference Table 1 describes essential nematode gene nucleotide sequences (predicted or encoded polypeptides are listed in Table 2) with high nucleotide conservation that facilitate RNAi-based broad spectrum control of *Meloidogyne* spp. These sequences nonetheless have sufficient nucleotide divergence from essential genes in non-target organisms such as humans, the host plant and beneficial insects to reduce the likelihood of toxicity to these other organisms if exposed to the nematode dsRNAs.

To identify *M. incognita* orthologs of characterized *C. elegans* genes, homology searches were performed using the BLAST suite of programs (Altschul et al., 1990). Using predicted protein sequences for *C. elegans* genes (Wormpep) TBLASTN was used to search both *H. glycines* clustered ESTs and other sequences available from Genbank as well as recently generated proprietary genome survey sequences. Bitscore, e-value, and % identity were tracked. For consideration as a target, a *C. elegans* gene had to have a TBLASTN match to an ortholog or homolog in *M. incognita* with an e-value of at least e-10 or better. RKN genes having SCN RNAi positive orthologs were given high priority.

TABLE 1

| Nucleotide root knot nematode target sequences | | |
|---|---|---|
| SEQ ID NO: 1 | *M. incognita* top1 cDNA | 2238 nucleotide cDNA homolog of *C. elegans* M01E5.5b |
| SEQ ID NO: 3 | *M. incognita* let767 cDNA | 954 nucleotide cDNA homolog of *C. elegans* C56G2.6 |
| SEQ ID NO: 5 | *M. incognita* sec61a cDNA | 1422 nucleotide cDNA homolog of *C. elegans* Y57G11C.15 |
| SEQ ID NO: 7 | *M. incognita* transketolase cDNA | 1848 nucleotide cDNA homolog of *C. elegans* F01G10.1 |
| SEQ ID NO: 9 | *M. incognita* pas4 cDNA | 738 nucleotide cDNA homolog of *C. elegans* C36B1.4 |
| SEQ ID NO: 11 | *M. incognita* kin2 cDNA | 1119 nucleotide cDNA homolog of *C. elegans* R07E4.6 |
| SEQ ID NO: 13 | *M. incognita* cgh1 partial cDNA | 993 nucleotide partial cDNA homolog of *C. elegans* C07H6.5 |
| SEQ ID NO: 15 | *M. incognita* uba1 cDNA | 3222 nucleotide cDNA homolog of *C. elegans* C47E12.5 |
| SEQ ID NO: 17 | *M. incognita* vha13 cDNA | 1713 nucleotide cDNA homolog of *C. elegans* Y49A3A.2 |
| SEQ ID NO: 19 | *M. incognita* vha19 partial cDNA | 827 nucleotide partial cDNA homolog of *C. elegans* Y55H10A.1 |
| SEQ ID NO: 21 | *M. incognita* noah1 cDNA | 3507 nucleotide cDNA homolog of *C. elegans* C34G6.6 |

TABLE 1-continued

| | Nucleotide root knot nematode target sequences | |
|---|---|---|
| SEQ ID NO: 23 | *M. incognita* pas6 cDNA | 815 nucleotide mRNA homolog of *C. elegans* CD4.6 |
| SEQ ID NO: 25 | *M. incognita* T26G10.1 partial cDNA | 690 nucleotide partial cDNA homolog of *C. elegans* T26G10.1 |
| SEQ ID NO: 40 | *M. incognita* vha19 cDNA | 1008 nucleotide cDNA homolog of *C. elegans* Y55H10A.1 |
| SEQ ID NO: 42 | *M. incognita* T26G10.1 additional partial cDNA | 1102 nucleotide partial cDNA homolog of *C. elegans* T26G10.1 |
| SEQ ID NO: 44 | *M. incognita* vha15 partial cDNA | 261 nucleotide partial cDNA ortholog of *C. elegans* T14F9.1 |
| SEQ ID NO: 46 | *M. incognita* vha19 partial sequence | 705 nucleotide partial cDNA of *C. elegans* Y55H10A.1, with AscI/AsiSI restriction sites |

The sequences listed in Table 1 were compared to similar (e.g. orthologous or homologous) EST and other sequences in various *Meloidogyne* spp. as follows:

SEQ ID NO:1 comparison: *Meloidogyne* ESTs, *M. javanica* gb|BI324357.1| (98% identity, 1630-2138), *M. arenaria* gb|BI747188.1| (99% identity, 1687-2157), *M. hapla* gb|BM884829.1| (92% identity, 947-1461), *M. incognita* gb|BM882920.1| (98% identity, 1880-2131), *M. chitwoodi* gb|CB933476.1| (87%, 1707-2060; 94%, 2166-2239).

SEQ ID NO:3 comparison: *Meloidogyne* ESTs, *M. incognita* gb|CF980444.1| (99% identity, 1-662), *M. incognita* gb|CF980487.1| (98% identity, 24-654), *M. incognita* gb|CK984584.1| (94% identity, 1-662), *M. incognita* gb|CK984580.1| (94% identity, 1-692), *M. incognita* gb|CK984571.1| (94% identity, 1-691), *M. incognita* gb|CK984607.11 (95% identity, 1-633), *M. incognita* gb|CF980817.1| (94% identity, 1-633), *M. incognita* gb|CK983672.1| (95% identity, 44-626), *M. incognita* gb|CN443018.1| (95% identity, 33-611), *M. javanica* gb|BG736305.1| (97% identity, 222-725), *M. hapla* gb|CF803679.1| (88% identity, 1-645), *M. hapla* gb|CF803689.1| (88% identity, 1-644), *M. hapla* gb|CF803678.1| (88% identity, 1-645), *M. incognita* gb|CN443180.1| (90% identity, 1-519), *M. javanica* gb|BI745534.1| (95% identity, 277-477; 92% identity, 481-692).

SEQ ID NO:5 comparison: *Meloidogyne* ESTs, *M. arenaria* gb|CF357444.1| (99% identity, 1-552), *M. hapla* gb|CF357444.1| (92% identity, 892-1425), *M. hapla* gb|CN577502.1| (91% identity, 879-1425), *M. hapla* gb|BUO94011.1| (94% identity, 1-438), *M. arenaria* gb|BI747707.1| (100% identity, 1208-1425), *M. incognita* gb|AW829176.1| (92% identity, 662-879).

SEQ ID NO:7 comparison: *Meloidogyne* ESTs, *M. arenaria* gb|CF358371.1| (100% identity, 912-1520), *M. arenaria* gb|BI501616.1| (99% identity, 1324-1846), *M. arenaria* gb|BI746542.1| (96% identity, 1288-1848), *M. incognita* gb|AW829423.1| (96% identity, 1390-1851), *M. incognita* gb|AW871188.1| (96% identity, 1461-1851), *M. incognita* gb|CN443525.1| (98% identity, 1-256), *M. incognita* gb|CN443511.1| (98% identity, 1-256), *M. incognita* gb|CK984263.1| (98% identity, 1-256), *M. incognita* gb|CK984287.11 (98% identity, 1-256), *M. incognita* gb|CK984492.1| (96% identity, 1-256), *M. incognita* gb|CK984445.1| (96% identity, 1-256), *M. incognita* gb|CK984390.1| (96% identity, 1-256), *M. incognita* gb|CK984366.1| (96% identity, 1-256), *M. incognita* gb|BI703863.1| (96% identity, 1745-1851), *M. incognita* gb|BE239094.1| (96% identity, 1783-18549).

SEQ ID NO:9 comparison: *Meloidogyne* ESTs, *M. incognita* gb|CF099482.1| (99% identity, 1-678), *M. arenaria* gb|BI745992.1| (100% identity, 1-503), *M. arenaria* gb|BI863117.1| (99% identity, 1-452), *M. incognita* gb|BE239183.1| (99% identity, 351-741), *M. incognita* gb|BM880799.1| (99% identity, 147-504).

SEQ ID NO:11 comparison: *Meloidogyne* ESTs, collection of greater than 100 *M. incognita*, *M. javanica* and *M. arenaria* ESTs in the 3'-region 678-1122 of identity 98-100%.

SEQ ID NO:13 comparison: No detected *Meloidogyne* ESTs matches

SEQ ID NO:15 comparison: *Meloidogyne* ESTs, *M. arenaria* gb|BI745894.1| (97% identity, 2611-3101), *M. hapla* gb|BM883184.1| (91% identity, 2079-2556), *M. chitwoodi* gb|CB933531.1| (85% identity, 2472-2990), *M. hapla* gb|CN574157.1| (88% identity, 2827-3225).

SEQ ID NO:17 comparison: No detected *Meloidogyne* ESTs matches.

SEQ ID NO:19 comparison: *Meloidogyne* ESTs, *M. paranaensis* gb|CK426467.11 (99% identity, 61-714), *M. incognita* gb|BM880509.1| (99% identity, 248-789), *M. javanica* gb|BG736965.1| (96% identity, 243-746), *M. incognita* gb|BM881612.1| (99% identity, 370-827; 100% identity, 266-325), *M. javanica* gb|BG736194.1| (96% identity, 246-721), *M. javanica* gb|BG737132.1| (96% identity, 243-663), *M. incognita* gb|BM880760.1| (99% identity, 393-732; 100% identity, 259-392), *M. javanica* gb|BG736127.1| (96% identity, 243-600).

SEQ ID NO:21 comparison: *Meloidogyne* ESTs, *M. javanica* gb|BI744615.1| (98% identity, 300-700), *M. incognita* gb|CN443444.1| (100% identity, 1-237).

SEQ ID NO:23 comparison: *Meloidogyne* ESTs, *M. javanica* gb|BE578613.1| (97% identity, 1-606), *M. arenaria* gb|BI747271.1| (98% identity, 1-504), *M. incognita* gb|CD749365.1| (97% identity, 27-600), *M. javanica* gb|BI143067.1| (99% identity, 1-437), *M. hapla* gb|CF370648.1| (91% identity, 1-599), *M. hapla* gb|BM902290.1| (91% identity, 73-621), *M. hapla* gb|CN572891.1| (85% identity, 259-667).

SEQ ID NO:25 comparison: *Meloidogyne* ESTs, *M. incognita* gb|CD749648.1| (100% identity, 1-690), *M. incognita* gb|CF099489.1| (99% identity, 15-676), *M. arenaria* gb|BI746205.1| (97% identity, 203-644).

SEQ ID NO:40 comparison: *Meloidogyne* ESTs, *M. paranaensis* gb|CK426467.11 (98% identity, 130-783), *M. incognita* gb|BM880509.1| (99% identity, 317-858), *M. javanica* gb|BG736965.1| (96% identity, 312-815), *M. incognita* gb|BM881612.1| (90% identity, 325-896; 100% identity), *M. javanica* gb|BG736194.1| (96% identity, 315-790), *M. javanica* gb|BG737132.1| (96% identity, 312-732), *M. incognita* gb|BM880760.1| (90% identity, 328-801), *M. javanica* gb|BG736127.1| (95% identity, 312-669).

SEQ ID NO:42 comparison: *Meloidogyne* ESTs, *M. incognita* gb|CD749648.1| (99% identity, 1-675), *M. incognita* gb|CF099489.1| (99% identity, 1-661), *M. arenaria* gb|BI746205.1| (96% identity, 185-629).

SEQ ID NO:44 comparison: *Meloidogyne* ESTs, *M. javanica* gb|BG735889.1| (98%, 1-255), *M. javanica* gb|BG736205.1| (93%, 103-201).

Table 2 lists the predicted amino acid sequences encoded by the nucleotide sequences of Table 1.

TABLE 2

RKN amino acid sequences.

| | | |
|---|---|---|
| SEQ ID NO: 2 | *M. incognita* top1 ORF | 746 amino acid homolog of *C. elegans* M01E5.5b |
| SEQ ID NO: 4 | *M. incognita* let767 ORF | 318 amino acid homolog of *C. elegans* C56G2.6 |
| SEQ ID NO: 6 | *M. incognita* sec61a ORF | 474 amino acid homolog of *C. elegans* Y57G11C.15 |
| SEQ ID NO: 8 | *M. incognita* transketolase ORF | 616 amino acid homolog of *C. elegans* F01G10.1 |
| SEQ ID NO: 10 | *M. incognita* pas4 ORF | 246 amino acid homolog of *C. elegans* C36B1.4 |
| SEQ ID NO: 12 | *M. incognita* kin2 ORF | 373 amino acid homolog of *C. elegans* R07E4.6 |
| SEQ ID NO: 14 | *M. incognita* cgh1 partial ORF | 331 amino acid homolog of *C. elegans* C07H6.5 |
| SEQ ID NO: 16 | *M. incognita* uba1 ORF | 1074 amino acid homolog of *C. elegans* C47E12.5 |
| SEQ ID NO: 18 | *M. incognita* vha13 ORF | 571 amino acid homolog of *C. elegans* Y49A3A.2 |
| SEQ ID NO: 20 | *M. incognita* vha19 partial ORF | 275 amino acid homolog of *C. elegans* Y55H10A.1 |
| SEQ ID NO: 22 | *M. incognita* noah1 ORF | 1169 amino acid homolog of *C. elegans* C34G6.6 |
| SEQ ID NO: 24 | *M. incognita* pas6 ORF | 248 amino acid homolog of *C. elegans* CD4.6 |
| SEQ ID NO: 26 | *M. incognita* T26G10.1 partial ORF | 230 amino acid homolog of *C. elegans* T26G10.1 |
| SEQ ID NO: 41 | *M. incognita* vha19 ORF | 335 amino acid homolog of *C. elegans* Y55H10A.1 |
| SEQ ID NO: 43 | *M. incognita* T26G10.1additional partial cDNA | 367 amino acid homolog of *C. elegans* T26G10.1 |
| SEQ ID NO: 45 | *M. incognita* vha15 partial ORF | 87 amino acid fragment; ortholog of *C. elegans* T14F9.1 |

The amino acid sequences of Table 2 were compared with presumed orthologous or homologous amino acid sequences in various nematode species, as follows:

SEQ ID NO:2 has the following amino acid identity to its nematode orthologs, 71% *B. malayi*, 65% *C. elegans*, 66% *C. briggsae*.

SEQ ID NO:4 has the following amino acid identity to its nematode orthologs, 60% *H. glycines*, 47% *C. elegans*, 48% *C. briggsae*, 44% *B. malayi*.

SEQ ID NO:6 has the following amino acid identity to its nematode orthologs, 94% *B. malayi*, 93% *C. elegans*, 92% *C. briggsae*.

SEQ ID NO:8 has the following amino acid identity to its nematode orthologs, 62% *B. malayi*, 67% *C. elegans*, 66% *C. briggsae*.

SEQ ID NO:10 has the following amino acid identity to its nematode orthologs, 68% *B. malayi*, 69% *C. elegans*, 69% *C. briggsae*.

SEQ ID NO:12 has the following amino acid identity to its nematode orthologs, 78% *O. volvulus*, 78% *B. malayi*, 71% *C. elegans*, 75% *C. briggsae*.

SEQ ID NO:14 has the following amino acid identity to its nematode orthologs, 82% *B. malayi*, 83% *C. elegans*, 83% *C. briggsae*.

SEQ ID NO:16 has the following amino acid identity to its nematode orthologs, 58% *B. malayi*, 53% *C. elegans*, 55% *C. briggsae*.

SEQ ID NO:18 has the following amino acid identity to its nematode orthologs, 83% *B. malayi*, 86% *C. elegans*, 86% *C. briggsae*.

SEQ ID NO:20 has the following amino acid identity to its nematode orthologs, 22% *B. malayi*, 26% *C. elegans*, 22% *C. briggsae*.

SEQ ID NO:22 has the following amino acid identity to its nematode orthologs, 51% *B. malayi*, 49% *C. elegans*, 49% *C. briggsae*.

SEQ ID NO:24 has the following amino acid identity to its nematode orthologs, 54% *B. malayi*, 55% *C. elegans*, 55% *C. briggsae*.

SEQ ID NO:26 has the following amino acid identity to its nematode orthologs, 66% *B. malayi*, 66% *C. elegans*, 68% *C. briggsae*.

SEQ ID NO:41 has the following amino acid identity to its nematode orthologs: 28% *B. malayi*; 30% *C. elegans*; 27% *C. briggsae*.

SEQ ID NO:43 has the following amino acid identity to its nematode orthologs: 70% *B. malayi*; 69% *C. elegans*; 69% *C. briggsae*.

SEQ ID NO:45 has the following amino acid identity to its nematode orthologs: 77% *C. elegans*; 77% *C. briggsae*.

Example 4

DsRNA Sequences and Promoters for Gene Expression

Figure 1:
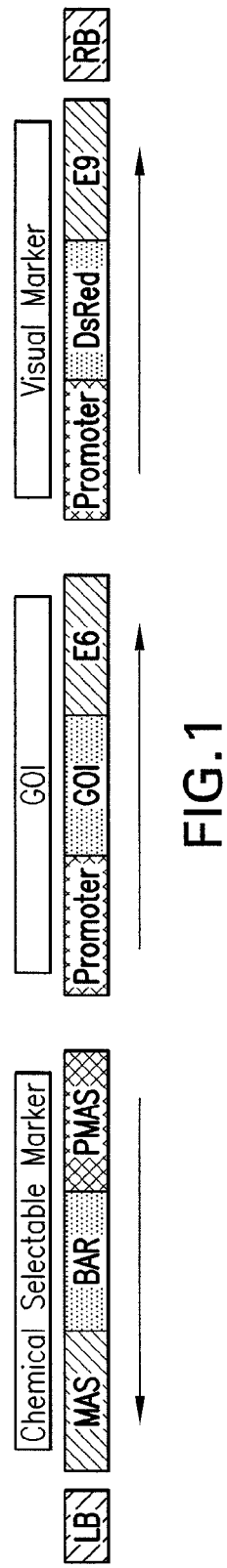
FIG. 1: shows a schematic example of a hairy root expression construct used to select for combined chemical (BASTA) and fluorescence (DsRed) to produce hairy roots with uniform expression of a nematicidal gene of interest (GOI). The GOI could encode a nematicidal nucleotide, such as a double stranded RNA (dsRNA) targeting an essential nematode gene. Kanamycin resistance is used for plasmid propagation within bacterial hosts. BASTA (ammonium glufosinate: phosphinothricin) tolerance is conferred by the expression of the BAR gene (phosphinothricin acetyltransferase) under the control of the mannopine synthase promoter and terminator.

FIG. 1 shows an exemplary schematic of a hairy root expression construct used to select for combined chemical (Basta®) and red fluorescence (DsRed marker; e.g. Clontech, Mountain View, Calif.) to produce hairy roots with uniform expression of a gene of interest (GOI) that targets survival, fitness or pathogenicity of a target nematode. The GOI could be a nematicidal nucleotide, protein or protein capable of producing a nematicidal agent (e.g., a metabolite), and is typically a double stranded RNA (dsRNA) targeting an essential nematode gene. Kanamycin resistance was used for plasmid propagation within bacterial hosts. Basta® (ammonium glufosinate:phosphinothricin) tolerance is conferred by the expression of the BAR gene (phosphinothricin acetyltransferase) under the control of the mannopine synthase promoter and terminator. The GOI can be driven by a strong constitutive promoter derived from the cauliflower mosaic virus 35S promoter (35S) or figwort mosaic virus (FMV) (e.g. SEQ ID NOs:36-39) or by one of a variety of plant promoters such as the ubiquitin 3 promoter, and terminators such as the E6, E9 or octopine synthase (OCS) terminator may be used. The red fluorescent protein DsRed (Matz et al., 1999) was typically expressed from a strong constitutive viral promoter or other promoter such as the *A. thaliana* phosphoglycerate mutase promoter (SEQ ID NO:35; Mazarei et al., 2003) with the use of a terminator such as E6, E9 or OCS.

TABLE 3

RKN dsRNA nucleotide sequences and promoter sequences.

| | | |
|---|---|---|
| SEQ ID NO: 27 | kin-2 dsRNA segment A | *M. incognita* homolog of *C. elegans* R07E4.6 |
| SEQ ID NO: 28 | kin-2 dsRNA segment B | *M. incognita* homolog of *C. elegans* R07E4.6 |
| SEQ ID NO: 29 | T26G10.1 dsRNA segment | *M. incognita* homolog of *C. elegans* T26G10.1 |
| SEQ ID NO: 30 | cgh1 dsRNA segment | *M. incognita* homolog of *C. elegans* C07H6.5 |
| SEQ ID NO: 31 | CM dsRNA segment | *M. incognita* chorismate mutase |
| SEQ ID NO: 32 | cathepsin L (CplA) dsRNA segment | *M. incognita* homolog of *C. elegans* T03E6.7 |
| SEQ ID NO: 33 | 16D10 dsRNA segment | *M. incognita* conserved secreted peptide |
| SEQ ID NO: 34 | Act7 intron | Intron from *A. thaliana* Act7 promoter |
| SEQ ID NO: 35 | Div10 promoter | D10.1 promoter from *A. thaliana* phosphoglycerate mutase gene (AY154746.1) |
| SEQ ID NO: 36 | FMV | Figwort mosaic virus promoter |
| SEQ ID NO: 37 | E35S | Enhanced cauliflower mosaic virus 35S promoter |
| SEQ ID NO: 38 | E35Sp | Enhanced cauliflower mosaic virus 35S promoter with the petunia translational leader |
| SEQ ID NO: 39 | 35SO | 35S promoter with the tobacco mosaic virus omega translational enhancer |
| SEQ ID NO: 47 | vha19 dsRNA segment | *M. incognita* homolog of *C. elegans* Y55H10A.1 |

A crop transformation base vector comprising selection expression cassettes and elements necessary for the maintenance of the plasmid in a bacteria cell was used to assemble DNA segments (promoters, leaders, introns, 3'UTR) that provide regulatory activity when operably linked to DNA segments that provide functionality in the present invention. The assembly of these DNA segments can be accomplished using methods well known in the art of recombinant DNA technology. Examples of DNA sequences capable of coding for efficacious dsRNA molecules are SEQ ID NO: 27 through 30, SEQ ID NO: 32, and SEQ ID NO:47 in table 3.

Example 5

Tomato Hairy Root Efficacy Against *M. incognita* Via Transgenic RNAi

Plates were inoculated with approximately 450 sterile *M. incognita* J2s and incubated at 26-28° C. At 42 days post infection plates were microwaved and sieved to collect the roots. The roots were then blended in a 10% bleach solution and poured over a series of sieves to remove the root debris and collect the eggs. Eggs were removed from each plate and counted, and the roots were weighed. Transgenic hairy root cultures were prepared expressing fragments of genes encoding, for instance, kin-2, T26G10.1, cgh 1, Cp1A, or Vha19 (e.g. SEQ ID NOs:27-30, SEQ ID NO:32, or SEQ ID NO:46), and these roots were tested for RKN resistance. Results are shown in Table 4, demonstrating efficacy in reducing RKN reproduction.

TABLE 4

Tomato hairy root efficacy of exemplary dsRNA constructs.

| P-GOI | 5'-Intron | DsRNA | P-DsRED | Test | % Egg Reduction |
|---|---|---|---|---|---|
| E35Sp | Act7 | Kin2A | FMV | 1 | 83* |
| E35Sp | Act7 | Cpl1A | FMV | 2 | 70* |
| E35Sp | Act7 | CM | FMV | 2 | 21 |
| E335p | Act7 | 16D10 | FMV | 2 | 75* |
| Div10 | | 16D10 | E35S | 2 | 34 |
| E335p | Act7 | Kin2A | FMV | 3 | 40 |
| Div10 | | Kin2A | E35S | 3 | 16 |
| Div10 | | Kin2B | E35S | 3 | 41 |
| E35Sp | Act7 | Kin2A | FMV | 4 | 59* |
| Div10 | | T26G10.1 | 35So | 4 | 51 |
| E35Sp | Act7 | Vha19 | FMV | 5 | 65 |
| E35Sp | Act7 | Vha19 | FMV | 6 | 63 |

TABLE 4-continued

Tomato hairy root efficacy of exemplary dsRNA constructs.

| P-GOI | 5'-Intron | DsRNA | P-DsRED | Test | % Egg Reduction |
|---|---|---|---|---|---|
| E35Sp | Act7 | T26G10.1 | FMV | 6 | 57 |
| E35Sp | Act7 | T26G10.1 | FMV | 7 | 63 |

*Statistically significant reduction relative to the susceptible control using a T test at 0.1 alpha.

Percent egg reduction is relative to the empty vector susceptible control. An enhanced cauliflower mosaic virus 35S promoter with or without the petunia leader 35S (E35S or E35Sp) SEQ ID NO 37 and SEQ ID NO 38, respectively, the figwort mosaic virus (FMV) promoter SEQ ID NO: 36, the D10.1 (Div10) promoter SEQ ID NO: 35, and the cauliflower mosaic virus 35S promoter with the tobacco mosaic virus omega translational enhancer SEQ ID NO: 39 were utilized.

The data in table 4 demonstrate that the promoter and target gene as well as the precise gene segment influence the degree of efficacy against RKN. Importantly it is possible to achieve high levels of efficacy against RKN using a transgenic RNAi approach targeted against gene targets disclosed herein.

Example 6

Transgenic Tobacco Whole Plant Generation and Assaying with *M. incognita* (RKN)

TABLE 5

Media components.

| MSO Medium | |
|---|---|
| MS salts + B5 vitamins | 4.4 g/L (e.g. from Phytotechnology Laboratories or Sigma) |
| Sucrose | 30 g/L |
| pH | to 5.7 with 1N KOH |
| difco-bacto type agar | 9.0 g/L |
| MS104 Medium: MSO (liquid) plus | |
| BAP | 1.0 mg/L |
| NAA | 0.1 mg/L |
| pH | to 5.7 with 1N KOH |
| difco-bacto type agar | 9.0 g/L |
| 4COO5K (liquid media) | |
| MS salts + B5 vitamins | 4.4 g/L |

TABLE 5-continued

Media components.

| | |
|---|---|
| pCPA | 4 mg/L |
| Sucrose | 30 g/L |
| pH | to 5.7 with 1N KOH |

Explants were prepared for pre-culture, e.g. by surface sterilizing leaves from one month old tobacco plants for 15 minutes in 10% Clorox with surfactant with 3× sterile DiH$_2$O washes. Leaves were cut into 0.5 cm pieces and 60-70 leaf pieces were placed upside down on MS104 plate with 2 mls 4C005K liquid media plus 2 sterile filter discs. This pre-culture was carried out for about 1-2 days. Then explants were inoculated using an overnight *Agrobacterium* culture that had been adjusted to 1.2×10$^9$ bac/ml with 4C005K (e.g. ~1/5 dilution). 2 mls adjusted *Agrobacterium* culture was added directly to each plate of pre-cultured explants, which were then incubated for 10 minutes. The *Agrobacterium* were pipetted off, leaving explants as dry as possible. Plates were blotted with sterile filter disc and allowed to co-culture for 2-3 days at 24° C. Explants were transferred to MS104 plus glufosinate 5 mg/L plus carbenicillin 500 µg/ml for selection phase by removing explants from filter paper and spacing them evenly onto selection plates (10-12 explants/plate).

At 4-6 weeks, shoots were cut from callus (one from each callus clump to ensure independent events) and placed on MS0 plus glufosinate plus carbenicillin 500 µg/ml rooting media. Callus that is not yet shooting may be cut into independent callus pieces and placed back on fresh MS104 selection plates to encourage shooting. Roots typically form on putative transformants in 7-10 days. At this time, small leaf pieces could be taken and recallused on MS104 selection plates to confirm kanamycin resistance if desired. Agar was rinsed carefully from the roots of rooted shoots, and plants were potted in small pots, watered well and placed under a propagation dome for 2-3 days. The lid of the dome can then be cracked gradually to harden off the seedlings to ambient conditions. These are referred to as R$_0$ plants.

Ten weeks after pots are put in the greenhouse the R$_1$ seed is ready to be harvested from the R$_0$ plant. Seeds from each R$_0$ plant are collected, planted, and allowed to grow for a week. The plants are then sprayed with 0.04% Finale® (glufosinate; Bayer CropScience) every day for a week. Plants that segregate in a 3:1 fashion are considered to have a single copy insertion and are kept for further analysis.

Twelve weeks after the R$_1$ seed is planted and selected, the R$_2$ seed is ready to be harvested from the R$_1$ plant. Seeds from the R$_1$ plant are collected, planted, and allowed to grow for a week. The plants are then sprayed with 0.04% Finale (glufosinate) every day for a week. Plants that segregate correctly (100% survival after Finale exposure) are considered to be homozygous and are kept for efficacy testing and seed collection. For each R$_2$ integration, a subset of the plants was infected with nematodes to determine efficacy and a subset was allowed to grow to produce the R$_3$ seed. Three weeks after the glufosinate selection of the R$_2$ plants, a subset of the plants was inoculated with 5000 vermiform eggs per pot of RKN J2s and scored for gall reduction 8 weeks later.

Twelve weeks after the glufosinate selection of the R$_2$ plants, a subset of plants are harvested for the R$_3$ seed. Subsequent generations such as R$_4$, R$_5$, etc. can be generated in similar fashion.

TABLE 6

Tobacco whole plant efficacy of exemplary dsRNA constructs.

| P-GOI | 5'-Intron | DsRNA | P-DsRED | Lines | Gall Reduction (%) |
|---|---|---|---|---|---|
| E35Sp | Act7 | Kin2A | FMV | Pool | 44* |
| E35Sp | Act7 | Kin2A | FMV | 1 | 34 |
| E35Sp | Act7 | Kin2A | FMV | 2 | 73* |
| E35Sp | Act7 | Kin2A | FMV | 3 | 38* |
| E35Sp | Act7 | Kin2A | FMV | 4 | 58* |
| E35Sp | Act7 | Kin2A | FMV | 5 | 16 |

*Statistically significant reduction relative to the susceptible control using a T test at 0.1 alpha.

The data in table 6 demonstrate that it is possible to achieve high levels of efficacy against RKN in the greenhouse using additional host plant species (i.e., tobacco in this case) using a transgenic RNAi approach targeted against gene targets disclosed herein.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

References

The following references are incorporated herein by reference:

U.S. Pat. Nos. 4,536,475; 4,693,977; 4,886,937; 4,940,838; 4,959,317; 5,015,580; 5,107,065; 5,110,732; 5,231,020; 5,283,184; 5,302,523; 5,384,253; 5,464,763; 5,464,765; 5,501,967; 5,508,184; 5,527,695; 5,538,880; 5,459,252; 5,550,318; 5,563,055; 5,591,616; 5,593,874; 5,633,435; 5,693,512; 5,698,425; 5,712,135; 5,759,829; 5,780,708; 5,789,214; 5,804,693; 5,824,877; 5,837,848; 5,981,840; 6,118,047; 6,160,208; 6,384,301; 6,399,861; 6,403,865.

U.S. Pub. 2002/0048814; U.S. Pub. 2003/0018993; U.S. Pub. 2003/0175965; U.S. Pub. 2004/0029283; US Pub. 2006/0200878 A1.

Aird et al., *Plant Cell Tiss. Org. Cult.* 15: 47-57, 1988.
Altschul et al., *J. Mol. Biol.,* 215:403-410, 1990.
Atkinson et al., *J. Nematol.* 28:209-215, 1996.
Ausubel et al., In: *Current Protocols in Molecular Biology*, John, Wiley & Sons, Inc, New York, 1998.
Barker et al., In: *Plant and Soil Nematodes: Societal Impact and Focus for the Future*, Comm. Natl. Needs Priorities Nematol., Cooperative State Research Service, US Dept. Arig. Soc. Nematologists, 1994.
Bevan et al., *Nature,* 304:184-187, 1983.
Broothaerts et al., *Nature,* 433:629-633, 2005.
Brutlag et al., *Computers and Chemistry,* 17:203-207, 1993.
David et al., *Biotechnology* 2:73-76, 1984.
De Meutter et al. *Mol Plant Path* 6:321-325, 2005.
Dellaporta et al., In: *Chromosome Structure and Function: Impact of New Concepts,* 18th Stadler Genetics Symposium, 11:263-282, 1988.

Elbashir et al., *Genes Dev.*, 5(2):188-200, 2001.
EP 0 120 516
EP 0 122 791
Gamborg et al., *In Vitro* 12 473-478, 1976.
Gheysen and Fenoll, *Annu. Rev. Phytopathol.* 40:191-219, 2002.
Gruber et al., In: *Vectors for Plant Transformation*, Methods in Plant Molecular Biology and Biotechnology, Glick and Thompson (Eds.), CRC Press, Inc., Boca Raton, 89-119, 1993.
Hamilton and Baulcombe, *Science,* 286:950-952, 1999.
Hannon, *Nature,* 418:244-251, 2002
Haymes et al., In: *Nucleic acid hybridization, a practical approach*, IRL Press, Washington, D.C., 1985.
Herrera-Estrella et al., *Nature,* 303:209-213, 1983.
Hirel et al., *Plant Molecular Biology,* 20:207-218, 1992.
Horsch et al., *Science,* 227:1229, 1985.
Ikatu et al., *Bio/Technol.*, 8:241-242, 1990.
Jefferson et al., *EMBO J.,* 6:3901-3907, 1987.
Juergensen et al. *Plant Physiol* 131:61-69, 2003.
Kaeppler et al., *Plant Cell Rep.,* 8:415-418, 1990.
Katz et al., *J. Gen Microbiol.,* 129:2703-2714, 1983.
Klee et al., *Bio/Technol.,* 3:637-642, 1985.
Matz et al., *Nat. Biotechnol.* 17:969-973, 1999.
Mazarei et al. *Plant Mol. Biol.* 53:513-530 2003.
Mazarei et al. *Mol Plant Path* 5:409-423, 2004.
McCarter et al., *Genome Biology,* 4:R26, 1-19, 2003.
McCarter, *Trends in Parasitology,* 20:462-468, 2004.
Miki et al., In: *Procedures for Introducing Foreign DNA into Plants*, Methods in Plant Molecular Biology and Biotechnology, Glick and Thompson (Eds.), CRC Press, Inc., Boca Raton, 67-88, 1993.
Moloney et al., *Plant Cell Reports,* 8:238, 1989.
Murashige and Skoog, *Physiol. Plant.* 15: 473-497, 1962.
Narayanan et al., *Crop Sci.* 39:1680-1686, 1999.
Odell et al., *Nature,* 313:810-812, 1985.
Omirulleh et al., *Plant Mol. Biol.,* 21:415-428, 1993.
Opperman et al., *Science* 263:221-223, 1994.
Ow et al., *Science,* 234:856-859, 1986.
Padgette et al., *Crop Sci.,* 35:1451-1461, 1995.
Papp et al., *Nature,* 424:194-197, 2003.
PCT Appln. WO 97/32016; PCT Appln. WO 99/49029; PCT Appln. WO 99/53050; PCT Appln. WO94/01550; PCT Appln. WO98/05770
Piano et al., *Curr Biol.,* 12:1959-64, 2002.
Potrykus et al., *Mol. Gen. Genet.,* 199:183-188, 1985.
Reynolds et al. *Nat. Biotechnol.* 22:326-330, 2004.
Sambrook et al., (ed.), Molecular Cloning, Cold Spring Harbor Laboratory Press, Cold Spring Harbor, N.Y., 1989.
Sutcliffe, *Proc. Natl. Acad. Sci. USA,* 75:3737-3741, 1978.
Thurau et al. *Plant Mol Biol* 52:643-660, 2003.
Vaghchhipawala et al. *Genome* 47:404-413, 2004.
Van Heeke and Schuster, *J. Biol. Chem.,* 264:5503-5509, 1989.
White and Nester, *J Bacteriol.,* 141(3):1134-1141, 1988.
Winston et al., *Science,* 295:2456-2459, 2002.
Zukowski et al., *Proc. Natl. Acad. Sci. USA,* 80:1101-1105, 1983.

What is claimed is:

1. A polynucleotide encoding a double stranded ribonucleotide molecule, the ribonucleotide comprising:
   (a) a fragment of at least 23 contiguous nucleotides of SEQ ID NO: 25; and
   (b) the reverse complement of the fragment of (a), wherein uptake by a plant-parasitic nematode of a ribonucleotide molecule comprising the 23 contiguous nucleotides inhibits plant-parasitic nematode infestation.

2. The polynucleotide of claim 1, defined as operably linked to a heterologous promoter.

3. The polynucleotide of claim 1, comprising a spacer polynucleotide sequence between the fragment and the reverse complement of the fragment.

4. A transformation vector comprising the polynucleotide of claim 1.

5. The transformation vector of claim 4, wherein the polynucleotide is operably linked to a heterologous promoter functional in a plant cell.

6. A double stranded ribonucleotide molecule produced from the expression of a polynucleotide according to claim 1.

7. A cell transformed with the polynucleotide of claim 1.

8. The cell of claim 7, defined as prokaryotic cell.

9. The cell of claim 7, defined as a eukaryotic cell.

10. The cell of claim 7, defined as a plant cell.

11. A plant transformed with the polynucleotide of claim 1.

12. The plant of claim 11, further defined as selected from a crop of the group consisting of: corn, wheat, barley, rye, rice, potato, tomato, cucumber, pepper, clover, legume, soybean, pea, alfalfa, sugar cane, sugar beet, tobacco, carrot, cotton, rapeseed (canola), sunflower, safflower, sorghum, strawberry, banana, turf, and an ornamental.

13. A seed of the plant of claim 11, wherein the seed comprises the polynucleotide.

14. The plant of claim 11, wherein the polynucleotide is expressed in the plant as a double stranded ribonucleotide molecule.

15. The plant of claim 14, wherein the uptake by a plant-parasitic nematode of tissue of the plant comprising the double stranded ribonucleotide molecule inhibits plant-parasitic nematode infestation.

16. The plant of claim 15, wherein the plant-parasitic nematode is a *Meloidogyne* spp.

17. The plant of claim 15, wherein the plant-parasitic nematode is *Meloidogyne incognita*.

18. A commodity product produced from a plant according to claim 11, wherein the commodity product comprises a detectable amount of the polynucleotide or a ribonucleotide expressed therefrom.

19. A method for controlling a plant-parasitic nematode population comprising providing an agent comprising a double stranded ribonucleotide molecule that functions upon being taken up by the nematode to inhibit a biological function within the nematode, wherein the double stranded ribonucleotide molecule comprises at least 23 contiguous nucleotides of SEQ ID NO:25 and the reverse complement thereof.

20. A method for controlling a plant-parasitic nematode population comprising providing an agent comprising a first polynucleotide sequence comprising at least 23 contiguous nucleotides to SEQ ID NO: 25 or complements thereof, wherein the first polynucleotide is hybridized to a second polynucleotide sequence that is complementary to the first polynucleotide sequence.

21. The method of claim 20, wherein the nematode is *Meloidogyne* spp.

22. The method of claim 20, wherein the nematode is *Meloidogyne incognita*.

23. A method for controlling a plant-parasitic nematode population comprising providing in the host plant of a plant-parasitic nematode a transformed plant cell expressing a polynucleotide molecule according to claim 1, wherein the polynucleotide is expressed to produce a double stranded ribonucleic acid that functions upon being taken up by the plant-parasitic nematode to inhibit the expression of a target sequence within the nematode and results in decreased growth or reproduction of the nematode or nematode population, relative to growth or reproduction on a host plant lacking the transformed plant cell.

24. The method of claim 23, wherein the plant-parasitic nematode population exhibits decreased growth following infection of the host plant.

25. The method of claim 23, wherein the target sequence encodes a protein essential to egg production.

26. The method of claim 23, wherein said nematode comprises *Meloidogyne* spp.

27. The method of claim 23, wherein the nematode is *Meloidogyne incognita*.

28. The method of claim 23, wherein the polynucleotide functions upon being taken up by the plant-parasitic nematode to suppress expression of a gene that performs a function essential for reproduction.

29. A method for reducing the number of root knot nematode (RKN) feeding sites established in the root tissue of a host plant, comprising providing in the host plant of a *Meloidogyne* spp. a transformed plant cell expressing a polynucleotide according to claim 1, wherein the polynucleotide is expressed to produce a double stranded ribonucleic acid that functions upon being taken up by the *Meloidogyne* spp. to inhibit the expression of a target sequence within said nematode and results in a decrease in the number of feeding sites established, relative to the number of feeding sites established on a host lacking the transformed plant cell.

30. A method of controlling plant nematode pest infestation in a plant comprising providing in the diet of a plant nematode pest a dsRNA comprising the polynucleotide of claim 1.

31. The method of claim 30, wherein said diet comprises a plant cell transformed to express said polynucleotide.

32. A method for improving the yield of a crop produced from a crop plant subjected to plant-parasitic nematode infection, said method comprising the steps of,
  a) introducing a polynucleotide according to claim 1 into said crop plant;
  b) cultivating the crop plant to allow the expression of said polynucleotide; wherein expression of the polynucleotide inhibits plant-parasitic nematode infection, growth, reproduction, or loss of yield due to plant-parasitic nematode infection.

33. The method of claim 32, wherein the crop plant is selected from the group consisting of: corn, wheat, barley, rye, rice, potato, tomato, cucumber, pepper, clover, legume, soybean, pea, alfalfa, sugar cane, sugar beet, tobacco, carrot, cotton, rapeseed (canola), sunflower, safflower, sorghum, strawberry, banana, turf, and an ornamental.

34. The method of claim 32, wherein expression of the polynucleotide produces an RNA molecule that suppresses at least a first target gene in a plant-parasitic nematode that has contacted a portion of said crop plant, wherein the target gene performs at least one essential function essential to reproduction or egg production.

35. The method of claim 34, wherein the plant-parasitic nematode is a Tylenchid nematode.

36. The method of claim 35, wherein the plant-parasitic nematode is a *Meloidogyne* spp.

37. The method of claim 36, wherein the plant-parasitic nematode is *Meloidogyne incognita*.

38. A method for producing a commodity product comprising obtaining a plant according to claim 11 or a part thereof, and preparing a commodity product from the plant or part thereof.

39. A method for producing food or feed, comprising obtaining a plant according to claim 11 or a part thereof and preparing food or feed from said plant or part thereof.

40. The method of claim 39, wherein the food or feed is defined as oil, meal, protein, starch, flour or silage.

41. A method for down-regulating the expression of a target gene in a plant-parasitic nematode cell, the method comprising:
  (a) transforming a plant cell with a vector comprising a nucleic acid sequence encoding a dsRNA, the dsRNA comprising at least 23 contiguous nucleotides of SEQ ID NO: 25 and the reverse complement thereof, wherein the nucleic acid sequence is operatively linked to a promoter and a transcription termination sequence;
  (b) culturing the transformed plant cell under conditions sufficient to allow for development of a plant cell culture comprising a plurality of transformed plant cells;
  (c) selecting for transformed plant cells that have integrated the nucleic acid sequence into their genomes;
  (d) screening the transformed plant cells for expression of the dsRNA encoded by the nucleic acid sequence; and
  (e) selecting a plant cell that expresses the dsRNA.

42. The method of claim 41, further comprising regenerating a plant from the plant cell that expresses the dsRNA; whereby expression of the nucleic acid sequence in the plant is sufficient to modulate the expression of a target gene in a plant-parasitic nematode cell that contacts the transformed plant or plant cell.

* * * * *

UNITED STATES PATENT AND TRADEMARK OFFICE
CERTIFICATE OF CORRECTION

| | | |
|---|---|---|
| PATENT NO. | : 8,901,373 B2 | Page 1 of 1 |
| APPLICATION NO. | : 12/935266 | |
| DATED | : December 2, 2014 | |
| INVENTOR(S) | : Bradley et al. | |

It is certified that error appears in the above-identified patent and that said Letters Patent is hereby corrected as shown below:

Title Page 2, col. 1 line 1-3, Item (56), please insert --Lilley et al., "Recent progress in the development of RNA interference for plant parasitic nematodes," Molecular Plant Pathology, 8(5):701-711, 2007.--

Title Page 2, col. 1 line 4-7, Item (56), please insert --Lustigman et al., "RNA interference targeting cathepsin L and Z-like cysteine proteases of onchocerca volvulus confirmed their essential function during L3 molting," Mol. Biochem. Parasitol., 138:165-170, 2004.--

Title Page 2, col. 1 line 8-10, Item (56), please insert --Narayanan et al., "Expression of soybean cyst nematode resistance in transgenic hairy roots of soybean," Crop Sci., 39:1680-1686, 1999.--

Title Page 2, col. 1 line 11-12, Item (56), please insert --NCBI Accession No. XM_001896441, dated April 1, 2008.--

Signed and Sealed this
Twenty-fourth Day of March, 2015

Michelle K. Lee
*Director of the United States Patent and Trademark Office*

SEQUENCE LISTING

```
<160> NUMBER OF SEQ ID NOS: 47

<210> SEQ ID NO 1
<211> LENGTH: 2241
<212> TYPE: DNA
<213> ORGANISM: Meloidogyne incognita

<400> SEQUENCE: 1
atggcaacgg agactgaacc aaacaatgct gtggcacaac aaaatggaaa agaaactgca        60
atgaattccg agtcccaaca agaattgtca aattctgttc ctgttgaaaa tggggttggt       120
gaaactaatg gagatgaact aaaaaatgac tcttctgcca aaaatgaaga tttggatgat       180
attccatggt ctcaacgaat tagggaaaaa caacaaaatt cttcaacttc taaatctgtt       240
aaaagacctg tgacacctga agaaagtggg ggagaagaag cccaacctgt tgtaaaaaaa       300
tctgccgata aaaagcggaa gacgagacaa gcatcgcctg aaagtgaaga agaatatact       360
ccaaagaaga aatcaaaatc ttccaaaacc aaacctgaaa atccaacgcc aaagtcatct       420
gctaaaaaag agacaaaagc tgaagaagat tcggattacg aagatgacaa acccgcaaaa       480
atgaaaaaga aatcaactga aaataatcat gctaaacaag agacatcttc atctgcaagc       540
cctacaaaaa agaaaaagaa ggctgaagaa gaagaggagg tttggaagtg gtgggaagaa       600
caatcacctg aacaatcaga tggaacaatt aaatggagaa ctttagagca taaagggcca       660
atgtttgcgc cagaatatgt tccgttacct aaaaatatta aattcaaata taatggaaag       720
ccaatggatc tatccccgtc tgctgaagaa gttgccactt tttatgctaa aatgcttgat       780
catgattata cttcaaagcc tatttttaat caaaactttt ttaaagattg gagaaagaca       840
atgacctctg cagaacgttc aacaataact gatttaaaaa aatgtgattt tcgtgatata       900 aatgccatatt ttctttctga aactgaaaaa agaaaggctc gaagtaaaga agagaaaaaa       960
```

-continued

```
gcagaaaaag aaattaaaga taaagaagcg gctgaatatg gttttgcaat gctggatggt    1020
tataaacaaa aaattggaaa ttttcgaatt gaaccaccgg gacttttag aggacgagga    1080
gaacacccaa aatgggttg tttaaagcta cgagttcaac cagaagatgt tataataaat    1140
tgctctaaag gtgttacaat tcctcctccc aagggtcata aatggaaaga agttcggcat    1200
gacaatatgg tcacttggct ttgttcttgg aatgaaaatg ttttgtttag taacaaatat    1260
ataatgttaa atccttcttc aaagcttaaa ggccaaaagg attgggaaaa gttcgaaaaa    1320
gcacgaaagc ttaaaggctg tgttgggcca attcgagatc agtatttatt agactttaaa    1380
agcaaagaga tgcgaatacg acaacgtgca gttgctctct attttattga taaatttgcg    1440
cttagagctg gaaatgaaaa ggatactgat gaagctgcag atactgttgg ttgttgctct    1500
cttcgttgtg aacatataaa attacacgaa gaattggata ccagaaaata tgttgtagaa    1560
tttgattttc ttgggaaaga ttcaattcgt tattacaatc gtgtacctgt tgaaaaggct    1620
gttttttaaaa atttgaaaat ttttgtggaa ggaaaggaac ctggagatga tctctttgac    1680
agacttgata caagttctct aaatgcttat ttaaaagaat taatgatgg attaactgcc    1740
aaagtatttc gtacatataa tgcttcaatt actttacaag accaattgga taaattaaca    1800
aatcctgatg atacaatcca tgcaaagcta ctttcatata atcgtgcaaa tcgacaagtt    1860
gcaattcttt gtaatcacca acgtgcagtc cctaaaactc atgataaggc tatggaaaca    1920
ctacaaaaca agattaatga aaagaagaag gaatataaag aaatcaaggc tgaacttaag    1980
aaaaataaaa atgatgagaa attgcagaag aaatatactc gagtaaaaga acaacttgta    2040
aaattaaaaa cacagcatac cgacaaggat gaaaataaac aaattgcatt gggtacatcc    2100
aaacttaatt atttggatcc aagaatatca gttgcttggt gcaaaaaata tgacatccct    2160
atagaaaaga tttactcaaa aactcaacgt gacaaatttc gatgggctat agatatgaca    2220
aaagaggatt ttatttttg a                                              2241
```

<210> SEQ ID NO 2
<211> LENGTH: 746
<212> TYPE: PRT
<213> ORGANISM: Meloidogyne incognita

<400> SEQUENCE: 2

```
Met Ala Thr Glu Thr Glu Pro Asn Asn Ala Val Ala Gln Gln Asn Gly
  1               5                  10                  15

Lys Glu Thr Ala Met Asn Ser Glu Ser Gln Gln Glu Leu Ser Asn Ser
             20                  25                  30

Val Pro Val Glu Asn Gly Val Gly Glu Thr Asn Gly Asp Glu Leu Lys
         35                  40                  45

Asn Asp Ser Ser Ala Lys Asn Glu Asp Leu Asp Ile Pro Trp Ser
     50                  55                  60

Gln Arg Ile Arg Glu Lys Gln Gln Asn Ser Ser Thr Ser Lys Ser Val
 65                  70                  75                  80

Lys Arg Pro Val Thr Pro Glu Glu Ser Gly Gly Glu Glu Ala Gln Pro
                 85                  90                  95

Val Val Lys Lys Ser Ala Asp Lys Lys Arg Lys Thr Arg Gln Ala Ser
            100                 105                 110

Pro Glu Ser Glu Glu Glu Tyr Thr Pro Lys Lys Lys Ser Lys Ser Ser
        115                 120                 125

Lys Thr Lys Pro Glu Asn Pro Thr Pro Lys Ser Ala Lys Lys Glu
    130                 135                 140
```

```
Thr Lys Ala Glu Glu Asp Ser Asp Tyr Glu Asp Lys Pro Ala Lys
145                 150                 155                 160

Met Lys Lys Lys Ser Thr Glu Asn Asn His Ala Lys Gln Glu Thr Ser
            165                 170                 175

Ser Ser Ala Ser Pro Thr Lys Lys Lys Lys Ala Glu Glu Glu
        180                 185                 190

Glu Val Trp Lys Trp Trp Glu Glu Gln Ser Pro Glu Gln Ser Asp Gly
        195                 200                 205

Thr Ile Lys Trp Arg Thr Leu Glu His Lys Gly Pro Met Phe Ala Pro
        210                 215                 220

Glu Tyr Val Pro Leu Pro Lys Asn Ile Lys Phe Lys Tyr Asn Gly Lys
225                 230                 235                 240

Pro Met Asp Leu Ser Pro Ser Ala Glu Glu Val Ala Thr Phe Tyr Ala
            245                 250                 255

Lys Met Leu Asp His Asp Tyr Thr Ser Lys Pro Ile Phe Asn Gln Asn
            260                 265                 270

Phe Phe Lys Asp Trp Arg Lys Thr Met Thr Ser Ala Glu Arg Ser Thr
        275                 280                 285

Ile Thr Asp Leu Lys Lys Cys Asp Phe Arg Asp Ile Asn Ala Tyr Phe
290                 295                 300

Leu Ser Glu Thr Glu Lys Arg Lys Ala Arg Ser Lys Glu Glu Lys Lys
305                 310                 315                 320

Ala Glu Lys Glu Ile Lys Asp Lys Glu Ala Glu Tyr Gly Phe Ala
                325                 330                 335

Met Leu Asp Gly Tyr Lys Gln Lys Ile Gly Asn Phe Arg Ile Glu Pro
            340                 345                 350

Pro Gly Leu Phe Arg Gly Arg Gly Glu His Pro Lys Met Gly Cys Leu
        355                 360                 365

Lys Leu Arg Val Gln Pro Glu Asp Val Ile Ile Asn Cys Ser Lys Gly
        370                 375                 380

Val Thr Ile Pro Pro Lys Gly His Lys Trp Lys Glu Val Arg His
385                 390                 395                 400

Asp Asn Met Val Thr Trp Leu Cys Ser Trp Asn Glu Asn Val Leu Phe
                405                 410                 415

Ser Asn Lys Tyr Ile Met Leu Asn Pro Ser Ser Lys Leu Lys Gly Gln
            420                 425                 430

Lys Asp Trp Glu Lys Phe Glu Lys Ala Arg Lys Leu Lys Gly Cys Val
        435                 440                 445

Gly Pro Ile Arg Asp Gln Tyr Leu Leu Asp Phe Lys Ser Lys Glu Met
        450                 455                 460

Arg Ile Arg Gln Arg Ala Val Ala Leu Tyr Phe Ile Asp Lys Phe Ala
465                 470                 475                 480

Leu Arg Ala Gly Asn Glu Lys Asp Thr Asp Glu Ala Ala Asp Thr Val
                485                 490                 495

Gly Cys Cys Ser Leu Arg Cys Glu His Ile Lys Leu His Glu Glu Leu
            500                 505                 510

Asp Asn Gln Lys Tyr Val Val Glu Phe Asp Phe Leu Gly Lys Asp Ser
            515                 520                 525

Ile Arg Tyr Tyr Asn Arg Val Pro Val Glu Lys Ala Val Phe Lys Asn
            530                 535                 540

Leu Lys Ile Phe Val Glu Gly Lys Glu Pro Gly Asp Asp Leu Phe Asp
545                 550                 555                 560

Arg Leu Asp Thr Ser Ser Leu Asn Ala Tyr Leu Lys Glu Leu Met Asp
```

|   |   | 565 |   |   |   | 570 |   |   |   | 575 |   |
|---|---|---|---|---|---|---|---|---|---|---|---|

Gly Leu Thr Ala Lys Val Phe Arg Thr Tyr Asn Ala Ser Ile Thr Leu
                580                 585                 590

Gln Asp Gln Leu Asp Lys Leu Thr Asn Pro Asp Asp Thr Ile His Ala
            595                 600                 605

Lys Leu Leu Ser Tyr Asn Arg Ala Asn Arg Gln Val Ala Ile Leu Cys
        610                 615                 620

Asn His Gln Arg Ala Val Pro Lys Thr His Asp Lys Ala Met Glu Thr
625                 630                 635                 640

Leu Gln Asn Lys Ile Asn Glu Lys Lys Glu Tyr Lys Glu Ile Lys
                645                 650                 655

Ala Glu Leu Lys Lys Asn Lys Asn Asp Glu Lys Leu Gln Lys Lys Tyr
                660                 665                 670

Thr Arg Val Lys Glu Gln Leu Val Lys Leu Lys Thr Gln His Thr Asp
            675                 680                 685

Lys Asp Glu Asn Lys Gln Ile Ala Leu Gly Thr Ser Lys Leu Asn Tyr
        690                 695                 700

Leu Asp Pro Arg Ile Ser Val Ala Trp Cys Lys Lys Tyr Asp Ile Pro
705                 710                 715                 720

Ile Glu Lys Ile Tyr Ser Lys Thr Gln Arg Asp Lys Phe Arg Trp Ala
                725                 730                 735

Ile Asp Met Thr Lys Glu Asp Phe Ile Phe
            740                 745

<210> SEQ ID NO 3
<211> LENGTH: 957
<212> TYPE: DNA
<213> ORGANISM: Meloidogyne incognita
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (912)..(912)
<223> OTHER INFORMATION: n is a, c, g, or t

<400> SEQUENCE: 3
atggtttgcc ccttcttttt gacaattatt gcttacacag ctatcgctta ttttgttaaa      60
cgcattttga cttcgattta caacattgtt ttcccgtatt tatatgccgt cccacagaat     120
ttgcaagttt ggctggagc aaaatgggca gtaataactg gtggaactga cggtattgga     180
aaggcatacg cttatgaatt ggccaaaaaa caatttaata taattataat ttcgcgtaca     240
caatcaaaat tggatgatgt ggctaaagaa attaagaag aatttaagga cattgaagtg     300
agaacgattg cttttgactt tacaaatcca aaattagaag attatgagag acagatattt     360
gccaaaattg atgatgttga cattggagtt ttggttaaca atgttggaat gagctatgaa     420
tttcctgaac gctttgaacg tgttcatggt ggtattaaac gtgttgctga catgacttta     480
atcaacactt ttccgacaac tgttctttct catcatattc ttcaacaaat ggctaaacgc     540
aatagaggtg tagtggttaa tgtggcttct tcagctgcca ttttgattg gttttatttg     600 gctgtttata gtgctattaa aaaatatgtc actggtttgt tttcatttt acgtaaagaa     660 tangttgaca caaatatta tttccaacca gttttccaa tgatggttgc cacaaaaagg     720
gtaaaaatta gacgttcttc atttttatt ccttcacctg aaaaatttgt tagtgaaact     780
gttcgcagtt ttggattaac tgatgagaat acggggagtt tggcacatca aattcagggt     840

```
gaaattatgt ttggctacat cccagaatat tttttcaaca aagttgttcg ggacaatttt      900
ttgtcaactt gnaagcgggc ctggaggaaa aggggaatt ttgcgaaggc ggaataa         957
```

\<210\> SEQ ID NO 4
\<211\> LENGTH: 318
\<212\> TYPE: PRT
\<213\> ORGANISM: Meloidogyne incognita
\<220\> FEATURE:
\<221\> NAME/KEY: misc_feature
\<222\> LOCATION: (221)..(221)
\<223\> OTHER INFORMATION: Xaa can be any naturally occurring amino acid
\<220\> FEATURE:
\<221\> NAME/KEY: misc_feature
\<222\> LOCATION: (304)..(304)
\<223\> OTHER INFORMATION: Xaa can be any naturally occurring amino acid

\<400\> SEQUENCE: 4

```
Met Val Cys Pro Phe Phe Leu Thr Ile Ile Ala Tyr Thr Ala Ile Ala
1               5                   10                  15

Tyr Phe Val Lys Arg Ile Leu Thr Ser Ile Tyr Asn Ile Val Phe Pro
            20                  25                  30

Tyr Leu Tyr Ala Val Pro Gln Asn Leu Gln Val Leu Ala Gly Ala Lys
        35                  40                  45

Trp Ala Val Ile Thr Gly Gly Thr Asp Gly Ile Gly Lys Ala Tyr Ala
    50                  55                  60

Tyr Glu Leu Ala Lys Lys Gln Phe Asn Ile Ile Ile Ser Arg Thr
65                  70                  75                  80

Gln Ser Lys Leu Asp Asp Val Ala Lys Glu Ile Lys Glu Glu Phe Lys
                85                  90                  95

Asp Ile Glu Val Arg Thr Ile Ala Phe Asp Phe Thr Asn Pro Lys Leu
            100                 105                 110

Glu Asp Tyr Glu Arg Gln Ile Phe Ala Lys Ile Asp Asp Val Asp Ile
        115                 120                 125

Gly Val Leu Val Asn Asn Val Gly Met Ser Tyr Glu Phe Pro Glu Arg
    130                 135                 140

Phe Glu Arg Val His Gly Gly Ile Lys Arg Val Ala Asp Met Thr Leu
145                 150                 155                 160

Ile Asn Thr Phe Pro Thr Thr Val Leu Ser His His Ile Leu Gln Gln
                165                 170                 175

Met Ala Lys Arg Asn Arg Gly Val Val Val Asn Val Ala Ser Ser Ala
            180                 185                 190

Ala Asn Phe Asp Trp Phe Tyr Leu Ala Val Tyr Ser Ala Ile Lys Lys
        195                 200                 205

Tyr Val Thr Gly Leu Phe Ser Phe Leu Arg Lys Glu Xaa Val Asp Thr
    210                 215                 220

Asn Ile Tyr Phe Gln Pro Val Phe Pro Met Met Val Ala Thr Lys Arg
225                 230                 235                 240

Val Lys Ile Arg Arg Ser Ser Phe Phe Ile Pro Ser Pro Glu Lys Phe
                245                 250                 255

Val Ser Glu Thr Val Arg Ser Phe Gly Leu Thr Asp Glu Asn Thr Gly
            260                 265                 270

Ser Leu Ala His Gln Ile Gln Gly Glu Ile Met Phe Gly Tyr Ile Pro
        275                 280                 285

Glu Tyr Phe Phe Asn Lys Val Val Arg Asp Asn Phe Leu Ser Thr Xaa
    290                 295                 300

Lys Arg Ala Trp Arg Lys Arg Gly Asn Phe Ala Lys Ala Glu
305                 310                 315
```

<210> SEQ ID NO 5
<211> LENGTH: 1425
<212> TYPE: DNA
<213> ORGANISM: Meloidogyne incognita

<400> SEQUENCE: 5

```
atgggaatta aattcctgga atttgttaaa ccttttttgtg gttttgtgcc agaggtttct      60
aaacctgaaa gaaaaattca attcaggaa aagatgcttt ggactgcgat aactcttttt     120
gtttttcttg tttgctgtca gattccactt tttggtatta tgtccactga cagtgctgat     180
cctctttatt ggcttcgagt tattatggca tctaatagag gaacgcttat ggaattggga     240
atctctccaa ttgtaacttc tggtcttatt atgcaacttt ggctggtgc aaaaattatt     300
gaagttgggg atactccaaa ggaaagagct ctttttaatg gtgcccagaa attgttcgga     360
atggtcataa ctatcggtca agctattgtt tatgttgcct ctggaatgta tggaaatcct     420
catgaaattg gtgcaggaat tgtcttttta atcgttattc aattagttgt tgctggatta     480
attgttcttt tacttgacga attacttcag aaaggctatg gacttggttc aggaatttcc     540
ctctttattg ctacaaacat ttgcgaaact attgttggaa agcattttc acctgcgaca     600
atgaatacag gaagaggaac cgaatttgaa ggtgcaataa ttgctttatt tcatctgttg     660
tcaactcgta atgacaaagt ccgtgcactc agagaagctt tttaccgtca aaatttgcca     720
aatttgatga acttattggc tactgtgctc gttttttgctg ttgttatata cttccagggc     780
ttccgtgttg atttgccaat taaaagttct cgttatcgtg ccaacatag ttcatatcca     840
atcaaattgt tttatacaag taatatacca ataattcttc aatctgcttt ggtctccaat     900
ttatacgtta tctctcaaat gttggcagct aaatttggag gaaatattct tgttaatata     960
cttggtacat ggtctgactc ttcaggcact tataggagtt atccaacagg aggtatttgc    1020
tactacctat caccaccaga atcattgtca catgtagttg aagacccaat tcattgtttt    1080
acctacattg tctttatgct tggttcatgt gcatttttct caaaaacctg gattgatgtt    1140
agcggttcaa gtgctaaaga tgttgcgaaa caattaaaag agcaacaaat gataatgaga    1200
ggacataggg aaaaatcaat gattcacgaa ttaaatcgtt atattcctac tgctgctgct    1260
tttggtggtt tatgtattgg agcactttct gttactgctg actttatggg agctattgga    1320
agtggaacgg gaattttact tgcggtcacc attatttatc agtatttcga aatatttgtg    1380
aaagaacagc aagaaatggg tggcgttttct ggtttattct tttga                    1425
```

<210> SEQ ID NO 6
<211> LENGTH: 474
<212> TYPE: PRT
<213> ORGANISM: Meloidogyne incognita

<400> SEQUENCE: 6

Met Gly Ile Lys Phe Leu Glu Phe Val Lys Pro Phe Cys Gly Phe Val
1               5                   10                  15

Pro Glu Val Ser Lys Pro Glu Arg Lys Ile Gln Phe Arg Glu Lys Met
            20                  25                  30

Leu Trp Thr Ala Ile Thr Leu Phe Val Phe Leu Val Cys Cys Gln Ile
        35                  40                  45

Pro Leu Phe Gly Ile Met Ser Thr Asp Ser Ala Asp Pro Leu Tyr Trp
    50                  55                  60

Leu Arg Val Ile Met Ala Ser Asn Arg Gly Thr Leu Met Glu Leu Gly
65                  70                  75                  80

```
Ile Ser Pro Ile Val Thr Ser Gly Leu Ile Met Gln Leu Leu Ala Gly
                85                  90                  95

Ala Lys Ile Ile Glu Val Gly Asp Thr Pro Lys Glu Arg Ala Leu Phe
            100                 105                 110

Asn Gly Ala Gln Lys Leu Phe Gly Met Val Ile Thr Ile Gly Gln Ala
        115                 120                 125

Ile Val Tyr Val Ala Ser Gly Met Tyr Gly Asn Pro His Glu Ile Gly
    130                 135                 140

Ala Gly Ile Cys Leu Leu Ile Val Ile Gln Leu Val Val Ala Gly Leu
145                 150                 155                 160

Ile Val Leu Leu Leu Asp Glu Leu Leu Gln Lys Gly Tyr Gly Leu Gly
                165                 170                 175

Ser Gly Ile Ser Leu Phe Ile Ala Thr Asn Ile Cys Glu Thr Ile Val
            180                 185                 190

Trp Lys Ala Phe Ser Pro Ala Thr Met Asn Thr Gly Arg Gly Thr Glu
        195                 200                 205

Phe Glu Gly Ala Ile Ile Ala Leu Phe His Leu Leu Ser Thr Arg Asn
    210                 215                 220

Asp Lys Val Arg Ala Leu Arg Glu Ala Phe Tyr Arg Gln Asn Leu Pro
225                 230                 235                 240

Asn Leu Met Asn Leu Leu Ala Thr Val Leu Val Phe Ala Val Val Ile
                245                 250                 255

Tyr Phe Gln Gly Phe Arg Val Asp Leu Pro Ile Lys Ser Ser Arg Tyr
            260                 265                 270

Arg Gly Gln His Ser Ser Tyr Pro Ile Lys Leu Phe Tyr Thr Ser Asn
        275                 280                 285

Ile Pro Ile Ile Leu Gln Ser Ala Leu Val Ser Asn Leu Tyr Val Ile
    290                 295                 300

Ser Gln Met Leu Ala Ala Lys Phe Gly Gly Asn Ile Leu Val Asn Ile
305                 310                 315                 320

Leu Gly Thr Trp Ser Asp Ser Gly Thr Tyr Arg Ser Tyr Pro Thr
                325                 330                 335

Gly Gly Ile Cys Tyr Tyr Leu Ser Pro Pro Glu Ser Leu Ser His Val
            340                 345                 350

Val Glu Asp Pro Ile His Cys Phe Thr Tyr Ile Val Phe Met Leu Gly
        355                 360                 365

Ser Cys Ala Phe Phe Ser Lys Thr Trp Ile Asp Val Ser Gly Ser Ser
    370                 375                 380

Ala Lys Asp Val Ala Lys Gln Leu Lys Glu Gln Gln Met Ile Met Arg
385                 390                 395                 400

Gly His Arg Glu Lys Ser Met Ile His Glu Leu Asn Arg Tyr Ile Pro
                405                 410                 415

Thr Ala Ala Ala Phe Gly Gly Leu Cys Ile Gly Ala Leu Ser Val Thr
            420                 425                 430

Ala Asp Phe Met Gly Ala Ile Gly Ser Gly Thr Gly Ile Leu Leu Ala
        435                 440                 445

Val Thr Ile Ile Tyr Gln Tyr Phe Glu Ile Phe Val Lys Glu Gln Gln
    450                 455                 460

Glu Met Gly Gly Val Ser Gly Leu Phe Phe
465                 470
```

<210> SEQ ID NO 7
<211> LENGTH: 1851

<212> TYPE: DNA
<213> ORGANISM: Meloidogyne incognita

<400> SEQUENCE: 7

```
atggaagacc aaatttcaaa aatttctgat gctgccaatc gaatgcgtat ttcttcaatt      60
gaacagacta ctaaagcaaa ttctggacat ccaacagta gttgtagtgc tgctgaaatt     120
gttgcgacac atttctttc tgaaatgcgt tattcggtta aggaacctag acatgcttct     180
gctgatcgtt ttgttttgtc taagggacat gcctgtccga ttctctatgc tgcttgggag     240
gaagcaggcc tgttaactcg agaacaagtt ttgactctgc gcaaattaaa ttctgatatt     300
gaaggacatc caactccgag ctttcatttt attgatgttg ctacaggctc tctcggacaa     360
ggactttctt gtgctgctgg gatggcttat actggaaaat atattgacaa cgcttcatat     420
cgagtctatt gtcttttggg cgatagtgaa agtgcagaag gatctgtttg ggaggctgca     480
gcattcgcaa gttattataa attggataat ctcgttacaa ttgttgatgt taatcgactt     540
ggacaatctc gtgaaactat gattggccat gatttgttta cttatgctaa gcggtttgaa     600
gcttttgggt ttaatagtat tattgttgat ggacacgatg ttgctgattt attgaaagct     660
tttgatgaag caagaaaagt aacaggccaa ccaacagcaa ttattgcacg tacattaaaa     720
gggaaaggaa ttgaaggagt tgaagataaa gataattgtc atggaaagcc agtaactttg     780
gacaaagcag aaattattgc ttcaaaattg gaaataaaa cagcaaaaaa tttgtgggaa     840
ttagaaaatt taattgatga tgctcctgaa gttgattttg aaattgggaa aattaaaatg     900
agttcgccgc caaattatca aattggagag aaggtggcta ctcgtttagc ttatggaaat     960
gctcttgtta aattggctga tacaagcaaa aggattattg ctttggatgg tgacgtgtca    1020
aattccacat tttctgataa agttctcaat aaatatcctc aacaatttgt ccaatgcttt    1080
attgctgaac aaaacatggt tggcgttgct gtaggaatgt cttgtcgtgg gcgaactatt    1140
ccacatgcga gtacttttgc tgtttttctt acccgtgctg ctgaccaaat tcgaatgggg    1200
gcaatatctt ttgctaatgt taaatttgct ggttcacatg ctggtgtctc tattggagag    1260
gatgggccaa gccaaatggg acttgaagac ctcgcacttt tccgagcagt tcctaatagt    1320
atcgttcttt atccatctga tgcggtttct acagaatatg cgactgaatt ggctgctaat    1380
tataagggaa ttacttttac tcgtactgga cgtcctaata ctccagttat ttatccaaat    1440
gatgagaaat ttgagattgg aaaatgcaag gttatccgtc aaacaaatga agacaagtat    1500
ttattaatcg gcgcgggtgt aacactttat gaatgtatta agctcatga tattttgagt    1560
tctgaaggaa ttcaagttgc tgttattgac ctttctctg tcaagccttt ggacaatcaa    1620
acacttattg agcaagctaa gcgtgttgga gggaaagttt tgactgtaga ggatcattat    1680
cagactggag gtattggtga agctgtatct ttggcgttag gtgatgttcc taatgttcgt    1740
gttcgcagtc tttgtgttaa agaaattcca cgttctggta cacctgatga gcttatggat    1800
ttgtatggaa tttctgcaaa gaaaattata gctgcagtga agaattttta a             1851
```

<210> SEQ ID NO 8
<211> LENGTH: 616
<212> TYPE: PRT
<213> ORGANISM: Meloidogyne incognita

<400> SEQUENCE: 8

```
Met Glu Asp Gln Ile Ser Lys Ile Ser Asp Ala Ala Asn Arg Met Arg
1               5                   10                  15

Ile Ser Ser Ile Glu Gln Thr Thr Lys Ala Asn Ser Gly His Pro Thr
```

```
                20                  25                  30
Ser Ser Cys Ser Ala Ala Glu Ile Val Ala Thr His Phe Phe Ser Glu
            35                  40                  45
Met Arg Tyr Ser Val Lys Glu Pro Arg His Ala Ser Ala Asp Arg Phe
 50                  55                  60
Val Leu Ser Lys Gly His Ala Cys Pro Ile Leu Tyr Ala Ala Trp Glu
 65                  70                  75                  80
Glu Ala Gly Leu Leu Thr Arg Glu Gln Val Leu Thr Leu Arg Lys Leu
                85                  90                  95
Asn Ser Asp Ile Glu Gly His Pro Thr Pro Arg Leu Ser Phe Ile Asp
            100                 105                 110
Val Ala Thr Gly Ser Leu Gly Gln Gly Leu Ser Cys Ala Ala Gly Met
            115                 120                 125
Ala Tyr Thr Gly Lys Tyr Ile Asp Asn Ala Ser Tyr Arg Val Tyr Cys
            130                 135                 140
Leu Leu Gly Asp Ser Glu Ser Ala Glu Gly Ser Val Trp Glu Ala Ala
145                 150                 155                 160
Ala Phe Ala Ser Tyr Tyr Lys Leu Asp Asn Leu Val Thr Ile Val Asp
                165                 170                 175
Val Asn Arg Leu Gly Gln Ser Arg Glu Thr Met Ile Gly His Asp Leu
            180                 185                 190
Phe Thr Tyr Ala Lys Arg Phe Glu Ala Phe Gly Phe Asn Ser Ile Ile
            195                 200                 205
Val Asp Gly His Asp Val Ala Asp Leu Leu Lys Ala Phe Asp Glu Ala
            210                 215                 220
Arg Lys Val Thr Gly Gln Pro Thr Ala Ile Ile Ala Arg Thr Leu Lys
225                 230                 235                 240
Gly Lys Gly Ile Glu Gly Val Glu Asp Lys Asn Cys His Gly Lys
                245                 250                 255
Pro Val Thr Leu Asp Lys Ala Glu Ile Ile Ala Ser Lys Leu Gly Asn
            260                 265                 270
Lys Thr Ala Lys Asn Leu Trp Glu Leu Glu Asn Leu Ile Asp Asp Ala
            275                 280                 285
Pro Glu Val Asp Phe Glu Ile Gly Lys Ile Lys Met Ser Ser Pro Pro
            290                 295                 300
Asn Tyr Gln Ile Gly Glu Lys Val Ala Thr Arg Leu Ala Tyr Gly Asn
305                 310                 315                 320
Ala Leu Val Lys Leu Ala Asp Thr Ser Lys Arg Ile Ile Ala Leu Asp
                325                 330                 335
Gly Asp Val Ser Asn Ser Thr Phe Ser Asp Lys Val Leu Asn Lys Tyr
            340                 345                 350
Pro Gln Gln Phe Val Gln Cys Phe Ile Ala Glu Gln Asn Met Val Gly
            355                 360                 365
Val Ala Val Gly Met Ser Cys Arg Gly Arg Thr Ile Pro His Ala Ser
            370                 375                 380
Thr Phe Ala Val Phe Phe Thr Arg Ala Ala Asp Gln Ile Arg Met Gly
385                 390                 395                 400
Ala Ile Ser Phe Ala Asn Val Lys Phe Ala Gly Ser His Ala Gly Val
                405                 410                 415
Ser Ile Gly Glu Asp Gly Pro Ser Gln Met Gly Leu Glu Asp Leu Ala
            420                 425                 430
Leu Phe Arg Ala Val Pro Asn Ser Ile Val Leu Tyr Pro Ser Asp Ala
            435                 440                 445
```

```
Val Ser Thr Glu Tyr Ala Thr Glu Leu Ala Ala Asn Tyr Lys Gly Ile
    450                 455                 460

Thr Phe Thr Arg Thr Gly Arg Pro Asn Thr Pro Val Ile Tyr Pro Asn
465                 470                 475                 480

Asp Glu Lys Phe Glu Ile Gly Lys Cys Lys Val Ile Arg Gln Thr Asn
                485                 490                 495

Glu Asp Lys Tyr Leu Leu Ile Gly Ala Gly Val Thr Leu Tyr Glu Cys
                500                 505                 510

Ile Lys Ala His Asp Ile Leu Ser Ser Glu Gly Ile Gln Val Ala Val
            515                 520                 525

Ile Asp Leu Phe Ser Val Lys Pro Leu Asp Asn Gln Thr Leu Ile Glu
    530                 535                 540

Gln Ala Lys Arg Val Gly Gly Lys Val Leu Thr Val Glu Asp His Tyr
545                 550                 555                 560

Gln Thr Gly Gly Ile Gly Glu Ala Val Ser Leu Ala Leu Gly Asp Val
                565                 570                 575

Pro Asn Val Arg Val Arg Ser Leu Cys Val Lys Glu Ile Pro Arg Ser
                580                 585                 590

Gly Thr Pro Asp Glu Leu Met Asp Leu Tyr Gly Ile Ser Ala Lys Lys
            595                 600                 605

Ile Ile Ala Ala Val Lys Asn Phe
    610                 615

<210> SEQ ID NO 9
<211> LENGTH: 741
<212> TYPE: DNA
<213> ORGANISM: Meloidogyne incognita

<400> SEQUENCE: 9
atggcttctt cttatgatcg agcaattact attttctcgc cagatggtcg tctctttcaa      60
gttgattatg cgcaggaagc tgttaaaaaa ggctcaactg ctgtgggcgt taaagggaag     120
gattgcattg tgattggcgt tgagaagaaa tctgttcctg ttcttcaaga tgaccgcaca     180
attcgaaaga tacacaaatt ggatgatcac gtaatggctg cttttgctgg tttgagtgca     240
gatgctcgtg ttttgattga ccgtgccaga gttgcttgtg aaaattacaa attgactttg     300
gaggatcccg tcacacttga gcacatctcc cgcactattg cggacttgaa acatgaattt     360
acgcaaacta caggtcgtcg tccttttggt gtctctttac ttgttggcgg ttttgatccc     420
gatggaactc ctcatctttt tattactgaa ccatctggtg tgtattacga attacttgct     480
ggctcaatcg gccggaatga gaaggttgtc aaagaatatt tggaggagaa ttataatgat     540
ggcaatgttt caaacgaaaa cttggtcttg aagttggtgg tcaaagctct tgtcccagtt     600
gtgcaaactg gagcgcgtaa tatggagata tcggtgttga agcgtgataa tgagggggaat     660 attgttcaac gtgttctact cactgaggag ttggaggaaa ttttacgtca aattgaagct     720
gaaactatgg agactgttta g                                              741

<210> SEQ ID NO 10
<211> LENGTH: 246
<212> TYPE: PRT
<213> ORGANISM: Meloidogyne incognita

<400> SEQUENCE: 10

Met Ala Ser Ser Tyr Asp Arg Ala Ile Thr Ile Phe Ser Pro Asp Gly
1               5                   10                  15
```

```
Arg Leu Phe Gln Val Asp Tyr Ala Gln Glu Ala Val Lys Lys Gly Ser
            20                  25                  30
Thr Ala Val Gly Val Lys Gly Lys Asp Cys Ile Val Ile Gly Val Glu
        35                  40                  45
Lys Lys Ser Val Pro Val Leu Gln Asp Asp Arg Thr Ile Arg Lys Ile
50                  55                  60
His Lys Leu Asp Asp His Val Met Ala Ala Phe Ala Gly Leu Ser Ala
65                  70                  75                  80
Asp Ala Arg Val Leu Ile Asp Arg Ala Arg Val Ala Cys Glu Asn Tyr
                85                  90                  95
Lys Leu Thr Leu Glu Asp Pro Val Thr Leu Glu His Ile Ser Arg Thr
            100                 105                 110
Ile Ala Asp Leu Lys His Glu Phe Thr Gln Thr Thr Gly Arg Arg Pro
        115                 120                 125
Phe Gly Val Ser Leu Leu Val Gly Gly Phe Asp Pro Asp Gly Thr Pro
130                 135                 140
His Leu Phe Ile Thr Glu Pro Ser Gly Val Tyr Tyr Glu Leu Leu Ala
145                 150                 155                 160
Gly Ser Ile Gly Arg Asn Glu Lys Val Val Lys Glu Tyr Leu Glu Glu
                165                 170                 175
Asn Tyr Asn Asp Gly Asn Val Ser Asn Glu Asn Leu Val Leu Lys Leu
            180                 185                 190
Val Val Lys Ala Leu Val Pro Val Gln Thr Gly Ala Arg Asn Met
        195                 200                 205
Glu Ile Ser Val Leu Lys Arg Asp Asn Glu Gly Asn Ile Val Gln Arg
210                 215                 220
Val Leu Leu Thr Glu Glu Leu Glu Glu Ile Leu Arg Gln Ile Glu Ala
225                 230                 235                 240
Glu Thr Met Glu Thr Val
                245

<210> SEQ ID NO 11
<211> LENGTH: 1122
<212> TYPE: DNA
<213> ORGANISM: Meloidogyne incognita

<400> SEQUENCE: 11
atgtctggac atagcgtaga tgaggcacaa cttgcttctt gccaggctta tgtgcgtcaa      60
cacaatattc aacaacttgt taaagatgcc atagtttctt tatgcatcca taaacctgaa     120
aatccggtga ttttcttgcg tgaccacttt gatcagttgt cagccgatca acaaaacttc     180
tcacaggaaa cagtccattc agttcccgac gaagacgaca ccctggaaga acctccacgt     240
ctcccacaag gcaatcgccg ccgattgggc gtttctgccg aagttccaga tgaaaacgaa     300
gccgcgaatt accaacgagt agttattcca aaagatgatg atacacaaaa agctttgaga     360
caggcaatgt gccgaaatgt tttgtttgca catttggatt tgatgaaca aaaagcaatt      420 tcgatgcaa tgtttccagt agagaagaaa aagggagaaa ttattattga caggggagaa      480
gaaggagata ttttttatgt aatcgaaagt ggagaagttg attgtttcgt taatggggaa     540
tttgttctct cagttaagga aggaggttct tttggtgaac ttgccttaat ttatggaact     600
ccacgtgctg ctactgttgt agctaagacc ccaacagtca aactttgggc tattgaccga     660
ctcacctata gagctatttt aatgggatct acaatgcgca aaagaaaaat gtatgacgaa     720
tttttgtcga aagtttcaat tcttgccgat cttgacaagt gggaacgtgc aaatgttgct     780
```

```
gatgctttgg aacaatgcca atttgaacct ggaactagaa ttgttgaaca gggccaaccc    840
ggagatgaat tctttataat tgttgaggga aagccgagg tgctacaacg gccgaatgat    900
gatgctcctt atgaagttgt tggcaaattg ggtccttctg attattttgg cgaaattgct    960
cttttattgg atcatccacg tgcagcaacc gttgtggcta aagggcccct taagtgtgta    1020
aagttggata gagctcgatt cgagcgcgtt atgggcccag tgcgtgaaat tctcaaacgt    1080
gatgttagcc attacaattc ttatgtgaag ttgatgacct aa                      1122
```

<210> SEQ ID NO 12
<211> LENGTH: 373
<212> TYPE: PRT
<213> ORGANISM: Meloidogyne incognita

<400> SEQUENCE: 12

```
Met Ser Gly His Ser Val Asp Glu Ala Gln Leu Ala Ser Cys Gln Ala
1               5                   10                  15

Tyr Val Arg Gln His Asn Ile Gln Gln Leu Val Lys Asp Ala Ile Val
            20                  25                  30

Ser Leu Cys Ile His Lys Pro Glu Asn Pro Val Ile Phe Leu Arg Asp
        35                  40                  45

His Phe Asp Gln Leu Ser Ala Asp Gln Gln Asn Phe Ser Gln Glu Thr
    50                  55                  60

Val His Ser Val Pro Asp Glu Asp Thr Leu Glu Glu Pro Pro Arg
65                  70                  75                  80

Leu Pro Gln Gly Asn Arg Arg Arg Leu Gly Val Ser Ala Glu Val Pro
                85                  90                  95

Asp Glu Asn Glu Ala Ala Asn Tyr Gln Arg Val Val Ile Pro Lys Asp
            100                 105                 110

Asp Asp Thr Gln Lys Ala Leu Arg Gln Ala Met Cys Arg Asn Val Leu
        115                 120                 125

Phe Ala His Leu Asp Val Asp Glu Gln Lys Ala Ile Phe Asp Ala Met
    130                 135                 140

Phe Pro Val Glu Lys Lys Lys Gly Glu Ile Ile Ile Glu Gln Gly Glu
145                 150                 155                 160

Glu Gly Asp Asn Phe Tyr Val Ile Glu Ser Gly Glu Val Asp Cys Phe
                165                 170                 175

Val Asn Gly Glu Phe Val Leu Ser Val Lys Glu Gly Gly Ser Phe Gly
            180                 185                 190

Glu Leu Ala Leu Ile Tyr Gly Thr Pro Arg Ala Ala Thr Val Val Ala
        195                 200                 205

Lys Thr Pro Thr Val Lys Leu Trp Ala Ile Asp Arg Leu Thr Tyr Arg
    210                 215                 220

Ala Ile Leu Met Gly Ser Thr Met Arg Lys Lys Met Tyr Asp Glu
225                 230                 235                 240

Phe Leu Ser Lys Val Ser Ile Leu Ala Asp Leu Asp Lys Trp Glu Arg
                245                 250                 255

Ala Asn Val Ala Asp Ala Leu Glu Gln Cys Gln Phe Glu Pro Gly Thr
            260                 265                 270

Arg Ile Val Glu Gln Gly Gln Pro Gly Asp Glu Phe Ile Ile Val
        275                 280                 285

Glu Gly Glu Ala Glu Val Leu Gln Arg Pro Asn Asp Asp Ala Pro Tyr
    290                 295                 300

Glu Val Val Gly Lys Leu Gly Pro Ser Asp Tyr Phe Gly Glu Ile Ala
305                 310                 315                 320
```

Leu Leu Leu Asp His Pro Arg Ala Ala Thr Val Val Ala Lys Gly Pro
            325                 330                 335

Leu Lys Cys Val Lys Leu Asp Arg Ala Arg Phe Glu Arg Val Met Gly
            340                 345                 350

Pro Val Arg Glu Ile Leu Lys Arg Asp Val Ser His Tyr Asn Ser Tyr
        355                 360                 365

Val Lys Leu Met Thr
        370

<210> SEQ ID NO 13
<211> LENGTH: 993
<212> TYPE: DNA
<213> ORGANISM: Meloidogyne incognita

<400> SEQUENCE: 13
aagccaagcc ctgtgcaaga agctgctatt ggacccgctc tttcgggaca agatgtgctc    60
gctcgtgcta agaatggaac aggaaagacg ggcgccttcg caatcccagt gatcgagaag   120
atcgacgtga acatcaagaa agtgcaagca atcattatgg tgccaactcg tgagctcgct   180
cttcaaacat cgcaaatctg cgtggagctt ggaaagcata tgaatgtcaa ggtgatggtt   240
acaactggcg gtacggattt gcgtgacgac attatgcgtc tcaatggaac cgttcatctg   300
attgtgcaa ctcccggacg aatcttggat ctcatcgaga agactgttgc tgatgtgagc   360
ctctgcaaga tgcttgtctt ggatgaagcc gacaaactac tttcgatcga ttttcaaggt   420
gctctcgata gatgatcag ctacttacca agagagcgcc aaattatgct tttctcggca   480
acgtttccat tggcggtggc caacttcatg caaaagtaca tgaagaaacc gtacgaaatc   540
aatctgatgg aggaactcac tcttcatggc gtcacccaat actacgctta tgtccaagag   600
aagcaaaagg ttcactgcct caatacgctt ttccggaagc tgcaagtcaa ccaatcaatc   660
atcttctgca attcaacaca gcgtgtggaa cttttggcaa agaagatcac tgaaatcggt   720
tactcctgct actacattca ttcgcgaatg atgcaacaag ataggaaccg cgtcttccac   780
gatttccgtc aaggaaactg ccgcaacttg gtctgttcgg atcttctcac tagaggcatt   840
gacatccaag ctgtgaatgt tgtgattaat tttgattttc ctcgcaactc tgagacttat   900
cttcacagaa ttggacgttc tggccgattt ggacatctcg aatcgcaat taacctcatt   960
acttatgagg atcgttacaa tctcaagcgc att                                993

<210> SEQ ID NO 14
<211> LENGTH: 332
<212> TYPE: PRT
<213> ORGANISM: Meloidogyne incognita

<400> SEQUENCE: 14

Glu Lys Pro Ser Pro Val Gln Glu Ala Ala Ile Gly Pro Ala Leu Ser
1               5                   10                  15

Gly Gln Asp Val Leu Ala Arg Ala Lys Asn Gly Thr Gly Lys Thr Gly
            20                  25                  30

Ala Phe Ala Ile Pro Val Ile Glu Lys Ile Asp Val Asn Ile Lys Lys
        35                  40                  45

Val Gln Ala Ile Ile Met Val Pro Thr Arg Glu Leu Ala Leu Gln Thr
    50                  55                  60

Ser Gln Ile Cys Val Glu Leu Gly Lys His Met Asn Val Lys Val Met
65                  70                  75                  80

Val Thr Thr Gly Gly Thr Asp Leu Arg Asp Asp Ile Met Arg Leu Asn

```
                85                  90                  95
Gly Thr Val His Leu Ile Val Ala Thr Pro Gly Arg Ile Leu Asp Leu
            100                 105                 110

Ile Glu Lys Thr Val Ala Asp Val Ser Leu Cys Lys Met Leu Val Leu
            115                 120                 125

Asp Glu Ala Asp Lys Leu Leu Ser Ile Asp Phe Gln Gly Ala Leu Asp
    130                 135                 140

Lys Met Ile Ser Tyr Leu Pro Arg Glu Arg Gln Ile Met Leu Phe Ser
145                 150                 155                 160

Ala Thr Phe Pro Leu Ala Val Ala Asn Phe Met Gln Lys Tyr Met Lys
                165                 170                 175

Lys Pro Tyr Glu Ile Asn Leu Met Glu Glu Leu Thr Leu His Gly Val
            180                 185                 190

Thr Gln Tyr Tyr Ala Tyr Val Gln Glu Lys Gln Lys Val His Cys Leu
            195                 200                 205

Asn Thr Leu Phe Arg Lys Leu Gln Val Asn Gln Ser Ile Ile Phe Cys
    210                 215                 220

Asn Ser Thr Gln Arg Val Glu Leu Leu Ala Lys Lys Ile Thr Glu Ile
225                 230                 235                 240

Gly Tyr Ser Cys Tyr Tyr Ile His Ser Arg Met Met Gln Gln Asp Arg
                245                 250                 255

Asn Arg Val Phe His Asp Phe Arg Gln Gly Asn Cys Arg Asn Leu Val
            260                 265                 270

Cys Ser Asp Leu Leu Thr Arg Gly Ile Asp Ile Gln Ala Val Asn Val
    275                 280                 285

Val Ile Asn Phe Asp Phe Pro Arg Asn Ser Glu Thr Tyr Leu His Arg
290                 295                 300

Ile Gly Arg Ser Gly Arg Phe Gly His Leu Gly Ile Ala Ile Asn Leu
305                 310                 315                 320

Ile Thr Tyr Glu Asp Arg Tyr Asn Leu Lys Arg Ile
            325                 330

<210> SEQ ID NO 15
<211> LENGTH: 3225
<212> TYPE: DNA
<213> ORGANISM: Meloidogyne incognita

<400> SEQUENCE: 15
atgaagcata caagacctat atttgacgaa gaaccagcaa taaaaattac tcgttgtgga      60
aattcttcta tttgttctca agaaacggaa aaataatgc cggcatctga aaccaatcaa      120
aataattcaa atcaaacagg aggaaatgca atggtccaa actctgccga ccattctgtt     180
gacacaaatc tttattcacg acaaatttat gcattgggcg aatctgccat gactcattta     240
cgcaaggctt cggttttgat tagtggtatt ggatccgttg ggctcgaaat cgccaagaat     300
gttatccttg gtggcgttcg tcacgtaact ctacatgacc aaaaactttt gacttttgga     360
gatttatcag cgtgttttta tgctgacgag tcaatggtgg gtgagaatcg tgccaaaatc     420
tcttttacaa agttggccga attgaatgac accgtcactt gcactcttca cacagaagca     480
ttgaatgagg aatttgtgaa acagtttgat ttagttatcg ttactgattc accttgggaa     540
gagcaaatta aaattaacaa ctggatgcgg aaacatggca agctgttcat ttctgccgat     600
gctagaggtc ttttttcata tgcttttgtt gatcttggtg agaaatttgc tgtgcacgat     660
gttgatggtg aaacttataa tgaagtatta ctcgagcatg ttaattgtga gactggtgaa     720
```

-continued

```
atatttactc ttgacaaagc ttatcatgga ttggaagatg gagatcatat tgttttttgag      780 gattttgaga ttgcagaact taataaattg acaccaaccc cagtaaaaac aactgcaaaa      840
ggtcatattg tcaatgttgg caaagctctt tctagcttct cttcagtcat tgatggccca      900
atttctcgag gaagggctcg taaagttaaa atgccgaaat ttattgagtt taaatcactt      960
gctgaagcat taaagtcccc agaatttatg atttgggatt ttgctaaatt tgatggttcg     1020
gaacatctcc accgcctctg gcaagcactc tacaaattcg agaaaaagca caaacgttca     1080
ccaaaacctc gttccaaaaa ggatgccgaa ttgtttaaag ctgaacttga agggactgga     1140
acagcagaga ttcctgaaca attgctgctc aattttttctt atcaggccac tggaaatctt     1200
caacctgtcg cttctgttat tggtggatttt gttgctcaag aggcatttaa agctgtcact     1260
catcacacga caccttttgaa acaatttttta tatacggact cgtgtgaagc acttcctggt     1320
gattactcta gctttgatgc tggtaaattg actgaaaagg attgtgaacc gcgccaaact     1380
cgttatgacg gtcaagcagc tgttttttggc tggtccttcc aagcagcatt atctaaacaa     1440
aattggttta ttgttggcgc aggtgccatt ggttgtgaac tttttaaaaa tatggttatg     1500
atgggattgg cagcgggaaa tggtggtcta cttaaagtta cagatccaga tactattgaa     1560
gtttctaact tgaatagaca attcctcttt cgtcgacctg atgttgggaa aaagaaatct     1620
gaagttgctg ctcgttctat gaagcaattc aacccagcag ttaatgtcca agctctttct     1680
gatattgttt ctgaggcaac agagagtgtt ttcaacgatg acttttttcaa tcaattaaat     1740 ggtgtttgta atgctttgga taatgttgaa gctcgtcgct atgttgatcg acgttgtgtt     1800
tattatcagc tgccattgct tgaatctgga acaatgggag caaaaggaaa tactcaagtg     1860
gttttcccac acttaactga atcatacggt tcgacttctg atccgcccga atcagaaaca     1920 cctgttttgta cactcaagaa tttcccatat caaattcagc atacgattca atgggctcga     1980
tcgaaatttg ctgatcattt tacctcggtt gcagaaacag ccaatcaata tttggatgat     2040
gtaaatggtt ttcttggccg tcttcaacaa atgaccgttt ctcaaaagat cgaattactg     2100
cgtgcattaa ataaagcttt aattgatgaa tgcccaagca gtgctgaaga ttgtgtcaaa     2160
tgggcgcgtg atttgtttga ctcgctctat agaaatgaga ttatgcaact gttgcacaat     2220
tttcctcctg atcaggttac ttctcaagga caaaagtttt ggtcaggaac taagcgttgt     2280
cctcatccat tgaattttga cgttgacaat cccgaacatt tggaatttgt ttattcagcg     2340
gcttttctac gagcacaact ttataatatt gaaccaatta gtgaccctat caaagttgct     2400
catcttgctc gcgccatcat atcaccagaa ttcaaaccga gagaaggcat taagattgca     2460
gttactgatg cagaggctgc tgctaacgat gaagctggcc ctgaaggaga tgacagtgaa     2520
aagcttcttg atactttaaa tatgaatttg gctcgtttaa aaattgataa tattcgccgt     2580
ttaactccta tcgattttga aaaggatgat gacacaaatc accatattga ctttattact     2640
gcagcttcaa atttgcgtgc agaaaattat acgatagaga aggctgatag aatgaagacc     2700
aaacaaattg ctggtaaaat tattcctgca ttggctacaa cgacttcagt tgttgctgga     2760
cttgtttgta ttgaactttta taagactatt gaggttgaag gccaacgttc gaaggcacct     2820
attgaacgtt ttaaaaacgc ttttcttaac ctggcaactc ctttttattgc tttcagtgaa     2880 cctggaaaag cgtcgaaaaa gaagtatcgt gatattgaat ttactctttg ggatagattg     2940
gaagtaaatg gtcctaaaac acttggacag tttattgaat ggattgagac acaaactgga     3000
ttaactgtct caatgatgtc ttctggtgtt tcgcttcttt atgctttctt ccagccacct     3060
agtaaagttg ctgaacgtaa aaccagagat gttattcaag ttgtggagga agtgtctcgt     3120
```

-continued

```
aataaagttc ctccatttcg tcgttcactt gtatttgagg caattactca aaatgataag    3180
gacgaggatg ttgagattcc ttatgtcaaa tataatttcc gttaa                    3225
```

<210> SEQ ID NO 16
<211> LENGTH: 1074
<212> TYPE: PRT
<213> ORGANISM: Meloidogyne incognita

<400> SEQUENCE: 16

```
Met Lys His Thr Arg Pro Ile Phe Asp Glu Glu Pro Ala Ile Lys Ile
1               5                   10                  15

Thr Arg Cys Gly Asn Ser Ser Ile Cys Ser Gln Arg Asn Gly Lys Ile
            20                  25                  30

Met Pro Ala Ser Glu Thr Asn Gln Asn Asn Ser Asn Gln Thr Gly Gly
        35                  40                  45

Asn Ala Asn Gly Pro Asn Ser Ala Asp His Ser Val Asp Thr Asn Leu
    50                  55                  60

Tyr Ser Arg Gln Ile Tyr Ala Leu Gly Glu Ser Ala Met Thr His Leu
65                  70                  75                  80

Arg Lys Ala Ser Val Leu Ile Ser Gly Ile Gly Ser Val Gly Leu Glu
                85                  90                  95

Ile Ala Lys Asn Val Ile Leu Gly Gly Val Arg His Val Thr Leu His
            100                 105                 110

Asp Gln Lys Leu Leu Thr Phe Gly Asp Leu Ser Ala Cys Phe Tyr Ala
        115                 120                 125

Asp Glu Ser Met Val Gly Glu Asn Arg Ala Lys Ile Ser Phe Thr Lys
    130                 135                 140

Leu Ala Glu Leu Asn Asp Thr Val Thr Cys Thr Leu His Thr Glu Ala
145                 150                 155                 160

Leu Asn Glu Glu Phe Val Lys Gln Phe Asp Leu Val Ile Val Thr Asp
                165                 170                 175

Ser Pro Trp Glu Glu Gln Ile Lys Ile Asn Asn Trp Met Arg Lys His
            180                 185                 190

Gly Lys Leu Phe Ile Ser Ala Asp Ala Arg Gly Leu Phe Ser Tyr Ala
        195                 200                 205

Phe Val Asp Leu Gly Glu Lys Phe Ala Val His Asp Val Asp Gly Glu
    210                 215                 220

Thr Tyr Asn Glu Val Leu Leu Glu His Val Asn Cys Glu Thr Gly Glu
225                 230                 235                 240

Ile Phe Thr Leu Asp Lys Ala Tyr His Gly Leu Glu Asp Gly Asp His
                245                 250                 255

Ile Val Phe Glu Asp Phe Glu Ile Ala Glu Leu Asn Lys Leu Thr Pro
            260                 265                 270

Thr Pro Val Lys Thr Thr Ala Lys Gly His Ile Val Asn Val Gly Lys
        275                 280                 285

Ala Leu Ser Ser Phe Ser Ser Val Ile Asp Gly Pro Ile Ser Arg Gly
    290                 295                 300

Arg Ala Arg Lys Val Lys Met Pro Lys Phe Ile Glu Phe Lys Ser Leu
305                 310                 315                 320

Ala Glu Ala Leu Lys Ser Pro Glu Phe Met Ile Trp Asp Phe Ala Lys
                325                 330                 335

Phe Asp Gly Ser Glu His Leu His Arg Leu Trp Gln Ala Leu Tyr Lys
            340                 345                 350
```

```
Phe Glu Lys Lys His Lys Arg Ser Pro Lys Pro Arg Ser Lys Lys Asp
            355                 360                 365

Ala Glu Leu Phe Lys Ala Glu Leu Gly Thr Gly Thr Ala Glu Ile
370                 375                 380

Pro Glu Gln Leu Leu Leu Asn Phe Ser Tyr Gln Ala Thr Gly Asn Leu
385                 390                 395                 400

Gln Pro Val Ala Ser Val Ile Gly Gly Phe Ala Gln Glu Ala Phe
            405                 410                 415

Lys Ala Val Thr His His Thr Thr Pro Leu Lys Gln Phe Leu Tyr Thr
            420                 425                 430

Asp Ser Cys Glu Ala Leu Pro Gly Asp Tyr Ser Ser Phe Asp Ala Gly
            435                 440                 445

Lys Leu Thr Glu Lys Asp Cys Glu Pro Arg Gln Thr Arg Tyr Asp Gly
            450                 455                 460

Gln Ala Ala Val Phe Gly Trp Ser Phe Gln Ala Ala Leu Ser Lys Gln
465                 470                 475                 480

Asn Trp Phe Ile Val Gly Ala Gly Ala Ile Gly Cys Glu Leu Phe Lys
                485                 490                 495

Asn Met Val Met Met Gly Leu Ala Ala Gly Asn Gly Gly Leu Leu Lys
            500                 505                 510

Val Thr Asp Pro Asp Thr Ile Glu Val Ser Asn Leu Asn Arg Gln Phe
            515                 520                 525

Leu Phe Arg Arg Pro Asp Val Gly Lys Lys Ser Glu Val Ala Ala
            530                 535                 540

Arg Ser Met Lys Gln Phe Asn Pro Ala Val Asn Val Gln Ala Leu Ser
545                 550                 555                 560

Asp Ile Val Ser Glu Ala Thr Glu Ser Val Phe Asn Asp Asp Phe Phe
                565                 570                 575

Asn Gln Leu Asn Gly Val Cys Asn Ala Leu Asp Asn Val Glu Ala Arg
            580                 585                 590

Arg Tyr Val Asp Arg Arg Cys Val Tyr Tyr Gln Leu Pro Leu Leu Glu
            595                 600                 605

Ser Gly Thr Met Gly Ala Lys Gly Asn Thr Gln Val Val Phe Pro His
610                 615                 620

Leu Thr Glu Ser Tyr Gly Ser Thr Ser Asp Pro Pro Glu Ser Glu Thr
625                 630                 635                 640

Pro Val Cys Thr Leu Lys Asn Phe Pro Tyr Gln Ile Gln His Thr Ile
                645                 650                 655

Gln Trp Ala Arg Ser Lys Phe Ala Asp His Phe Thr Ser Val Ala Glu
            660                 665                 670

Thr Ala Asn Gln Tyr Leu Asp Asp Val Asn Gly Phe Leu Gly Arg Leu
            675                 680                 685

Gln Gln Met Thr Val Ser Gln Lys Ile Glu Leu Leu Arg Ala Leu Asn
690                 695                 700

Lys Ala Leu Ile Asp Glu Cys Pro Ser Ser Ala Glu Asp Cys Val Lys
705                 710                 715                 720

Trp Ala Arg Asp Leu Phe Asp Ser Leu Tyr Arg Asn Glu Ile Met Gln
                725                 730                 735

Leu Leu His Asn Phe Pro Pro Asp Gln Val Thr Ser Gln Gly Gln Lys
            740                 745                 750

Phe Trp Ser Gly Thr Lys Arg Cys Pro His Pro Leu Asn Phe Asp Val
            755                 760                 765

Asp Asn Pro Glu His Leu Glu Phe Val Tyr Ser Ala Ala Phe Leu Arg
```

```
                770             775             780
Ala Gln Leu Tyr Asn Ile Glu Pro Ile Ser Asp Pro Ile Lys Val Ala
785                 790             795                 800

His Leu Ala Arg Ala Ile Ile Ser Pro Glu Phe Lys Pro Arg Glu Gly
                805             810              815

Ile Lys Ile Ala Val Thr Asp Ala Glu Ala Ala Asn Asp Glu Ala
                820             825             830

Gly Pro Glu Gly Asp Asp Ser Glu Lys Leu Leu Asp Thr Leu Asn Met
            835             840             845

Asn Leu Ala Arg Leu Lys Ile Asp Asn Ile Arg Arg Leu Thr Pro Ile
            850             855             860

Asp Phe Glu Lys Asp Asp Asp Thr Asn His His Ile Asp Phe Ile Thr
865             870             875             880

Ala Ala Ser Asn Leu Arg Ala Glu Asn Tyr Thr Ile Glu Lys Ala Asp
                885             890             895

Arg Met Lys Thr Lys Gln Ile Ala Gly Lys Ile Ile Pro Ala Leu Ala
                900             905             910

Thr Thr Thr Ser Val Val Ala Gly Leu Val Cys Ile Glu Leu Tyr Lys
            915             920             925

Thr Ile Glu Val Glu Gly Gln Arg Ser Lys Ala Pro Ile Glu Arg Phe
            930             935             940

Lys Asn Ala Phe Leu Asn Leu Ala Thr Pro Phe Ile Ala Phe Ser Glu
945             950             955             960

Pro Gly Lys Ala Ser Lys Lys Tyr Arg Asp Ile Glu Phe Thr Leu
            965             970             975

Trp Asp Arg Leu Glu Val Asn Gly Pro Lys Thr Leu Gly Gln Phe Ile
            980             985             990

Glu Trp Ile Glu Thr Gln Thr Gly Leu Thr Val Ser Met Met Ser Ser
            995             1000            1005

Gly Val Ser Leu Leu Tyr Ala Phe Phe Gln Pro Pro Ser Lys Val
    1010            1015            1020

Ala Glu Arg Lys Thr Arg Asp Val Ile Gln Val Val Glu Glu Val
    1025            1030            1035

Ser Arg Asn Lys Val Pro Pro Phe Arg Arg Ser Leu Val Phe Glu
    1040            1045            1050

Ala Ile Thr Gln Asn Asp Lys Asp Glu Asp Val Glu Ile Pro Tyr
    1055            1060            1065

Val Lys Tyr Asn Phe Arg
    1070

<210> SEQ ID NO 17
<211> LENGTH: 1716
<212> TYPE: DNA
<213> ORGANISM: Meloidogyne incognita

<400> SEQUENCE: 17
atgcctccat ctactcgtga agttaaagaa gcccaatatg gatatgttta tggtgtttct      60
gggcctgtcg taacggccga aaagatgtct ggtgctgcca tgtacgaatt agtccgtgtt     120
ggacataatg aacttgttgg tgaaatcatt cgtttggaag ggattatgc aactatacaa     180 gtctacgagg aaacatctgc tgtaacaatt ggagatccag ttttacgtac cggaaagcca     240
ctttcggtag aattaggtcc aggcattatg ggctgtatct tgacggaat caacgtcct     300 ctacacgata ttgcacagat gacccaatct atttatatac ccaaaggaat caatacaaac    360
```

```
gccctcagtc gaacaaaaca atgggaattt attccaaaac aaagtcttcg tccagggat    420 catgttactg gtggtgatat tgtggggata gtctatgaga gtgctttggt taaacactca    480
attatggtgc ctccaaatgc ttgtggaacg ttgaagtttt tggcacctaa agggagctat    540
aatgttacgg aaaaaatcat cgaaatcgaa ttttctggag atgttcaaaa atattctatg    600
cttcaagtct ggcctgtaag acagcctcgc ccagtcgccg aaaaattggc tgccaattat    660 ccactttttgt gtggtcaaag agttttggat gctctattcc cttgtgtaca aggggaacg    720 actgctatac ctggagcttt tggttgtgga aaaacagtaa tttcccaatc attgtcgaaa    780
tacagcaatt ctgacgcaat tatttatgtt ggctgtggag aacgtggcaa cgagatgtcc    840
gaggtattac gtgatttccc agaattaaca atggaagtag atggaaaaac aacctcaatt    900
atggaaagaa cagctttagt agctaatact tctaatatgc ctgtagctgc tagagaagct    960
agtatttata caggaattac tttggctgaa tattttcgtg atatgggttt aaatgttgca   1020
atgatggcag attcaacttc tcgttgggca gaagctttaa gagaaatttc tggacgtttg   1080
ggagaaatgc ctgctgattc tggttatcct gcctatttag ctgctagatt agcttcgttt   1140
tatgaaaggg ctgggaaagt taaatgtcgt ggatcgccgg atagagatgg atctgttact   1200
attgttgggg ctgtttctcc tcccggaggt gattttgctg atccagtaac tacagcaaca   1260
ttaggaattg ttcaagtatt tggggatta gacaaaaaat tggctcaacg aaaacatttt   1320
ccttcaatta attggcttat atcttacagt aattatgta gagcattaga tgattattat   1380
gaaaagaatt tccctgaatt cgtccctctt cgtacaaaat acaagaaat tttacaggag   1440 gaagaagatc tttctgagat tgtccaactt gtaggcaaag cttcattagc tgaatctgac   1500
aaaattactc ttgaagttgc aaaaattatt aaagatgatt cctccaaca aaatggttat   1560 gcaccttatg atcgttttg tccgttttac aaaactgttg gaatgatgaa aaatatgatt   1620 gcatttttatg actttgcccg tcatgcagtt gaatctactg cacaatctga caacaaaatt   1680
acttggaacg tgcacaacgt gattcgcaag gattga                              1716
```

<210> SEQ ID NO 18
<211> LENGTH: 571
<212> TYPE: PRT
<213> ORGANISM: Meloidogyne incognita

<400> SEQUENCE: 18

```
Met Pro Pro Ser Thr Arg Glu Val Lys Glu Ala Gln Tyr Gly Tyr Val
1               5                   10                  15

Tyr Gly Val Ser Gly Pro Val Val Thr Ala Glu Lys Met Ser Gly Ala
            20                  25                  30

Ala Met Tyr Glu Leu Val Arg Val Gly His Asn Glu Leu Val Gly Glu
        35                  40                  45

Ile Ile Arg Leu Glu Gly Asp Tyr Ala Thr Ile Gln Val Tyr Glu Glu
    50                  55                  60

Thr Ser Ala Val Thr Ile Gly Asp Pro Val Leu Arg Thr Gly Lys Pro
65                  70                  75                  80

Leu Ser Val Glu Leu Gly Pro Gly Ile Met Gly Cys Ile Phe Asp Gly
                85                  90                  95

Ile Gln Arg Pro Leu His Asp Ile Ala Gln Met Thr Gln Ser Ile Tyr
            100                 105                 110

Ile Pro Lys Gly Ile Asn Thr Asn Ala Leu Ser Arg Thr Lys Gln Trp
        115                 120                 125

Glu Phe Ile Pro Lys Gln Ser Leu Arg Pro Gly Asp His Val Thr Gly
```

```
              130                 135                 140
Gly Asp Ile Val Gly Ile Val Tyr Glu Ser Ala Leu Val Lys His Ser
145                 150                 155                 160

Ile Met Val Pro Pro Asn Ala Cys Gly Thr Leu Lys Phe Leu Ala Pro
                165                 170                 175

Lys Gly Ser Tyr Asn Val Thr Glu Lys Ile Ile Glu Ile Glu Phe Ser
                    180                 185                 190

Gly Asp Val Gln Lys Tyr Ser Met Leu Gln Val Trp Pro Val Arg Gln
                195                 200                 205

Pro Arg Pro Val Ala Glu Lys Leu Ala Ala Asn Tyr Pro Leu Leu Cys
        210                 215                 220

Gly Gln Arg Val Leu Asp Ala Leu Phe Pro Cys Val Gln Gly Gly Thr
225                 230                 235                 240

Thr Ala Ile Pro Gly Ala Phe Gly Cys Gly Lys Thr Val Ile Ser Gln
                    245                 250                 255

Ser Leu Ser Lys Tyr Ser Asn Ser Asp Ala Ile Ile Tyr Val Gly Cys
                260                 265                 270

Gly Glu Arg Gly Asn Glu Met Ser Glu Val Leu Arg Asp Phe Pro Glu
            275                 280                 285

Leu Thr Met Glu Val Asp Gly Lys Thr Thr Ser Ile Met Glu Arg Thr
        290                 295                 300

Ala Leu Val Ala Asn Thr Ser Asn Met Pro Val Ala Ala Arg Glu Ala
305                 310                 315                 320

Ser Ile Tyr Thr Gly Ile Thr Leu Ala Glu Tyr Phe Arg Asp Met Gly
                    325                 330                 335

Leu Asn Val Ala Met Met Ala Asp Ser Thr Ser Arg Trp Ala Glu Ala
                340                 345                 350

Leu Arg Glu Ile Ser Gly Arg Leu Gly Glu Met Pro Ala Asp Ser Gly
            355                 360                 365

Tyr Pro Ala Tyr Leu Ala Ala Arg Leu Ala Ser Phe Tyr Glu Arg Ala
        370                 375                 380

Gly Lys Val Lys Cys Arg Gly Ser Pro Asp Arg Asp Gly Ser Val Thr
385                 390                 395                 400

Ile Val Gly Ala Val Ser Pro Pro Gly Gly Asp Phe Ala Asp Pro Val
                    405                 410                 415

Thr Thr Ala Thr Leu Gly Ile Val Gln Val Phe Trp Gly Leu Asp Lys
                420                 425                 430

Lys Leu Ala Gln Arg Lys His Phe Pro Ser Ile Asn Trp Leu Ile Ser
            435                 440                 445

Tyr Ser Asn Tyr Met Arg Ala Leu Asp Asp Tyr Tyr Glu Lys Asn Phe
        450                 455                 460

Pro Glu Phe Val Pro Leu Arg Thr Lys Tyr Lys Glu Ile Leu Gln Glu
465                 470                 475                 480

Glu Glu Asp Leu Ser Glu Ile Val Gln Leu Val Gly Lys Ala Ser Leu
                    485                 490                 495

Ala Glu Ser Asp Lys Ile Thr Leu Glu Val Ala Lys Ile Ile Lys Asp
                500                 505                 510

Asp Phe Leu Gln Gln Asn Gly Tyr Ala Pro Tyr Asp Arg Phe Cys Pro
            515                 520                 525

Phe Tyr Lys Thr Val Gly Met Met Lys Asn Met Ile Ala Phe Tyr Asp
        530                 535                 540

Phe Ala Arg His Ala Val Glu Ser Thr Ala Gln Ser Asp Asn Lys Ile
545                 550                 555                 560
```

Thr Trp Asn Val His Asn Val Ile Arg Lys Asp
            565                 570

<210> SEQ ID NO 19
<211> LENGTH: 827
<212> TYPE: DNA
<213> ORGANISM: Meloidogyne incognita

<400> SEQUENCE: 19

```
ctttgctgcg gccgcgggga gcatgtctct caaacaggag cctctgcatc tgcttccggt      60
tcatttccaa ttgttttacc acataatgaa ctaaagcagg acggtggcaa attttatttg     120
gaaggagacg aaaagaatac ctgccttcta tatattgaat cgatttctgt tgtgttatat     180
aacgtaaaac aaaaaatgtc tgcttgggcg accattaatg caacttctaa gggagcaaca     240
tatagtggta aaattgagtg tccagcaact cataatacag acaggagtt  taaaatttca     300 ttgcaagcaa ttgctggcgg tgaaggtgtt tcaggctatt atattggtga taaaaagaaa     360 gtcatttttcc ggttaagcaa agtcgatgtt gatttaatat ttaactttac ttcatcagct     420
tattgggagt tggtgaatgc tgatgttagg acaataagtt tggatggcgc agaagaaggt     480
ggagttccga gtgtcgataa cacctggcga cttgtttctg gtataagcag caacaataaa     540
ggatggattt tcacagataa tcaatctccg gcctggaata ttaatgggtt aaagactac      600 gccttctctt gtggtcgaac tagtccaatt atttgggcaa acatgatac  ggatgaaaaa     660 agcctggaac atgcagttgg tttggctttt cataatttac agtttcaatt gaattcaact     720
tatatttctc cggataaaaa aagaatggca aagtttggct ggcgtgttaa tgattgtgca     780
cctctattaa gtattggtac ttggatgatt cttgtggttg caattat                   827
```

<210> SEQ ID NO 20
<211> LENGTH: 275
<212> TYPE: PRT
<213> ORGANISM: Meloidogyne incognita

<400> SEQUENCE: 20

Leu Cys Cys Gly Arg Gly Glu His Val Ser Gln Thr Gly Ala Ser Ala
1               5                  10                  15

Ser Ala Ser Gly Ser Phe Pro Ile Val Leu Pro His Asn Glu Leu Lys
            20                  25                  30

Gln Asp Gly Gly Lys Phe Tyr Leu Glu Gly Asp Glu Lys Asn Thr Cys
        35                  40                  45

Leu Leu Tyr Ile Glu Ser Ile Ser Val Val Leu Tyr Asn Val Lys Gln
    50                  55                  60

Lys Met Ser Ala Trp Ala Thr Ile Asn Ala Thr Ser Lys Gly Ala Thr
65                  70                  75                  80

Tyr Ser Gly Lys Ile Glu Cys Pro Ala Thr His Asn Thr Gly Gln Glu
                85                  90                  95

Phe Lys Ile Ser Leu Gln Ala Ile Ala Gly Gly Glu Gly Val Ser Gly
            100                 105                 110

Tyr Tyr Ile Gly Asp Lys Lys Val Ile Phe Arg Leu Ser Lys Val
        115                 120                 125

Asp Val Asp Leu Ile Phe Asn Phe Thr Ser Ala Tyr Trp Glu Leu
    130                 135                 140

Val Asn Ala Asp Val Arg Thr Ile Ser Leu Asp Gly Ala Glu Glu Gly
145                 150                 155                 160

Gly Val Pro Ser Val Asp Asn Thr Trp Arg Leu Val Ser Gly Ile Ser

```
                    165                 170                 175
Ser Asn Asn Lys Gly Trp Ile Phe Thr Asp Asn Gln Ser Pro Ala Trp
            180                 185                 190

Asn Ile Asn Gly Phe Lys Asp Tyr Ala Phe Ser Cys Gly Arg Thr Ser
            195                 200                 205

Pro Ile Ile Trp Ala Lys His Asp Thr Asp Glu Lys Ser Leu Glu His
            210                 215                 220

Ala Val Gly Leu Ala Phe His Asn Leu Gln Phe Gln Leu Asn Ser Thr
225                 230                 235                 240

Tyr Ile Ser Pro Asp Lys Lys Arg Met Ala Lys Phe Gly Trp Arg Val
            245                 250                 255

Asn Asp Cys Ala Pro Leu Leu Ser Ile Gly Thr Trp Met Ile Leu Val
            260                 265                 270

Val Ala Ile
        275

<210> SEQ ID NO 21
<211> LENGTH: 3510
<212> TYPE: DNA
<213> ORGANISM: Meloidogyne incognita

<400> SEQUENCE: 21
atggttacaa aaattccaac ttttccccctc cttttttattt tcccattatt atttacattt       60
ttaaccacaa aatgtcaggc ttattctata ccattaatat cagaatgtaa ttcggaagaa      120
gccccagttt ttcttttgca acggaatgtt tcttctatcg ccggaactga gcctttaaga      180
actgttcctg ttactggggg attttttggaa tgtgcggaac tttgctcagc agcaaataat      240
tgtgttgccg ttaaattctc tattgaaaaa caatgccaat tattggggaa acaacaacg       300 acaacaacaa ctttatcttt acaagacatt aatttaacac aagctagatt agctactaaa      360
agttgtgtga agagcaaaaa aatttgttct tccccccttcc attttgatgt tcacgaacaa      420
aaaatacttg ttggtttttgc tagagaagtt gtatcagcag aatctataca tcaatgttta      480
actgcttgtt tagatgctgt tgatactttt ggctttgaat gcgagtcagt aatgtattat      540
ccattggatg ccgaatgtat tttaaataca gaagacagac ttgaccgtcc agatttgttt      600
gttgatgaga aggaggatac tgttgtttat ttggataata attgtgctgg atcccaatgt      660
catgcctctt atgtaaccca atatgtagct gttgaaggaa aacaattagc cgaggaattg      720
gatcataatt tgatggaat ggaattgaca gaatgtgaac aactttgtaa tcaaagattg      780
agtgtttctg caaatgactt caattgcaaa gcatttatgt acaataacca aacaagatct      840
tgtattcttt ctgatgaacg ttcaagacct tgggtagag ctaatttgac agatgctaaa      900
ggatggactt atcacgagaa aaaatgtttt gcctctcctc gaacttgccg aaatgttcct      960
tcatttaccc gcgtccctca aatgttatta gttggatttg cctctttgt aatggaaaat     1020 gtcccttcag taactatgtg tttggatcaa tgtacaaatc ctccaccaga aactggacaa     1080
agttttgttt gtaaatctgt catgtattat tataatgagc aagaatgtat tttaaatgct     1140
gaatcacgtc attccaagcc agatttattt attcccgaag aagacgattt tgttgtagat     1200
tattttgata taaaattgccg tctagaacaa gaacaatgta tcgatggaag aacaccccaa     1260
ttagttagaa caattaattc tgcacttcca gaaggggagg ggtctataca tgttttggaa     1320
acaattaagg gaggagttca gcaatgtgct aaaaagtgtt ttgaacacgc cccagacaaa     1380
tgtcgttctt tcaattttga taaacaagct ggtaattgta atttactta tttggatgga     1440
```

| | | |
|---|---|---|
| caagggtctt tacgaccaga gcaaaagaca caatttgatt tatacgatgt tcactgtttg | 1500 |
| agtgggacat ctcaactttt aggagaaaat tctaaacatt ctccctctgc ttgtgttgac | 1560 |
| ccagaagggg ctattttag tcgtttcctc tacactcgtt gggtagcaaa ttctcccaat | 1620 |
| cgtgaaattt caagtttatc actttccaaa tgtttaaatc tttgttcggt tggaggagaa | 1680 |
| caatgtgaag gtgttaatta caatcgtcga aatggttctt gtcaattatt tacttccctt | 1740 |
| ctattaaatt cttctccaaa ttctcaacaa gacaaagacg aacatgttga tttttacaga | 1800 |
| aatatttgta gagttaagga atcgaaaagt gatagtgggg ctgctaatgt acccaaaaca | 1860 |
| caacaagcaa cggctgcacc tcccccttct gttcaattaa ctactaaacc tccacaaatt | 1920 |
| cgtgatttaa acaacaacaa taaaacaaca cacaagaac caaatattaa acttccacca | 1980 |
| caatcagcaa aacctataaa tggaaaaact ggaaaggaac aacttcctgt agggtcaaaa | 2040 |
| tcttttgggg ttactaatac gcgtgatgat ggggagaatt caataactgg aactgctcct | 2100 |
| cctcctgtag atggcaaatt aattattaaa ccttcaccac aagtttctat tccctcccct | 2160 |
| gtacttattc cggcacaaga agtacatact atttgtaatt atgaaggaat tagtgttcaa | 2220 |
| attaaacatt cttctccatt ctctggcgtt gttttgttc gaaataaata tgatacttgc | 2280 |
| cgtgtgaagt tgaaggaaag gacagcgttg ttttggtttt ggggcttcca gcaaattttg | 2340 |
| gaaatgaagc caattgcttt aattaattca caaaaacatg gaaaagggaa taaaacacac | 2400 |
| ggagatactt tactttctat tgaaggttcc aaaaaacaaa ttgaagggg ttcttcaact | 2460 |
| gaagatattc aattaataaa ttctcaaaaa gaccttaaac gttcaagaag acaattacaa | 2520 |
| agagattgtg gattacaaga tatggacaat ggaacttaca aaactgttat tgttgtccaa | 2580 |
| acaaataatt tgggaattcc gggacttgtt acttctatgg accaactta tgagatttcc | 2640 |
| tgtaactatt caagtatgtt gggaggcaaa gtccagacag cagctgcatt acgtgttcac | 2700 |
| ggtccccaac cttcactaat ccagcctcgc ggcaaaatag aattgggaaa tcctgttttg | 2760 |
| atgcaaatgg ggcctgtacg tagtgaaagg caaagtgggg aagggccttt aattcaagct | 2820 |
| aaattgggag atattcttga attaaaatgg gaaattatgg caatggatga agaattggac | 2880 |
| tttttagttc gtgattgttt tgcagagccg ggaacttctg gaaatcaagg ggaaagactt | 2940 |
| cctttaattg agaatggttg tccaacacca gcagtagcac aaaaattaat tccaaatcca | 3000 |
| ataaaagcaa ttaattctgc agttaaatta acttatttac aagcattcag atttgacagt | 3060 |
| tctccagcta ttagaataac ttgtcatta gaattatgta agaaaattg taaatcggtt | 3120 |
| aattgtaaat ttaatgatgg aattaaagaa tcgtggggca gaaaacgccg ttttgctatt | 3180 |
| gacaataaca ttaataggaa aaatgaagtt aaagaattcg aaactcgccg ttttgtcgtt | 3240 |
| ccccgttttg cccaagcaac aacttcttta gttattgtag acccttaca acaacaaat | 3300 |
| tctgttataa aaacagaaca acaacaacaa ccatttattt cacattcctc aatatctaaa | 3360 |
| caaatatttg aaaataataa aatataaca aaaacagcta aaaaatcctc ttctcttttt | 3420 |
| gaagctttta ctgaggctgc tggtggaagg aaaattaatt tagaattaac aacaacaaat | 3480 |
| tcagaacaac aacaactttt gtttacataa | 3510 |

<210> SEQ ID NO 22
<211> LENGTH: 1169
<212> TYPE: PRT
<213> ORGANISM: Meloidogyne incognita

<400> SEQUENCE: 22

Met Val Thr Lys Ile Pro Thr Phe Pro Leu Leu Phe Ile Phe Pro Leu

```
1               5                    10                   15
Leu Phe Thr Phe Leu Thr Thr Lys Cys Gln Ala Tyr Ser Ile Pro Leu
                20                  25                  30

Ile Ser Glu Cys Asn Ser Glu Glu Ala Pro Val Phe Leu Leu Gln Arg
                35                  40                  45

Asn Val Ser Ser Ile Ala Gly Thr Glu Pro Leu Arg Thr Val Pro Val
            50                  55                  60

Thr Gly Gly Phe Leu Glu Cys Ala Glu Leu Cys Ser Ala Ala Asn Asn
65                  70                  75                  80

Cys Val Ala Val Lys Phe Ser Ile Glu Lys Gln Cys Gln Leu Leu Gly
                85                  90                  95

Lys Thr Thr Thr Thr Thr Thr Thr Leu Ser Leu Gln Asp Ile Asn Leu
                100                 105                 110

Thr Gln Ala Arg Leu Ala Thr Lys Ser Cys Val Lys Ser Lys Lys Ile
            115                 120                 125

Cys Ser Ser Pro Phe His Phe Asp Val His Glu Gln Lys Ile Leu Val
            130                 135                 140

Gly Phe Ala Arg Glu Val Val Ser Ala Glu Ser Ile His Gln Cys Leu
145                 150                 155                 160

Thr Ala Cys Leu Asp Ala Val Asp Thr Phe Gly Phe Glu Cys Glu Ser
                165                 170                 175

Val Met Tyr Tyr Pro Leu Asp Ala Glu Cys Ile Leu Asn Thr Glu Asp
                180                 185                 190

Arg Leu Asp Arg Pro Asp Leu Phe Val Asp Glu Lys Glu Asp Thr Val
            195                 200                 205

Val Tyr Leu Asp Asn Asn Cys Ala Gly Ser Gln Cys His Ala Ser Tyr
210                 215                 220

Val Thr Gln Tyr Val Ala Val Glu Gly Lys Gln Leu Ala Glu Glu Leu
225                 230                 235                 240

Asp His Asn Phe Asp Gly Met Glu Leu Thr Glu Cys Glu Gln Leu Cys
                245                 250                 255

Asn Gln Arg Leu Ser Val Ser Ala Asn Asp Phe Asn Cys Lys Ala Phe
            260                 265                 270

Met Tyr Asn Asn Gln Thr Arg Ser Cys Ile Leu Ser Asp Glu Arg Ser
            275                 280                 285

Arg Pro Leu Gly Arg Ala Asn Leu Thr Asp Ala Lys Gly Trp Thr Tyr
            290                 295                 300

His Glu Lys Lys Cys Phe Ala Ser Pro Arg Thr Cys Arg Asn Val Pro
305                 310                 315                 320

Ser Phe Thr Arg Val Pro Gln Met Leu Leu Val Gly Phe Ala Ser Phe
                325                 330                 335

Val Met Glu Asn Val Pro Ser Val Thr Met Cys Leu Asp Gln Cys Thr
                340                 345                 350

Asn Pro Pro Pro Glu Thr Gly Gln Ser Phe Val Cys Lys Ser Val Met
            355                 360                 365

Tyr Tyr Tyr Asn Glu Gln Glu Cys Ile Leu Asn Ala Glu Ser Arg His
            370                 375                 380

Ser Lys Pro Asp Leu Phe Ile Pro Glu Glu Asp Phe Val Val Asp
385                 390                 395                 400

Tyr Phe Asp Ile Asn Cys Arg Leu Glu Gln Glu Gln Cys Ile Asp Gly
                405                 410                 415

Arg Thr Pro Gln Leu Val Arg Thr Ile Asn Ser Ala Leu Pro Glu Gly
            420                 425                 430
```

```
Glu Gly Ser Ile His Val Leu Glu Thr Ile Lys Gly Val Gln Gln
        435                 440                 445

Cys Ala Lys Lys Cys Phe Glu His Ala Pro Asp Lys Cys Arg Ser Phe
    450                 455                 460

Asn Phe Asp Lys Gln Ala Gly Asn Cys Asn Leu Leu Tyr Leu Asp Gly
465                 470                 475                 480

Gln Gly Ser Leu Arg Pro Glu Gln Lys Thr Gln Phe Asp Leu Tyr Asp
                485                 490                 495

Val His Cys Leu Ser Gly Thr Ser Gln Leu Leu Gly Glu Asn Ser Lys
            500                 505                 510

His Ser Pro Ser Ala Cys Val Asp Pro Glu Gly Ala Ile Phe Ser Arg
        515                 520                 525

Phe Leu Tyr Thr Arg Trp Val Ala Asn Ser Pro Asn Arg Glu Ile Ser
    530                 535                 540

Ser Leu Ser Leu Ser Lys Cys Leu Asn Leu Cys Ser Val Gly Gly Glu
545                 550                 555                 560

Gln Cys Glu Gly Val Asn Tyr Asn Arg Arg Asn Gly Ser Cys Gln Leu
                565                 570                 575

Phe Thr Ser Leu Leu Asn Ser Ser Pro Asn Ser Gln Gln Asp Lys
            580                 585                 590

Asp Glu His Val Asp Phe Tyr Arg Asn Ile Cys Arg Val Lys Glu Ser
        595                 600                 605

Lys Ser Asp Ser Gly Ala Ala Asn Val Pro Lys Thr Gln Gln Ala Thr
    610                 615                 620

Ala Ala Pro Pro Pro Ser Val Gln Leu Thr Thr Lys Pro Pro Gln Ile
625                 630                 635                 640

Arg Asp Leu Asn Asn Asn Lys Thr Thr His Lys Glu Pro Asn Ile
                645                 650                 655

Lys Leu Pro Pro Gln Ser Ala Lys Pro Ile Asn Gly Lys Thr Gly Lys
            660                 665                 670

Glu Gln Leu Pro Val Gly Ser Lys Ser Phe Gly Val Thr Asn Thr Arg
        675                 680                 685

Asp Asp Gly Glu Asn Ser Ile Thr Gly Thr Ala Pro Pro Pro Val Asp
    690                 695                 700

Gly Lys Leu Ile Ile Lys Pro Ser Pro Gln Val Ser Ile Pro Ser Pro
705                 710                 715                 720

Val Leu Ile Pro Ala Gln Glu Val His Thr Ile Cys Asn Tyr Glu Gly
                725                 730                 735

Ile Ser Val Gln Ile Lys His Ser Ser Pro Phe Ser Gly Val Val Phe
            740                 745                 750

Val Arg Asn Lys Tyr Asp Thr Cys Arg Val Lys Leu Lys Glu Arg Thr
        755                 760                 765

Ala Leu Phe Trp Phe Trp Gly Phe Gln Gln Ile Leu Glu Met Lys Pro
    770                 775                 780

Ile Ala Leu Ile Asn Ser Gln Lys His Gly Lys Gly Asn Lys Thr His
785                 790                 795                 800

Gly Asp Thr Leu Leu Ser Ile Glu Gly Ser Lys Lys Gln Ile Glu Gly
                805                 810                 815

Gly Ser Ser Thr Glu Asp Ile Gln Leu Ile Asn Ser Gln Lys Asp Leu
            820                 825                 830

Lys Arg Ser Arg Arg Gln Leu Gln Arg Asp Cys Gly Leu Gln Asp Met
        835                 840                 845
```

Asp Asn Gly Thr Tyr Lys Thr Val Ile Val Val Gln Thr Asn Asn Leu
    850                 855                 860

Gly Ile Pro Gly Leu Val Thr Ser Met Asp Gln Leu Tyr Glu Ile Ser
865                 870                 875                 880

Cys Asn Tyr Ser Ser Met Leu Gly Gly Lys Val Gln Thr Ala Ala Ala
                885                 890                 895

Leu Arg Val His Gly Pro Gln Pro Ser Leu Ile Gln Pro Arg Gly Lys
            900                 905                 910

Ile Glu Leu Gly Asn Pro Val Leu Met Gln Met Gly Pro Val Arg Ser
        915                 920                 925

Glu Arg Gln Ser Gly Glu Gly Pro Leu Ile Gln Ala Lys Leu Gly Asp
    930                 935                 940

Ile Leu Glu Leu Lys Trp Glu Ile Met Ala Met Asp Glu Glu Leu Asp
945                 950                 955                 960

Phe Leu Val Arg Asp Cys Phe Ala Glu Pro Gly Thr Ser Gly Asn Gln
                965                 970                 975

Gly Glu Arg Leu Pro Leu Ile Glu Asn Gly Cys Pro Thr Pro Ala Val
            980                 985                 990

Ala Gln Lys Leu Ile Pro Asn Pro  Ile Lys Ala Ile Asn  Ser Ala Val
        995                 1000                1005

Lys Leu  Thr Tyr Leu Gln Ala  Phe Arg Phe Asp Ser  Ser Pro Ala
    1010                1015                1020

Ile Arg  Ile Thr Cys His Leu  Glu Leu Cys Lys Glu  Asn Cys Lys
    1025                1030                1035

Ser Val  Asn Cys Lys Phe Asn  Asp Gly Ile Lys Glu  Ser Trp Gly
    1040                1045                1050

Arg Lys  Arg Arg Phe Ala Ile  Asp Asn Asn Ile Asn  Arg Lys Asn
    1055                1060                1065

Glu Val  Lys Glu Phe Glu Thr  Arg Arg Phe Val Val  Pro Arg Phe
    1070                1075                1080

Ala Gln  Ala Thr Thr Ser Leu  Val Ile Val Asp Pro  Leu Gln Gln
    1085                1090                1095

Gln Asn  Ser Val Ile Lys Thr  Glu Gln Gln Gln Gln  Pro Phe Ile
    1100                1105                1110

Ser His  Ser Ser Ile Ser Lys  Gln Ile Phe Glu Asn  Asn Lys Asn
    1115                1120                1125

Ile Thr  Lys Thr Ala Lys Lys  Ser Ser Ser Leu Phe  Glu Ala Phe
    1130                1135                1140

Thr Glu  Ala Ala Gly Gly Arg  Lys Ile Asn Leu Glu  Leu Thr Thr
    1145                1150                1155

Thr Asn  Ser Glu Gln Gln Gln  Leu Leu Phe Thr
    1160                1165

<210> SEQ ID NO 23
<211> LENGTH: 815
<212> TYPE: DNA
<213> ORGANISM: Meloidogyne incognita

<400> SEQUENCE: 23
atgtttcgaa atcagtatga tagtgatgtg actgttttta gtcctcaggg acgtttacat    60
caaaacgatt atgcagttga agcaatgcgt caaggcagtg ctactgttgc tttgcatgga   120
aaagatcatg ctgttgttgt tgctcttatg cgttctcaaa gcgaattatc ctcttatcaa   180
tcaaagatat ttgaattgga tggtcatgtg ggtctttcaa tgtctggtct tttagcggat   240

```
ggcagaattt tagcccgatt tattcaaaat gaatgtgcta ctttcttttc ggaattgcaa    300
acaccattgc cgatggagaa tttgcgtaca aaactaactt tgagaatgca agagaatatt    360
caggtttatg ggaaacggcc atttggagtt ggattgttaa ttattggata tgatgactct    420
ggtcctcatg ttcttaatgc tgatccatct gctaatgtta caatggttaa agctgcttca    480
attgggctc gttctcaatc tgctcgtact tatttggaaa acattttga cgaatatgca    540
aatagtactg accaaaaaaa tgttattcgt catgctcttc ttgctcttaa agaaactctt    600
cagacaaata ctaaattgga tgagaataat actgcaattg caattgtggg taaacgatgc    660
aagtttggtt gccttccatc agagcaagtt aaagaaatta ttgcaagtct taacaacaat    720
caagctccag agccaatgca gctttgaaaa ttgtgctgac ttgcgcggat atttgtctaa    780
ataattttt tttgattttc aacaatcttg tttga                                815

<210> SEQ ID NO 24
<211> LENGTH: 248
<212> TYPE: PRT
<213> ORGANISM: Meloidogyne incognita

<400> SEQUENCE: 24

Met Phe Arg Asn Gln Tyr Asp Ser Asp Val Thr Val Phe Ser Pro Gln
1               5                   10                  15

Gly Arg Leu His Gln Asn Asp Tyr Ala Val Glu Ala Met Arg Gln Gly
            20                  25                  30

Ser Ala Thr Val Ala Leu His Gly Lys Asp His Ala Val Val Val Ala
        35                  40                  45

Leu Met Arg Ser Gln Ser Glu Leu Ser Ser Tyr Gln Ser Lys Ile Phe
    50                  55                  60

Glu Leu Asp Gly His Val Gly Leu Ser Met Ser Gly Leu Leu Ala Asp
65                  70                  75                  80

Gly Arg Ile Leu Ala Arg Phe Ile Gln Asn Glu Cys Ala Thr Phe Phe
                85                  90                  95

Ser Glu Leu Gln Thr Pro Leu Pro Met Glu Asn Leu Arg Thr Lys Leu
            100                 105                 110

Thr Leu Arg Met Gln Glu Asn Ile Gln Val Tyr Gly Lys Arg Pro Phe
        115                 120                 125

Gly Val Gly Leu Leu Ile Ile Gly Tyr Asp Asp Ser Gly Pro His Val
    130                 135                 140

Leu Asn Ala Asp Pro Ser Ala Asn Val Thr Met Val Lys Ala Ala Ser
145                 150                 155                 160

Ile Gly Ala Arg Ser Gln Ser Ala Arg Thr Tyr Leu Glu Lys His Phe
                165                 170                 175

Asp Glu Tyr Ala Asn Ser Thr Asp Gln Lys Asn Val Ile Arg His Ala
            180                 185                 190

Leu Leu Ala Leu Lys Glu Thr Leu Gln Thr Asn Thr Lys Leu Asp Glu
        195                 200                 205

Asn Asn Thr Ala Ile Ala Ile Val Gly Lys Arg Cys Lys Phe Gly Cys
    210                 215                 220

Leu Pro Ser Glu Gln Val Lys Glu Ile Ile Ala Ser Leu Asn Asn Asn
225                 230                 235                 240

Gln Ala Pro Glu Pro Met Gln Leu
                245

<210> SEQ ID NO 25
<211> LENGTH: 690
```

<212> TYPE: DNA
<213> ORGANISM: Meloidogyne incognita

<400> SEQUENCE: 25

```
aattaaatgc aagaactgca agaagaaact gttgaaaata gcaacaataa ggaggatatt      60
gagactttca aagaattggg aataaatgaa gaattgtgca gtgcttgtga acgtattggt     120
tggaaaaaac ctatgcctat acaacaaaaa gttattccga ttgccttgaa gggaagagat     180
gtgattggat tggcagaaac tggttctggc aaaactgcag catttgctct tccaatactt     240
caatccttaa tgtccaatcc acagcgtctc tttgccgttg tattagctcc tacgagagaa     300
ttggcatttc aaatttcgga tcagtttgtg gctttaggtg caactatcgg cctccaagtt     360
tctacaattg tcggtggtat tgatatgtca acacagacat tgtctctttc taaaaggcct     420
catgttattg ttgcaactcc tggtcggctt gttgaccacc tcgaaaacac caaaggtttt     480
gatcttcgat cagtcaaata tttggttttg gacgaagcgg atagaatact taatatggac     540
tttgaattgg aattggataa aattcttaaa gttattccaa atacaaggca tacatttta      600
ttttcggcaa ctatgacgca caaggtttca aaattagaaa gggcccattt aaagaagcct     660
gttcgtgttg aattatctac caaatatcaa                                      690
```

<210> SEQ ID NO 26
<211> LENGTH: 228
<212> TYPE: PRT
<213> ORGANISM: Meloidogyne incognita

<400> SEQUENCE: 26

```
Met Gln Glu Leu Gln Glu Thr Val Glu Asn Ser Asn Asn Lys Glu
1               5                   10                  15

Asp Ile Glu Thr Phe Lys Glu Leu Gly Ile Asn Glu Glu Leu Cys Ser
            20                  25                  30

Ala Cys Glu Arg Ile Gly Trp Lys Lys Pro Met Pro Ile Gln Gln Lys
        35                  40                  45

Val Ile Pro Ile Ala Leu Lys Gly Arg Asp Val Ile Gly Leu Ala Glu
    50                  55                  60

Thr Gly Ser Gly Lys Thr Ala Ala Phe Ala Leu Pro Ile Leu Gln Ser
65                  70                  75                  80

Leu Met Ser Asn Pro Gln Arg Leu Phe Ala Val Val Leu Ala Pro Thr
                85                  90                  95

Arg Glu Leu Ala Phe Gln Ile Ser Asp Gln Phe Val Ala Leu Gly Ala
            100                 105                 110

Thr Ile Gly Leu Gln Val Ser Thr Ile Val Gly Gly Ile Asp Met Ser
        115                 120                 125

Thr Gln Thr Leu Ser Leu Ser Lys Arg Pro His Val Ile Val Ala Thr
    130                 135                 140

Pro Gly Arg Leu Val Asp His Leu Glu Asn Thr Lys Gly Phe Asp Leu
145                 150                 155                 160

Arg Ser Val Lys Tyr Leu Val Leu Asp Glu Ala Asp Arg Ile Leu Asn
                165                 170                 175

Met Asp Phe Glu Leu Glu Leu Asp Lys Ile Leu Lys Val Ile Pro Asn
            180                 185                 190

Thr Arg His Thr Phe Leu Phe Ser Ala Thr Met Thr His Lys Val Ser
        195                 200                 205

Lys Leu Glu Arg Ala His Leu Lys Pro Val Arg Val Glu Leu Ser
    210                 215                 220
```

Thr Lys Tyr Gln
225

<210> SEQ ID NO 27
<211> LENGTH: 799
<212> TYPE: DNA
<213> ORGANISM: Meloidogyne incognita

<400> SEQUENCE: 27

```
ggcgcgcctc agcagtcgct gtcgttaccc ctgttcaaca attctagttc caggttcaaa    60
ttggcattgt tccaaagcat cagcaacatt tgcacgttcc cacttgtcaa gatcggcaag   120
aattgaaact ttcgacaaaa attcgtcata cattttcttt ttgcgcattg tagatcccat   180
taaaatagct ctataggtga gtcggtcaat agcccaaagt ttgactgttg ggtcttagc    240 tacaacagta gcagcacgtg gagttccata aattaaggca agttcaccaa agaaccccc    300 ttccttaact gagagaacaa attcccaagt actccgatcg cgttaacgct ttatcacgat   360
accttctacc acatatcact aacaacatca acactcatca ctctcgacga catccactcg   420
atcactactc tcacacgacc gattaactcc tcatccacgc ggccgcctgc gggaatttgt   480
tctctcagtt aaggaagggg gttcttttgg tgaacttgcc ttaatttatg gaactccacg   540
tgctgctact gttgtagcta agaccccaac agtcaaactt tgggctattg accgactcac   600
ctatagagct attttaatgg gatctacaat gcgcaaaaga aaatgtatg acgaattttt    660 gtcgaaagtt tcaattcttg ccgatcttga caagtgggaa cgtgcaaatg ttgctgatgc   720
tttggaacaa tgccaatttg aacctggaac tagaattgtt gaacaggtag aacccagcgg   780
tactcgctga ggcgatcgc                                               799
```

<210> SEQ ID NO 28
<211> LENGTH: 832
<212> TYPE: DNA
<213> ORGANISM: Meloidogyne incognita

<400> SEQUENCE: 28

```
ggcgcgcctc agcagtcgct gtcgttacct tcacgcactg ggcccataac gcgctcgaat    60
cgagctctat ccaactttac acacttaagg gccccttttaa ccacaacggt tgctgcacgt   120
ggatgatcca ataaaagagc aatttcgcca aaataatcag aaggacccaa tttgccaaca   180
acttcataag gagcatcatc attcggccgt tgtagcacct cggcctctcc ctcaacaatt   240
ataaagaatt catctccggg ttggccctgt tcaacaattc tagttccagg ttcaaattgg   300
cattgttcca agcatcagc aacatttgca cgttcccact aagtactccg atcgcgttaa   360
cgctttatca cgataccttc taccacatat cactaacaac atcaacactc atcactctcg   420
acgacatcca ctcgatcact actctcacac gaccgattaa ctcctcatcc acgcggccgc   480
ctgcaggagc agtgggaacg tgcaaatgtt gctgatgctt tggaacaatg ccaatttgaa   540
cctggaacta gaattgttga acaggccaa cccgagatg aattctttat aattgttgag   600
ggagaggccg aggtgctaca acggccgaat gatgatgctc cttatgaagt tgttggcaaa   660
ttgggtcctt ctgattattt tggcgaaatt gctctttat tggatcatcc acgtgcagca   720
accgttgtgg ttaaagggcc ccttaagtgt gtaaagttgg atagagctcg attcgagcgc   780
gttatgggcc agtgcgtgaa tagaacccag cggtactcgc tgaggcgatc gc           832
```

<210> SEQ ID NO 29
<211> LENGTH: 781
<212> TYPE: DNA

<213> ORGANISM: Meloidogyne incognita

<400> SEQUENCE: 29

| | |
|---|---|
| ggcgcgcctc agcagtcgct gtcgttaccg tgcgtcatag ttgccgaaaa taaaaatgta | 60 |
| tgccttgtat ttggaataac tttaagaatt ttatccaatt ccaattcaaa gtccatatta | 120 |
| agtattctat ccgcttcgtc caaaaccaaa tatttgactg atcgaagatc aaaacctttg | 180 |
| gtgttttcga ggtggtcaac aagccgacca ggagttgcaa caataacatg aggccttta | 240 |
| gaaagagaca atgtctgtgt tgacatatca ataccaccga caattgtaga aacttggagg | 300 |
| ccgatagttg caccaagtac tccgatcgcg ttaacgcttt atcacgatac cttctaccac | 360 |
| atatcactaa caacatcaac actcatcact ctcgacgaca tccactcgat cactactctc | 420 |
| acacgaccga ttaactcctc atccacgcgg ccgcctgcag gagcggtgca actatcggcc | 480 |
| tccaagtttc tacaattgtc ggtggtattg atatgtcaac acagacattg tctctttcta | 540 |
| aaaggcctca tgttattgtt gcaactcctg gtcggcttgt tgaccacctc gaaaacacca | 600 |
| aaggttttga tcttcgatca gtcaaatatt tggttttgga cgaagcggat agaatactta | 660 |
| atatggactt tgaattggaa ttggataaaa ttcttaaagt tattccaaat acaaggcata | 720 |
| cattttatt ttcggcaact atgacgcact agaacccagc ggtactcgct gaggcgatcg | 780 |
| c | 781 |

<210> SEQ ID NO 30
<211> LENGTH: 775
<212> TYPE: DNA
<213> ORGANISM: Meloidogyne incognita

<400> SEQUENCE: 30

| | |
|---|---|
| ggcgcgcctc agcagtcgct gtcgttaccc gccaatggaa acgttgccga gaaaagcata | 60 |
| atttggcgct ctcttggtaa gtagctgatc atcttatcga gagcaccttg aaaatcgatc | 120 |
| gaaagtagtt tgtcggcttc atccaagaca agcatcttgc agaggctcac atcagcaaca | 180 |
| gtcttctcga tgagatccaa gattcgtccg ggagttgcca caatcagatg aacggttcca | 240 |
| ttgagacgca taatgtcgtc acgcaaatcc gtaccgccag ttgtaaccat caccttgaca | 300 |
| ttcatatgct ttccaagtac tccgatcgcg ttaacgcttt atcacgatac cttctaccac | 360 |
| atatcactaa caacatcaac actcatcact ctcgacgaca tccactcgat cactactctc | 420 |
| acacgaccga ttaactcctc atccacgcgg ccgcctgcgg aaagcatatg aatgtcaagg | 480 |
| tgatggttac aactggcggt acggatttgc gtgacgacat tatgcgtctc aatggaaccg | 540 |
| ttcatctgat tgtggcaact cccggacgaa tcttggatct catcgagaag actgttgctg | 600 |
| atgtgagcct ctgcaagatg cttgtcttgg atgaagccga caaactactt tcgatcgatt | 660 |
| ttcaaggtgc tctcgataag atgatcagct acttaccaag agagcgccaa attatgcttt | 720 |
| tctcggcaac gtttccattg gcgtagaacc cagcggtact cgctgaggcg atcgc | 775 |

<210> SEQ ID NO 31
<211> LENGTH: 731
<212> TYPE: DNA
<213> ORGANISM: Meloidogyne incognita

<400> SEQUENCE: 31

| | |
|---|---|
| ggcgcgcctc agcagtcgct gtcgttacct tacatgcagg gcagaggtct ttgcctttca | 60 |
| cagccatttt caaagcatca tttttgttcat caatttgatt aactatcata ataaaattat | 120 |
| ttacagactt atctactttt tttaaacaat ctttggaggg aagttttgt attttaacta | 180 |

```
gcaattgcag catttctgta tttatttgat caattgctgg gcgtaagtct gttgttaaat      240
ttcgaacttt aataagtggt atgcctgatt gattccataa attaaccaaa taaagtactc      300
cgatcgcgtt aacgctttat cacgatacct tctaccacat atcactaaca acatcaacac      360
tcatcactct cgacgacatc cactcgatca ctactctcac acgaccgatt aactcctcat      420
ccacgcggcc gcctgctatt tggttaattt atggaatcaa tcaggcatac cacttattaa      480
agttcgaaat ttaacaacag acttacgccc agcaattgat caaataaata cagaaatgct      540
gcaattgcta gttaaaatac aaaaacttcc ctccaaagat tgtttaaaaa agtagataa       600 gtctgtaaat aattttatta tgatagttaa tcaaattgat gaacaaaatg atgctttgaa      660
aatggctgtg aaaggcaaag acctctgccc tgcatgtaat agaacccagc ggtactcgct      720
gaggcgatcg c                                                           731
```

<210> SEQ ID NO 32
<211> LENGTH: 727
<212> TYPE: DNA
<213> ORGANISM: Meloidogyne incognita

<400> SEQUENCE: 32

```
ggcgcgcctc agcagtcgct gtcgttaccc tttagaagca atcccgcact gattgtcttt       60
gtttcgagac attcgaatat acccattttc tccccaatgt tccccccaac tattttttaac     120 aagccaataa tctccgtgga tgtcatctgt gccgtatcca acaactaaga caccatgatc      180
gagattatcg ggactgcaag cctcctcatc ataaactccg tgagtataaa gttgaaaact      240
gcgatggcca gcatcaattg ctacagaaat tgggccttgt gtggcaacag aagtactccg      300
atcgcgttaa cgctttatca cgatacctc taccacatat cactaacaac atcaacactc       360
atcactctcg acgacatcca ctcgatcact actctcacac gaccgattaa ctcctcatcc      420
acgcggccgc ctgcctgttg ccacacaagg cccaatttct gtagcaattg atgctggcca     480
tcgcagtttt caactttata ctcacggagt ttatgatgag gaggcttgca gtcccgataa      540
tctcgatcat ggtgtcttag ttgttggata cggcacagat gacatccacg agattattg      600 gcttgttaaa aatagttggg gggaacattg gggagaaaat gggtatattc gaatgtctcg      660
aaacaaagac aatcaatgcg ggattgcttc taaagtagaa cccagcggta ctcgctgagg      720
cgatcgc                                                               727
```

<210> SEQ ID NO 33
<211> LENGTH: 531
<212> TYPE: DNA
<213> ORGANISM: Meloidogyne incognita

<400> SEQUENCE: 33

```
ggcgcgcctc agcagtcgct gtcgttacct cttcaattat ttcctccagg atttggccca       60
ctaggctttt tgcctgcatc cacaaatgag acagacaaaa gcattaaagt aaccattaaa      120
ggcattaaat aaataattaa atttttaatt gaattagtaa acatttttt gattgaagaa       180 taattaactt taaagtactc cgatcgcgtt aacgctttat cacgatacct tctaccacat      240
atcactaaca acatcaacac tcatcactct cgacgacatc cactcgatca ctactctcac      300
acgaccgatt aactcctcat ccacgcggcc gcctgctaaa gttaattatt cttcaatcaa      360
aaaaatgttt actaattcaa ttaaaaattt aattatttat ttaatgcctt taatggttac      420
tttaatgctt ttgtctgtct catttgtgga tgcaggcaaa agcctagtg ggccaaatcc       480
```

```
tggaggaaat aattgaagat agaacccagc ggtactcgct gaggcgatcg c      531
```

<210> SEQ ID NO 34
<211> LENGTH: 531
<212> TYPE: DNA
<213> ORGANISM: Arabidopsis thaliana

<400> SEQUENCE: 34

```
ggcgcgcctc agcagtcgct gtcgttacct cttcaattat ttcctccagg atttggccca    60
ctaggctttt tgcctgcatc cacaaatgag acagacaaaa gcattaaagt aaccattaaa   120
ggcattaaat aaataattaa attttaatt gaattagtaa acattttttt gattgaagaa    180
taattaactt taaagtactc cgatcgcgtt aacgcttat cacgatacct tctaccacat    240
atcactaaca acatcaacac tcatcactct cgacgacatc cactcgatca ctactctcac    300
acgaccgatt aactcctcat ccacgcggcc gcctgctaaa gttaattatt cttcaatcaa    360
aaaaatgttt actaattcaa ttaaaaattt aattatttat ttaatgcctt taatggttac    420
tttaatgctt ttgtctgtct catttgtgga tgcaggcaaa aagcctagtg ggccaaatcc    480
tggaggaaat aattgaagat agaacccagc ggtactcgct gaggcgatcg c            531
```

<210> SEQ ID NO 35
<211> LENGTH: 1144
<212> TYPE: DNA
<213> ORGANISM: Arabidopsis thaliana

<400> SEQUENCE: 35

```
gaattcatca acaataaaac caggaactca aacatacgg tcatataaga ttctcttgca     60
agtagatacg aggcgttgtg tagcgattag aaggagcttt ttgatatttt cgtttcatgc    120
gcaaatgcat ttgtcttgaa cccctgcctg aaattggatt gtaagtaaag tgctaatgat    180
ggatattgct gtaaacagaa acaatgatct ttaactgatt gatgtcaaag gaatgagtct    240
ggttttatct ttggtatgct ctgaacaatt tttgtatgag aagagaagac tgagatttgc    300
tgtttttaga ttgttcaata gcttccaagt actttggttt taggctttta gctaattagt    360
ttgtgccgtc ttcatatttt ccccttcttc tttgcaattt tgctatttta tggaagctga    420
ttatgaccaa gcatcaatga aggaatctct ccactataac ttatcaggtt cacataactt    480
tcttaaaagt aaaacagtga agaaccattc accttccata tctccagagc aggttcattg    540
catcttagtt agggtttaac cttcaaactt gtctttacac tatcctagga ttctattgtt    600
ttcttgtctt ctttgtattg ctgcatttga ttgacttacc actactctct tgagattggc    660
caatttttgc tgattaacag ttcatttttg ctctaagttt catcagtttt ttttcttggc    720
atggatgttt tgctgaatta tcattcgcct aatgagttac acaaacaaaa ttgtagattt    780
tcagagaaaa caaaacaaaa catatgaata aaaaagttat gcatatgata cgcgttaaga    840
aaaacaaatg attaacgtac gtcggctgtg aagtgttgtt tgatacaatt ggggaagtg    900
acggcacaat gggctggttt cacggcccct ttctaagtca tacacgtctc ctttttttat    960
tttcgttttt ttcaaaataa taaaaataat atagagagtg gcatatccga cggtttagga   1020
tctctgcctt ttctcaactt atagtatata ccaaacactt tctaaggtaa catgagatat   1080
ttcacatcct tttctctctt attcgtttct gagattccct tcttgttgtt gtagccggcg   1140
cgcc                                                                1144
```

<210> SEQ ID NO 36
<211> LENGTH: 1052

```
<212> TYPE: DNA
<213> ORGANISM: Figwort mosaic virus

<400> SEQUENCE: 36
caatcccaca aaaatctgag cttaacagca cagttgctcc tctcagagca gaatcgggta      60
ttcaacaccc tcatatcaac tactacgttg tgtataacgg tccacatgcc ggtatatacg     120
atgactgggg ttgtacaaag gcggcaacaa acggcgttcc cggagttgca cacaagaaat     180
ttgccactat tacagaggca agagcagcag ctgacgcgta cacaacaagt cagcaaacag     240
acaggttgaa cttcatcccc aaaggagaag ctcaactcaa gcccaagagc tttgctaagg     300
ccctaacaag cccaccaaag caaaagccc actggctcac gctaggaacc aaaaggccca      360
gcagtgatcc agccccaaaa gagatccgca ttccagattg ggttcaatca acaaggtacg     420
agccatatca ctttattcaa attggtatcg ccaaaaccaa gaaggaactc ccatcctcaa     480
aggtttgtaa ggaagaattc tcagtccaaa gcctcaacaa ggtcagggta cagagtctcc     540
aaaccattag ccaaaagcta caggagatca atgaagaatc ttcaatcaaa gtaaactact     600
gttccagcac atgcatcatg gtcagtaagt ttcagaaaaa gacatccacc gaagacttaa     660
agttagtggg catctttgaa agtaatcttg tcaacatcga gcagctggct tgtggggacc     720
agacaaaaaa ggaatggtgc agaattgtta ggcgcaccta ccaaaagcat ctttgccttt     780
attgcaaaga taaagcagat tcctctagta caagtgggga acaaaataac gtggaaaaga     840
gctgtcctga cagcccactc actaatgcgt atgacgaacg cagtgacgac cacaaaagaa     900
ttccctctat ataagaaggc attcattccc atttgaagga cacagaaaaa tttgctacat     960
tgtttcacaa acttcaaata ttattcattt atttgtcagc tttcaaactc tttgtttctt    1020
gtttgttgat tgagaatagg taccggcgcg cc                                  1052

<210> SEQ ID NO 37
<211> LENGTH: 1064
<212> TYPE: DNA
<213> ORGANISM: Artificial Sequence
<220> FEATURE:
<223> OTHER INFORMATION: Enhanced 35S Cauliflower Mosaic Virus (E35S)
      promoter

<400> SEQUENCE: 37
caatcccaca aaaatctgag cttaacagca cagttgctcc tctcagagca gaatcgggta      60
ttcaacaccc tcatatcaac tactacgttg tgtataacgg tccacatgcc ggtatatacg     120
atgactgggg ttgtacaaag gcggcaacaa acggcgttcc cggagttgca cacaagaaat     180
ttgccactat tacagaggca agagcagcag ctgacgcgta cacaacaagt cagcaaacag     240
acaggttgaa cttcatcccc aaaggagaag ctcaactcaa gcccaagagc tttgctaagg     300
ccctaacaag cccaccaaag caaaagccc actggctcac gctaggaacc aaaaggccca      360
gcagtgatcc agccccaaaa gagatcccac gtgcggaccg cctgcaggcc gcgttatcaa     420
gctaactgca ggtccgatgt gagactttc aacaaagggt aatatccgga aacctcctcg      480
gattccattg cccagctatc tgtcacttta ttgtgaagat agtggaaaag gaaggtggct     540
cctacaaatg ccatcattgc gataaaggaa aggccatcg tgaagatgcc tctgccgaca      600
gtggtcccaa agatggaccc ccacccacga ggagcatcgt ggaaaaagaa gacgttccaa     660
ccacgtcttc aaagcaagtg gattgatgtg atggtccgat tgagactttt caacaaaggg     720
taatatccgg aaacctcctc ggattccatt gcccagctat ctgtcacttt attgtgaaga    780
tagtggaaaa ggaaggtggc tcctacaaat gccatcattg cgataaagga aaggccatcg     840
```

```
ttgaagatgc ctctgccgac agtggtccca aagatggacc cccacccacg aggagcatcg    900
tggaaaaaga agacgttcca accacgtctt caaagcaagt ggattgatgt gatatctcca    960
ctgacgtaag ggatgacgca caatcccact atccttcgca agacccttcc tctatataag   1020
gaagttcatt tcatttggag aggaccaggt ggtaccggcg cgcc                    1064
```

<210> SEQ ID NO 38
<211> LENGTH: 1156
<212> TYPE: DNA
<213> ORGANISM: Artificial sequence
<220> FEATURE:
<223> OTHER INFORMATION: Enhanced 35S Cauliflower Mosaic Virus (E35S) promoter with Petunia Leader

<400> SEQUENCE: 38

```
caatcccaca aaaatctgag cttaacagca cagttgctcc tctcagagca gaatcgggta     60
ttcaacaccc tcatatcaac tactacgttg tgtataacgg tccacatgcc ggtatatacg    120
atgactgggg ttgtacaaag gcggcaacaa acggcgttcc cggagttgca cacaagaaat    180
ttgccactat tacagaggca agagcagcag ctgacgcgta cacaacaagt cagcaaacag    240
acaggttgaa cttcatcccc aaaggagaag ctcaactcaa gcccaagagc tttgctaagg    300
ccctaacaag cccaccaaag caaaaagccc actggctcac gctaggaacc aaaaggccca    360
gcagtgatcc agccccaaaa gagatcccac gtgcggaccg cctgcaggcc gcgttatcaa    420
gctaactgca ggtccgatgt gagactttc aacaaagggt aatatccgga aacctcctcg    480
gattccattg cccagctatc tgtcacttta ttgtgaagat agtggaaaag gaaggtggct    540
cctacaaatg ccatcattgc gataaaggaa aggccatcgt tgaagatgcc tctgccgaca    600
gtggtcccaa agatggaccc ccacccacga ggagcatcgt ggaaaaagaa gacgttccaa    660
ccacgtcttc aaagcaagtg gattgatgtg atggtccgat tgagactttt caacaaaggg    720
taatatccgg aaacctcctc ggattccatt gcccagctat ctgtcacttt attgtgaaga    780
tagtggaaaa ggaaggtggc tcctacaaat gccatcattg cgataaagga aaggccatcg    840
ttgaagatgc ctctgccgac agtggtccca aagatggacc cccacccacg aggagcatcg    900
tggaaaaaga agacgttcca accacgtctt caaagcaagt ggattgatgt gatatctcca    960
ctgacgtaag ggatgacgca caatcccact atccttcgca agacccttcc tctatataag   1020
gaagttcatt tcatttggag aggacacaga aaaatttgct acattgtttc acaaacttca   1080
aatattattc atttatttgt cagctttcaa actctttgtt tcttgtttgt tgattgagaa   1140
taggtaccgg cgcgcc                                                   1156
```

<210> SEQ ID NO 39
<211> LENGTH: 1462
<212> TYPE: DNA
<213> ORGANISM: Artificial sequence
<220> FEATURE:
<223> OTHER INFORMATION: 35S Cauliflower Mosaic Virus promoter with tobacco mosaic virus translational leader

<400> SEQUENCE: 39

```
atagcgacat ctatgataga gcgccacaat aacaaacaat tccaatccca caaaaatctg     60
agcttaacag cacagttgct cctctcagag cagaatcggg tattcaacac cctcatatca    120
actactacgt tgtgtataac ggtccacatg ccggtatata cgatgactgg ggttgtacaa    180
aggcggcaac aaacggcgtt cccggagttg cacacaagaa atttgccact attacagagg    240
```

-continued

| | |
|---|---|
| caagagcagc agctgacgcg tacacaacaa gtcagcaaac agacaggttg aacttcatcc | 300 |
| ccaaaggaga agctcaactc aagcccaaga gctttgctaa ggccctaaca agcccaccaa | 360 |
| agcaaaaagc ccactggctc acgctaggaa ccaaaaggcc cagcagtgat ccagccccaa | 420 |
| aagagatctc ctttgccccg gagattacaa tggacgattt cctctatctt tacgatctag | 480 |
| gaaggaagtt cgaaggtgaa ggtgacgaca ctatgttcac cactgataat gagaaggtta | 540 |
| gcctcttcaa tttcagaaag aatgctgacc cacagatggt tagagaggcc tacgcagcag | 600 |
| gtctcatcaa gacgatctac ccgagtaaca atctccagga gatcaaatac cttcccaaga | 660 |
| aggttaaaga tgcagtcaaa agattcagga ctaattgcat caagaacaca gagaaagaca | 720 |
| tatttctcaa gatcagaagt actattccag tatggacgat tcaaggcttg cttcataaac | 780 |
| caaggcaagt aatagagatt ggagtctcta aaaggtagt tcctactgaa tctaaggcca | 840 |
| tgcatggagt ctaagattca aatcgaggat ctaacagaac tcgccgtgaa gactggcgaa | 900 |
| cagttcatac agagtctttt acgactcaat gacaagaaga aaatcttcgt caacatggtg | 960 |
| gagcacgaca ctctggtcta ctccaaaaat gtcaaagata cagtctcaga agaccaaagg | 1020 |
| gctattgaga cttttcaaca aaggataatt tcgggaaacc tcctcggatt ccattgccca | 1080 |
| gctatctgtc acttcatcga aaggacagta gaaaaggaag gtggctccta caaatgccat | 1140 |
| cattgcgata aaggaaaggc tatcattcaa gatctctctg ccgacagtgg tcccaaagat | 1200 |
| ggaccccac ccacgaggag catcgtggaa aagaagacg ttccaaccac gtcttcaaag | 1260 |
| caagtggatt gatgtgacat ctccactgac gtaagggatg acgcacaatc ccactatcct | 1320 |
| tcgcaagacc cttcctctat ataaggaagt tcatttcatt tggagaggac acgctcgagt | 1380 |
| ataagagctc tattttaca acaattacca acaacaacaa acaacaaaca acattacaat | 1440 |
| tacatttaca attaccgacg tc | 1462 |

<210> SEQ ID NO 40
<211> LENGTH: 1008
<212> TYPE: DNA
<213> ORGANISM: Meloidogyne incognita

<400> SEQUENCE: 40

| | |
|---|---|
| atgatgaaga gatttggaat ttatacttct ttcctcgaat ttttgttaat aattttaacg | 60 |
| atttcaacag tcagaggtcc gaaaattgag catgactctc aaacaggagc ttctgcatct | 120 |
| gcttcgggtt catttccaat tgttttacca cataatgaac taaagcagga cggtggcaaa | 180 |
| tttatttgg aaggagacga aaagaatgcc tgccttctat atattgaatc gatttctgtt | 240 |
| gtgttatata acgtaaaaca aaaaatgtct gcttgggcga ccattaatgc aacttctaag | 300 |
| ggagcaacat atagtggtaa aattgagtgt ccagcaactc ataatacagg acaggagttt | 360 |
| aaaatttcat tgcaagcaat tgctggcggt gaaggtgttt caggctatta tattggtgat | 420 |
| aaaaagaaag tcatttttccg gttaagcaaa gtcgatgttg atttaatatt taactttact | 480 |
| tcatcagctt attgggagtt ggtgaatgct gatgttagga caataagttt ggatggcgca | 540 |
| gaagaaggtg gagttccgag tgtcgataac acctggcgac ttgtttctgg tataagcagc | 600 |
| aacaataaag gatggatttt cacagataat caatctccgg cctggaatat taatgggttt | 660 |
| aaagactacg ccttctcttg tggtcgaact agtccaatta tttgggcaaa acatgatacg | 720 |
| gatgaaaaaa gcctggaaca tgcagttggt ttggcttttc ataatttaca gtttcaattg | 780 |
| aattcaactt atatttctcc ggataaaaaa agaatgcaa agtttggctg gcgtgttaat | 840 |
| gattgtgcac ctctattaag tattggtact tggatgattc ttgtggttgc aattattttt | 900 |

```
attggagttc tctctttttgg attttaatg cttaattctg tccaaacaat gagccgattt    960
gacgacccaa acaaaaaca gataattatt agttctaaag aaaattag                 1008
```

<210> SEQ ID NO 41
<211> LENGTH: 335
<212> TYPE: PRT
<213> ORGANISM: Meloidogyne incognita

<400> SEQUENCE: 41

| | | | | | | | | | | | | | | |
|---|---|---|---|---|---|---|---|---|---|---|---|---|---|---|
| Met | Met | Lys | Arg | Phe | Gly | Ile | Tyr | Thr | Ser | Phe | Leu | Glu | Phe | Leu |
| 1 | | | | 5 | | | | | 10 | | | | | 15 |
| Ile | Ile | Leu | Thr | Ile | Ser | Thr | Val | Arg | Gly | Pro | Lys | Ile | Glu | His | Asp |
| | | | 20 | | | | | 25 | | | | | 30 | | |
| Ser | Gln | Thr | Gly | Ala | Ser | Ala | Ser | Ala | Ser | Gly | Ser | Phe | Pro | Ile | Val |
| | | | 35 | | | | | 40 | | | | | 45 | | |
| Leu | Pro | His | Asn | Glu | Leu | Lys | Gln | Asp | Gly | Gly | Lys | Phe | Tyr | Leu | Glu |
| | | 50 | | | | | 55 | | | | | 60 | | | |
| Gly | Asp | Glu | Lys | Asn | Ala | Cys | Leu | Leu | Tyr | Ile | Glu | Ser | Ile | Ser | Val |
| 65 | | | | | 70 | | | | | 75 | | | | | 80 |
| Val | Leu | Tyr | Asn | Val | Lys | Gln | Lys | Met | Ser | Ala | Trp | Ala | Thr | Ile | Asn |
| | | | | 85 | | | | | 90 | | | | | 95 | |
| Ala | Thr | Ser | Lys | Gly | Ala | Thr | Tyr | Ser | Gly | Lys | Ile | Glu | Cys | Pro | Ala |
| | | | 100 | | | | | 105 | | | | | 110 | | |
| Thr | His | Asn | Thr | Gly | Gln | Glu | Phe | Lys | Ile | Ser | Leu | Gln | Ala | Ile | Ala |
| | | | 115 | | | | | 120 | | | | | 125 | | |
| Gly | Gly | Glu | Gly | Val | Ser | Gly | Tyr | Tyr | Ile | Gly | Asp | Lys | Lys | Lys | Val |
| | | | 130 | | | | | 135 | | | | | 140 | | |
| Ile | Phe | Arg | Leu | Ser | Lys | Val | Asp | Val | Asp | Leu | Ile | Phe | Asn | Phe | Thr |
| 145 | | | | | 150 | | | | | 155 | | | | | 160 |
| Ser | Ser | Ala | Tyr | Trp | Glu | Leu | Val | Asn | Ala | Asp | Val | Arg | Thr | Ile | Ser |
| | | | | 165 | | | | | 170 | | | | | 175 | |
| Leu | Asp | Gly | Ala | Glu | Glu | Gly | Val | Pro | Ser | Val | Asp | Asn | Thr | Trp |
| | | | 180 | | | | | 185 | | | | | 190 | | |
| Arg | Leu | Val | Ser | Gly | Ile | Ser | Ser | Asn | Lys | Gly | Trp | Ile | Phe | Thr |
| | | | 195 | | | | | 200 | | | | | 205 | | |
| Asp | Asn | Gln | Ser | Pro | Ala | Trp | Asn | Ile | Asn | Gly | Phe | Lys | Asp | Tyr | Ala |
| | | | 210 | | | | | 215 | | | | | 220 | | |
| Phe | Ser | Cys | Gly | Arg | Thr | Ser | Pro | Ile | Ile | Trp | Ala | Lys | His | Asp | Thr |
| 225 | | | | | 230 | | | | | 235 | | | | | 240 |
| Asp | Glu | Lys | Ser | Leu | Glu | His | Ala | Val | Gly | Leu | Ala | Phe | His | Asn | Leu |
| | | | | 245 | | | | | 250 | | | | | 255 | |
| Gln | Phe | Gln | Leu | Asn | Ser | Thr | Tyr | Ile | Ser | Pro | Asp | Lys | Lys | Arg | Met |
| | | | 260 | | | | | 265 | | | | | 270 | | |
| Ala | Lys | Phe | Gly | Trp | Arg | Val | Asn | Asp | Cys | Ala | Pro | Leu | Leu | Ser | Ile |
| | | | 275 | | | | | 280 | | | | | 285 | | |
| Gly | Thr | Trp | Met | Ile | Leu | Val | Val | Ala | Ile | Ile | Phe | Ile | Gly | Val | Leu |
| | | | 290 | | | | | 295 | | | | | 300 | | |
| Ser | Phe | Gly | Phe | Leu | Met | Leu | Asn | Ser | Val | Gln | Thr | Met | Ser | Arg | Phe |
| 305 | | | | | 310 | | | | | 315 | | | | | 320 |
| Asp | Asp | Pro | Lys | Gln | Lys | Gln | Ile | Ile | Ile | Ser | Ser | Lys | Glu | Asn |
| | | | | 325 | | | | | 330 | | | | | 335 | |

<210> SEQ ID NO 42
<211> LENGTH: 1102

<212> TYPE: DNA
<213> ORGANISM: Meloidogyne incognita

<400> SEQUENCE: 42

```
ctgcaagaag aaactgttga ttaccgcaac aataaggagg atattgagac tttcaaagaa      60
ttgggaataa atgaagaatt gtgcagtgct tgtgaacgta ttggttggaa aaaacctatg     120
cctatacaac aaaaagttat tccgattgcc ttgaagggaa gagatgtgat tggattggca     180
gaaactggtt ctggcaaaac tgcagcattt gctcttccaa tacttcaatc cttaatgtcc     240
aatccacagc gtctctttgc cgttgtatta gctcctacga gagaattggc atttcaaatt     300
tcggatcagt ttgtggcttt aggtgcaact atcggcctcc aagtttctac aattgtcggt     360
ggtattgata tgtcaacaca gacattgtct ctttctaaaa ggcctcatgt tattgttgca     420
actcctggtc ggcttgttga ccacctcgaa aacaccaaag gttttgatct tcgatcagtc     480
aaatatttgg ttttggacga agcggataga atacttaata tggactttga attggaattg     540
gataaaattc ttaaagttat tccaaataca aggcatacat ttttattttc ggcaactatg     600
acgcacaagg tttcaaaatt agaaagggcc catttaaaga agcctgttcg tgttgaatta     660
tctaccaaat atcaaacagt tagcacattg attcaaaata tgcttttttat tcccttcaag     720
tataaggagg cttatctagt ccacgttttg aacgaaaaag caggcaatac agcaatagtt     780
ttttgttcaa catgtgcaag ttcagtaaaa atagctctaa tgttaaggca attaagtttt     840
ggagcaatag ctttacatgg acaaatgtca cagccaaaac gtttgggagc tttaaataag     900
ttcaaaaaga aggatcggcc aattttggtt tgtactgatg ttgcttctcg aggtcttgat     960
attcctcatg ttgatatggt tttaaattat gacgtcccaa cgcattcaaa agattatgtt    1020
catcgtgtag gaaggactgc tagggctggg aagtcaggaa tttcaatcac aatagtcacc    1080
caatacgatg ttgaaattta tc                                             1102
```

<210> SEQ ID NO 43
<211> LENGTH: 367
<212> TYPE: PRT
<213> ORGANISM: Meloidogyne incognita

<400> SEQUENCE: 43

```
Leu Gln Glu Glu Thr Val Asp Tyr Arg Asn Asn Lys Glu Asp Ile Glu
1               5                   10                  15

Thr Phe Lys Glu Leu Gly Ile Asn Glu Glu Leu Cys Ser Ala Cys Glu
            20                  25                  30

Arg Ile Gly Trp Lys Lys Pro Met Pro Ile Gln Gln Lys Val Ile Pro
        35                  40                  45

Ile Ala Leu Lys Gly Arg Asp Val Ile Gly Leu Ala Glu Thr Gly Ser
    50                  55                  60

Gly Lys Thr Ala Ala Phe Ala Leu Pro Ile Leu Gln Ser Leu Met Ser
65                  70                  75                  80

Asn Pro Gln Arg Leu Phe Ala Val Val Leu Ala Pro Thr Arg Glu Leu
            85                  90                  95

Ala Phe Gln Ile Ser Asp Gln Phe Val Ala Leu Gly Ala Thr Ile Gly
            100                 105                 110

Leu Gln Val Ser Thr Ile Val Gly Gly Ile Asp Met Ser Thr Gln Thr
        115                 120                 125

Leu Ser Leu Ser Lys Arg Pro His Val Ile Val Ala Thr Pro Gly Arg
    130                 135                 140

Leu Val Asp His Leu Glu Asn Thr Lys Gly Phe Asp Leu Arg Ser Val
```

```
                145                 150                 155                 160
Lys Tyr Leu Val Leu Asp Glu Ala Asp Arg Ile Leu Asn Met Asp Phe
                    165                 170                 175

Glu Leu Glu Leu Asp Lys Ile Leu Lys Val Ile Pro Asn Thr Arg His
                180                 185                 190

Thr Phe Leu Phe Ser Ala Thr Met Thr His Lys Val Ser Lys Leu Glu
            195                 200                 205

Arg Ala His Leu Lys Lys Pro Val Arg Val Glu Leu Ser Thr Lys Tyr
        210                 215                 220

Gln Thr Val Ser Thr Leu Ile Gln Asn Met Leu Phe Ile Pro Phe Lys
225                 230                 235                 240

Tyr Lys Glu Ala Tyr Leu Val His Val Leu Asn Glu Lys Ala Gly Asn
                245                 250                 255

Thr Ala Ile Val Phe Cys Ser Thr Cys Ala Ser Ser Val Lys Ile Ala
                260                 265                 270

Leu Met Leu Arg Gln Leu Ser Phe Gly Ala Ile Ala Leu His Gly Gln
                275                 280                 285

Met Ser Gln Pro Lys Arg Leu Gly Ala Leu Asn Lys Phe Lys Lys Lys
            290                 295                 300

Asp Arg Pro Ile Leu Val Cys Thr Asp Val Ala Ser Arg Gly Leu Asp
305                 310                 315                 320

Ile Pro His Val Asp Met Val Leu Asn Tyr Asp Val Pro Thr His Ser
                325                 330                 335

Lys Asp Tyr Val His Arg Val Gly Arg Thr Ala Arg Ala Gly Lys Ser
                340                 345                 350

Gly Ile Ser Ile Thr Ile Val Thr Gln Tyr Asp Val Glu Ile Tyr
            355                 360                 365

<210> SEQ ID NO 44
<211> LENGTH: 261
<212> TYPE: DNA
<213> ORGANISM: Meloidogyne incognita

<400> SEQUENCE: 44
tcagaaaaat tttggcgaga aaacgctcag agatttaatg aaaagaattt tgaattaata      60 aaatattaa ttcgattact tgattctagt gatgttttgg tactttgtgt tgctgctcat     120
gatgttggag aatatgttag acattttcca cgtggaaaag atattgtcga gcaatatcaa     180
ggcaaacaag cggtaatgaa attgttaagt gctgaagatc aaatgttag atatcatgca      240 cttttagcaa ttcaaaaatt a                                               261

<210> SEQ ID NO 45
<211> LENGTH: 87
<212> TYPE: PRT
<213> ORGANISM: Meloidogyne incognita

<400> SEQUENCE: 45

Ser Glu Lys Phe Trp Arg Glu Asn Ala Gln Arg Phe Asn Glu Lys Asn
1               5                   10                  15

Phe Glu Leu Ile Lys Ile Leu Ile Arg Leu Leu Asp Ser Ser Asp Val
            20                  25                  30

Leu Val Leu Cys Val Ala Ala His Asp Val Gly Glu Tyr Val Arg His
        35                  40                  45

Phe Pro Arg Gly Lys Asp Ile Val Glu Gln Tyr Gln Gly Lys Gln Ala
    50                  55                  60
```

```
Val Met Lys Leu Leu Ser Ala Glu Asp Pro Asn Val Arg Tyr His Ala
 65                  70                  75                  80
Leu Leu Ala Ile Gln Lys Leu
                 85

<210> SEQ ID NO 46
<211> LENGTH: 705
<212> TYPE: DNA
<213> ORGANISM: Meloidogyne incognita

<400> SEQUENCE: 46
ggcgcgcctc agcagtcgct gtcgttacca tgactttctt tttatcacca atataatagc     60
ctgaaacacc ttcaccgcca gcaattgctt gcaatgaaat tttaaactcc tgtcctgtat    120
tatgagttgc tggacactca attttaccac tatatgttgc tcccttagaa gttgcattaa    180
tggtcgccca agcagacatt ttttgtttta cgttatataa cacaacagaa atcgattcaa    240
tatatagaag gcaggcattc ttttcgtctc cttccaaata agtactccga tcgcgttaac    300
gctttatcac gataccttct accacatatc actaacaaca tcaacactca tcactctcga    360
cgacatccac tcgatcacta ctctcacacg accgattaac tcctcatcca cgcggccgcc    420
tgcatttgga aggagacgaa aagaatgcct gccttctata tattgaatcg atttctgttg    480
tgttatataa cgtaaaacaa aaaatgtctg cttgggcgac cattaatgca acttctaagg    540
gagcaacata tagtggtaaa attgagtgtc cagcaactca taatacagga caggagttta    600
aaatttcatt gcaagcaatt gctggcggtg aaggtgtttc aggctattat attggtgata    660 aaagaaagt cattagaacc cagcggtact cgctgaggcg atcgc                     705

<210> SEQ ID NO 47
<211> LENGTH: 250
<212> TYPE: DNA
<213> ORGANISM: Meloidogyne incognita

<400> SEQUENCE: 47
atttggaagg agacgaaaag aatgcctgcc ttctatatat tgaatcgatt tctgttgtgt     60
tatataacgt aaaacaaaaa atgtctgctt gggcgaccat taatgcaact tctaagggag    120
caacatatag tggtaaaatt gagtgtccag caactcataa tacaggacag gagtttaaaa    180
tttcattgca agcaattgct ggcggtgaag tgtttcagg ctattatatt ggtgataaaa    240
agaaagtcat                                                          250
```